United States Patent
Hergenrother et al.

(10) Patent No.: US 12,235,275 B2
(45) Date of Patent: Feb. 25, 2025

(54) FLUORESCENT SUBSTRATES FOR POLY(ADP-RIBOSYL) HYDROLASES

(71) Applicant: The Board of Trustees of the University of Illinois, Urbana, IL (US)

(72) Inventors: Paul J. Hergenrother, Champaign, IL (US); Bryon S. Drown, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 128 days.

(21) Appl. No.: 17/274,395

(22) PCT Filed: Sep. 9, 2019

(86) PCT No.: PCT/US2019/050221
§ 371 (c)(1),
(2) Date: Mar. 8, 2021

(87) PCT Pub. No.: WO2020/055753
PCT Pub. Date: Mar. 19, 2020

(65) Prior Publication Data
US 2022/0050112 A1    Feb. 17, 2022

Related U.S. Application Data

(60) Provisional application No. 62/728,955, filed on Sep. 10, 2018.

(51) Int. Cl.
*G01N 33/58*    (2006.01)
*C09K 11/06*    (2006.01)
*G01N 21/64*    (2006.01)

(52) U.S. Cl.
CPC ............ *G01N 33/582* (2013.01); *C09K 11/06* (2013.01); *G01N 21/6428* (2013.01); *C09K 2211/1022* (2013.01); *C09K 2211/1059* (2013.01); *G01N 2021/6439* (2013.01)

(58) Field of Classification Search
CPC ............ G01N 33/582; G01N 21/6428; C09K 2211/1022; C09K 2211/1059
USPC ....................................................... 544/283
See application file for complete search history.

(56) References Cited

U.S. PATENT DOCUMENTS

| | | | |
|---|---|---|---|
| 5,242,805 A | 9/1993 | Naleway et al. | |
| 7,393,640 B2 | 7/2008 | Kumar et al. | |
| 2008/0176261 A1 | 7/2008 | Nottbohm et al. | |

OTHER PUBLICATIONS

Nottbohm et al. Angewandte Chemie, International Edition (2007), 46(12), 2066-2069.*
Drown et al., "Monitoring Poly(ADP-ribosyl)glycohydrolase Activity with a Continuous Fluorescent Substrate," Cell Chem Biol., 25(12):1562-1570, Dec. 2018.
Dunstan et al., "Tructure and Mechanism of a Canonical poly(ADP-Ribose) Glycohydrolase," Nature Comm., 3(878):1-6, Jun. 2012.
Finch et al., "Selective Small Molecule Inhibition of Poly(ADP-Ribose) Glycohydrolase (PARG)," ACS Chem Biol., 7(3):563-570, Mar. 2012.
International Search Report and Written Opinion of the ISA/US in PCT/US2019/050221, dated Jan. 10, 2020, 11pgs.
James et al., "First-in-Class Chemical Probes against Poly(ADP-ribose) Glycohydrolase (PARG) Inhibit DNA Repair with Differential Pharmacology to Olaparib," ACS Chem Biol., 11(11):3179-3190, Nov. 2016.
Koh et al., "SAR Analysis of Adenosine Diphosphate (Hydroxymethyl)pyrrolidinediol Inhibition of Poly(ADP-ribose) Glycohydrolase," J Med Chem., 46(20):4322-4332, Sep. 2003.
Lambrecht et al., "Synthesis of Dimeric ADP-Ribose and Its Structure with Human Poly(ADP-ribose) Glycohydrolase," J Am Chem Soc., 137(10):3558-3564, Mar. 2015.
Oppenheimer, "Structural Determination and Stereospecificity of the Choleragen-catalyzed Reaction of NAD+ with Guanidines*," J Biol Chem., 253(14):4907-4910, Jul. 1978.
Sharifi et al., "Deficiency of Terminal ADP-Ribose Protein Glycohydrolase TARG1/C6orf130 in Neurodegenerative Disease," EMBO J., 32(9):1225-1237, May 2013.
Stowell et al., "A High-Throughput Screening-Compatible Homogeneous Time-Resolved Fluorescence Assay Measuring the Glycohydrolase Activity of Human poly(ADP-Ribose) Glycohydrolase," Anal Biochem., 503:58-64, Jun. 2016.

* cited by examiner

*Primary Examiner* — Kahsay Habte
(74) *Attorney, Agent, or Firm* — Haukaas Fortius PLLC; Michael Haukaas

(57) ABSTRACT

The post-translational modification (PTM) and signaling molecule poly(ADP-ribose) (PAR) has an impact on diverse biological processes. PTM is regulated by a series of ADP-ribosyl glycohydrolases (PARG enzymes) that cleave polymers and/or liberate monomers from their protein targets. Disclosed herein is a substrate for monitoring PARG activity, TFMU-ADPr, which directly reports on total PAR hydrolase activity via release of a fluorophore; this substrate has excellent reactivity, generality, stability, and usability. A second substrate, TFMU-IDPr, selectively reports on PARG activity only from the enzyme ARH3. Use of these probes in whole-cell lysate experiments has revealed a mechanism by which ARH3 is inhibited by cholera toxin. TFMU-ADPr and TFMU-IDPr are versatile tools for assessing small-molecule inhibitors in vitro and probing the regulation of ADP-ribosyl catabolic enzymes.

18 Claims, 14 Drawing Sheets

A

*Fluorescent PARG and ARH3 Substrates*

*General Substrate*

*ARH3-selective Substrate*

*Discovery of Endogenous ARH3 Inhibitor*

B

C

ADPr-Arg

FLUORESCENT SUBSTRATES FOR POLY(ADP-RIBOSYL) HYDROLASES

RELATED APPLICATIONS

This application is a National Stage filing under 35 U.S.C. § 371 of International Application No. PCT/US2019/050221 filed Sep. 9, 2019, which claims priority under 35 U.S.C. § 119 (e) to U.S. Provisional Patent Application No. 62/728,955, filed Sep. 10, 2018, which applications are incorporated herein by reference.

GOVERNMENT SUPPORT

This invention was made with government support under Grant No. R21 CA212732 awarded by the National Institutes of Health. The government has certain rights in the invention.

BACKGROUND OF THE INVENTION

Many biological processes are regulated by post-translational modifications (PTMs), with ADP-ribosylation being one of the most thoroughly studied nucleotide-containing modifications. This modification includes a collection of "writers", "readers", and "erasers".

The writers, poly(ADP-ribosyl) polymerases (PARPs), modify protein substrates with adenine diphosphate ribose (ADPr). Nearly all nucleophilic amino acids have been shown to be modified: glutamate, aspartate, cysteine, lysine, and serine. While the majority of PARPs can only transfer a single ADPr unit from $NAD^+$, the founding member of the family, PARP1 (but also PARP2 and tankyrases), can synthesize large polymers termed poly(ADP-ribose) (PAR). A wealth of literature over several decades has established PARylation as central for proper DNA damage response, chromatin maintenance, cell division, and DNA replication.

In contrast, much is still unknown about the regulation of ADPr erasure. Several families of enzymes are responsible for removal and degradation of PARylation. Poly(ADP-ribose) glycohydrolase (PARG) hydrolyzes the 2',1" glycosidic linkage (arrow in Scheme 1B) of polymers mainly in an exo manner. PARG modifies PARylated proteins by removing polymers down to the last unit, which it is incapable of removing. ADP-ribosyl hydrolase 3 (ARH3 or ADPRHL2) is also capable of degrading PAR polymers, albeit at a reduced rate. Until recently, neither of these proteins were believed capable of removing the last ADPr unit directly bonded to the protein side chain. This hydrolysis is carried out by ARH1 or an enzymatic member of the macrodomain family (terminal ADP-ribosyl protein glycohydrolase (TARG1), MACROD1, and MACROD2 in mammals). Recently ARH3 was shown to be the sole enzyme capable of hydrolyzing mono-ADP-ribosyl serine. Beyond substrate recognition, little is known about how these ADPr erasers are regulated or the relative importance of different erasers in various biological contexts. In particular, study of PAR cleavage has been limited by the challenge of separating contributions to PAR degradation by PARG and by ARH3. Several reports suggest that the specific activity of PARG is significantly greater than ARH3, however, the cellular distribution of these two enzymes differ as do their regulatory domains. Genetic knockout of ARH3 does not affect the lifetime of long polymers but does result in longer lived short polymers, thus much more detailed information on the relative contribution of PAR-degrading enzymes is needed.

The most widely employed enzyme assays for measuring PARG/ARH3 activity rely on radioisotopically labelled and enzymatically produced PAR. The production and isolation of labelled PAR is limited to 0.3-2 mg scale (Menard and Poirier, 2011). After treatment with PARG, reaction mixtures are separated by TLC or HPLC and quantified by autoradiography or liquid scintillation counting. This technique, while sensitive, is laborious and not scalable. Recent efforts to develop more scalable PARG activity assays have been modestly successful, for example, a four-component FRET system to detect the interaction between a PARylated protein and XRCC1. While this approach has been implemented in microtiter format and utilized to discover a first-in-class PARG inhibitor, it suffers from an inability to accurately measure enzyme kinetics and cannot operate in cell lysate.

There clearly is still an unmet need for a facile and continuous activity assay for PAR-degrading enzymatic activity. Accordingly, a substrate to signal such enzymatic activity in a cell lysate would be a useful tool.

SUMMARY

Herein is described the design, synthesis, and evaluation of fluorescent probes for PAR hydrolyzing enzymes, including a compound that is processed by both ARH3 and PARG, and another that is a selective substrate for ARH3. This latter probe has enabled the first direct measurements of ARH3 activity in cells and was then used to discover the first specific means for cellular ARH3 inhibition.

Accordingly, this disclosure provides a compound of Formula I.

$$\text{AM-L-FS1-PP-FS2-NB} \qquad (I),$$

or a salt thereof,
wherein
  AM is an aromatic chromophore;
  L is a linker;
  FS1 and FS2 are furanose moieties;
  PP is a monophosphate, diphosphate, or triphosphate; and
  NB is a nucleobase;
  wherein the C5-carbons of FS1 and FS2 are covalently bonded to PP via a C—O bond, the C1-carbon of FS2 is covalently bonded to NB via a C—N bond, and the C1-carbon of FS1 is covalently bonded to AM via L.

This disclosure also provides a compound of Formula I that is a compound of Formula II:

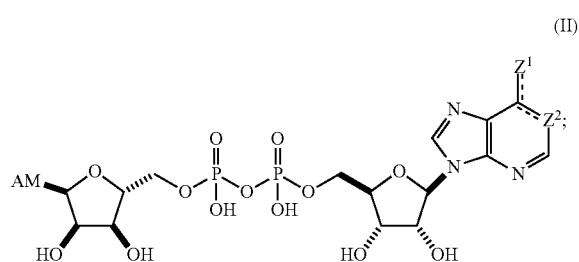

wherein
  ╌╌╌╌ is a single or double bond; and
  $Z^1$ is O and $Z^2$ is NH, wherein ╌╌╌╌ on $Z^1$ is a double bond and ╌╌╌╌ on $Z^2$ is a single bond; or
  $Z^1$ is $NH_2$ and $Z^2$ is N, wherein ╌╌╌╌ on $Z^1$ is a single bond and ╌╌╌╌ on $Z^2$ is a double bond.

In some embodiments, AM is a radical of 7-hydroxy-4-(trifluoromethyl)-2H-chromen-2-one. In other embodiments, AM is an amino acid (AA). In yet other embodiments, L is absent.

Additionally, this disclosure provides a method a method of detecting poly(ADP-ribose) (PAR) cellular activity comprising:

a) contacting a compound described above and constituents of a cell or a whole cell lysate to form a mixture; and b) detecting changes in fluorescence in the mixture; wherein the compound is a substrate of poly(ADP-ribose) glycohydrolase (PARG), and PARG selectively hydrolyses the compound to release the AM moiety as AM-OH;

the compound is a substrate of ADP-ribosylhydrolase 3 (ARH3), and ARH3 selectively hydrolyses the compound to release the AM moiety as AM-OH;

or a combination thereof; wherein AM-OH is fluorescent and an increase in fluorescence indicates PAR cellular activity.

The invention provides novel compounds of Formulas I-IV, intermediates for the synthesis of compounds of Formulas I-IV, as well as methods of preparing compounds of Formulas I-IV. The invention also provides compounds of Formulas I-IV that are useful as intermediates for the synthesis of other useful compounds.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
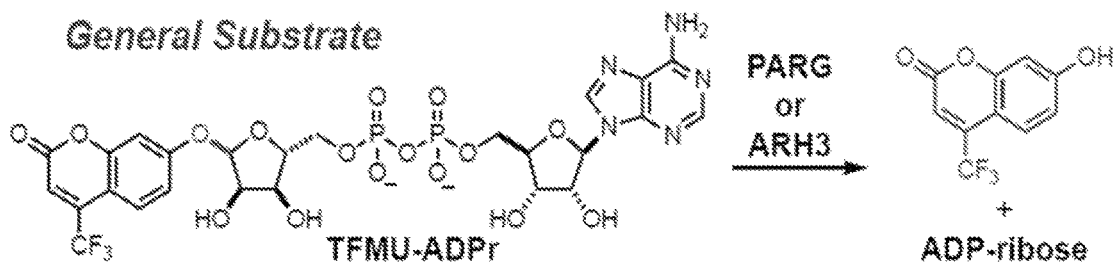
FIG. 1. A. Fluorescent PARG and ARH3 substrates and ARH3 inhibitor. Molecular docking sugar nucleotides with hPARG and LchARH3 using Glide XP: B. ADPr and IDPr are docking into hPARG (PDB: 5A7R); C. ADPr and IDPr are docking into LchARH3 (PDB: 6G1Q).
Figure 1:
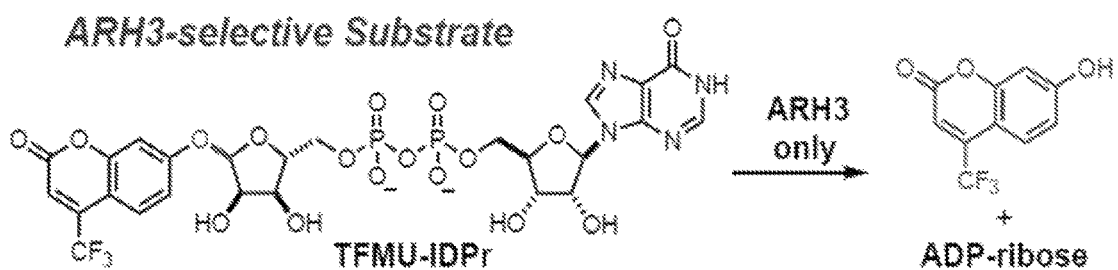
Figure 1:
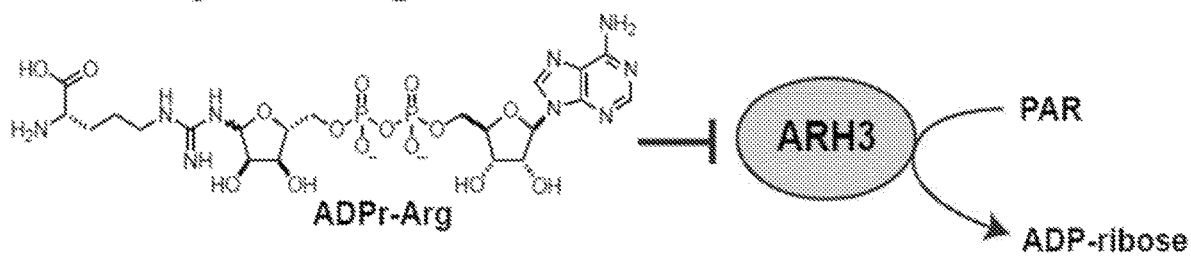
Figure 1:
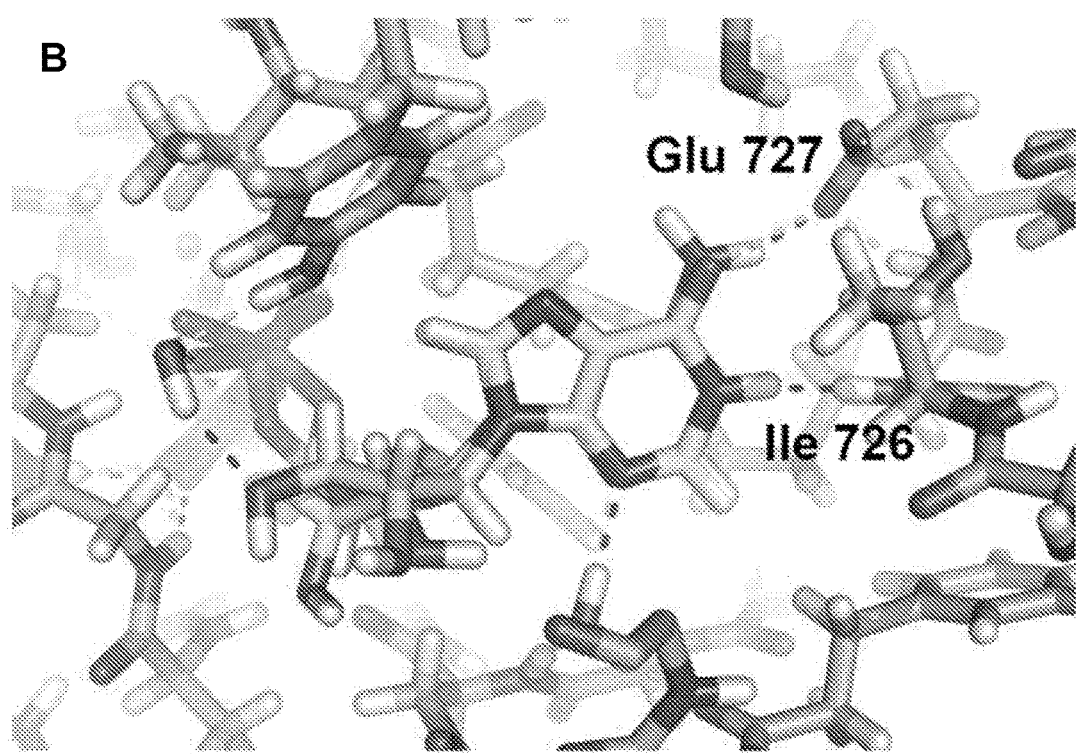
Figure 1:
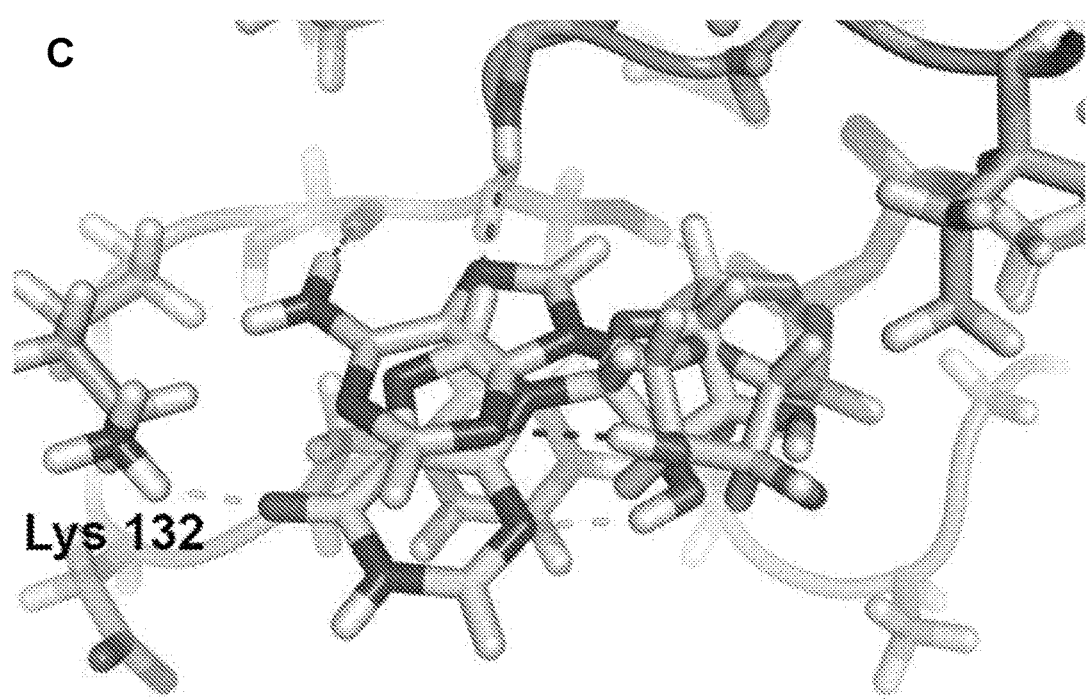

ADP-ribosylation has long captured interest due to its prevalence in normal biological processes and in disease states, but study of this PTM has traditionally relied on imprecise and laborious methods for measuring the activity of ADPr erasers. As such, the conditions and mechanisms by which PAR is regulated are poorly understood. Herein is introduced a rapid and precise technology for measuring poly(ADP-ribose) glycohydrolase activity. Recent advances in pyrophosphate couplings have also improved the capability to construct sugar nucleotides in a modular and scalable fashion, leading to robust and scalable syntheses of the target substrates. These substrates are useful for the detection and quantitation of endogenous cellular PARG and ARH3 activity, and the utility of this tool is increased with the discovery that replacement of the nucleobase provides selectivity for ARH3 over PARG. Together this toolset is expected to greatly enhance the ability to interrogate PAR-cleaving enzymes.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five substituents on the phenyl.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system.

Further, any substituent can be bonded to a carbon or other atom by a linker, such as (CH$_2$)n or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, □-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or (C1-C6)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

Embodiments of the Invention

This disclosure provides various embodiments of a compound of Formula I:

AM-L-FS1-PP-FS2-NB   (I), or a salt thereof,
wherein
AM is an aromatic chromophore;
L is a linker;
FS1 and FS2 are furanose moieties;
PP is a monophosphate, diphosphate, or triphosphate; and
NB is a nucleobase;
wherein the C5-carbons of FS1 and FS2 are covalently bonded to PP via a C—O bond, the C1-carbon of FS2 is covalently bonded to NB via a C—N bond, and the C1-carbon of FS1 is covalently bonded to AM via L.

In other embodiments, a compound of Formula I is a compound of Formula IB:

AM-FS1-PP-FS2-NB   (IB), or a salt thereof,
wherein
AM is an aromatic chromophore;
FS1 and FS2 are furanose moieties;
PP is a monophosphate, diphosphate, or triphosphate; and
NB is a nucleobase;
wherein the C5-carbons of FS1 and FS2 are covalently bonded to PP via a C—O bond, the C1-carbon of FS2 is covalently bonded to NB via a C—N bond, and the C1-carbon of FS1 is covalently bonded to AM via a C—O bond.

In further embodiments, the linker (L) is O (oxygen), carbamoyl, coupling products of ethylene glycol, a poly (ethyleneglycol), a carbonate, a quinone methide (e.g., methylenecyclohexanone), a chromanone (e.g., 4,4-dialkylchroman-2-one), or a combination thereof. In yet other embodiments, L is: O; S;

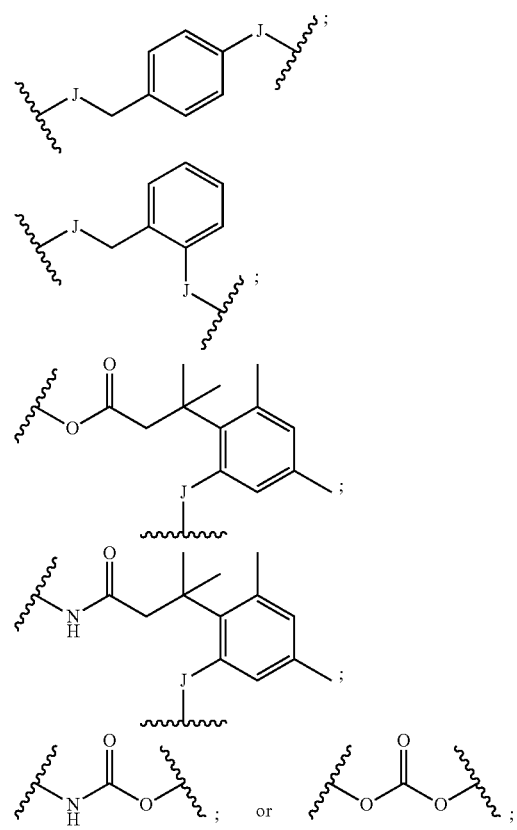

wherein each J is independently O, —N(C═O)O—, or —O(C═O)O— (with the proviso that, in some embodiments, the nitrogen atom of the linker is covalently bonded to AM).

In various other embodiments, the aromatic chromophore is an aromatic fluorophore. In some embodiments, the aromatic fluorophore is an acridine, fluorescein, coumarin, or quinazoline. In some additional embodiments, the aromatic fluorophore is:

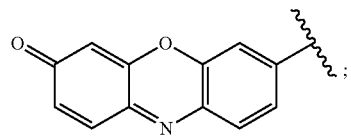

-continued

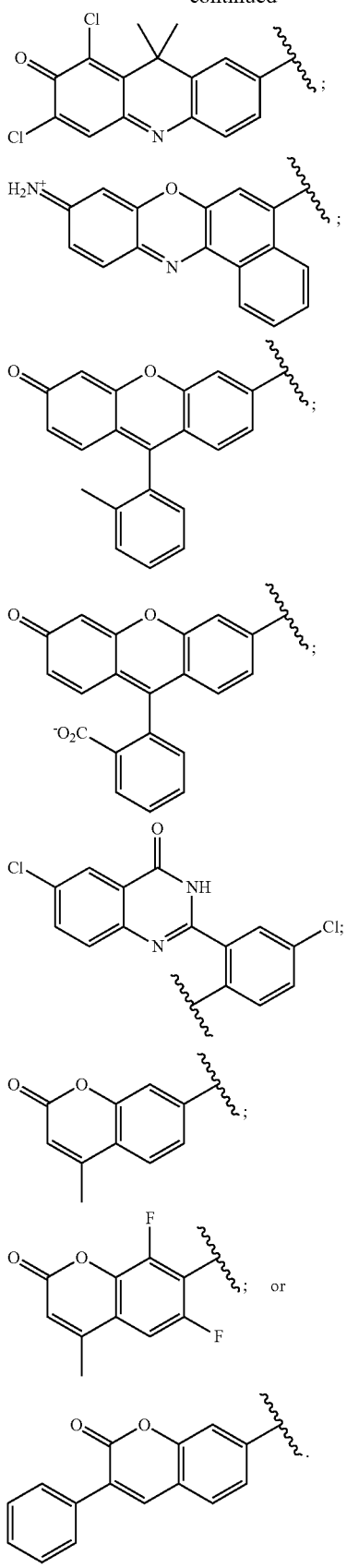

In additional embodiments, AM is Formula A1:

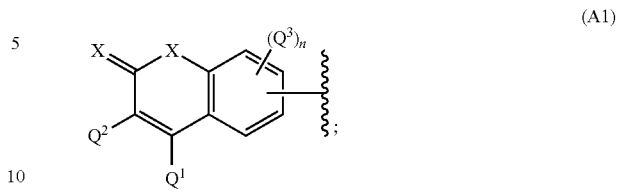

(A1)

wherein
Q¹ and Q² are each independently H, halo, carboxyl, sulfonyl, nitro, aryl, branched or unbranched ($C_1$-$C_6$) alkyl;
Q³ is H or halo;
each X is independently $NR^A$, O, or S; and
$R^A$ is H, or branched or unbranched ($C_1$-$C_6$)alkyl; and
n is 1-3;
wherein aryl and each ($C_1$-$C_6$)alkyl are optionally substituted.

In some additional embodiments, AM is Formula AX:

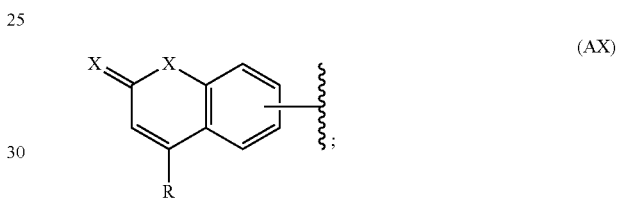

(AX)

wherein
R is a halo, carboxyl, sulfonyl, nitro, aryl, branched or unbranched ($C_1$-$C_6$)alkyl;
each X is independently $NR^A$, O, or S; and
$R^A$ is H, or branched or unbranched ($C_1$-$C_6$)alkyl;
wherein aryl and each ($C_1$-$C_6$)alkyl are optionally substituted.

In some embodiments, ($C_1$-$C_6$)alkyl is substituted with 1-5 substituents, such as halo. In some specific embodiments, ($C_1$-$C_6$)alkyl is —$CF_3$, $CF_2H$, or $CF_2CF_3$.

In other additional embodiments, Formula A1 is A:

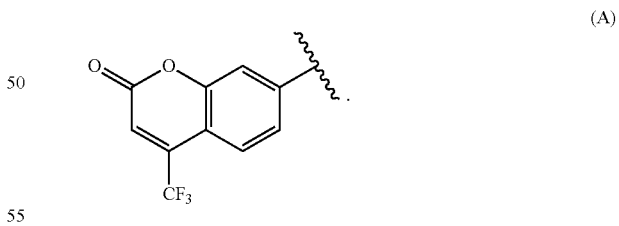

(A)

In some embodiments, AM is Formula A2:

(A2)

wherein R$^1$ and R$^2$ are each independently halo, carboxyl, sulfonyl, nitro, aryl, branched or unbranched (C$_1$-C$_6$) alkyl; and wherein aryl and (C$_1$-C$_6$)alkyl are optionally substituted.

In other embodiments, Formula A2 is para-nitrophenyl.

In further embodiments, FS1 and FS2 are Formula FX:

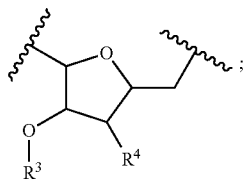  (FX)

wherein
R$^3$ is H or branched or unbranched (C$_1$-C$_6$)alkyl;
R$^4$ is H or OR$^x$; and
R$^x$ is H or branched or unbranched (C$_1$-C$_6$)alkyl.

In some other embodiments, R$^3$ is H and R$^4$ is OH.

In yet other embodiments, NB is Formula N1:

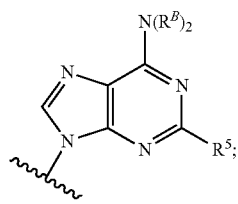  (N1)

wherein
R$^5$ is H or N(R$^B$)$_2$; and
each R$^B$ is independently H, or branched or unbranched (C$_1$-C$_6$)alkyl.

In some various other embodiments, R$^5$ is H and each R$^B$ on nitrogen is H.

In further embodiments, NB is Formula N2:

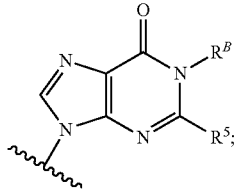  (N2)

wherein
R$^5$ is H or N(R$^B$)$_2$; and
each R$^B$ is independently H, or branched or unbranched (C$_1$-C$_6$)alkyl.

In other embodiments, PP is P1:

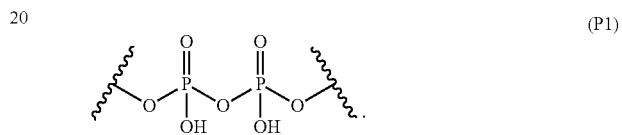  (P1)

In various additional embodiments, the compound of Formula I is a compound of Formula II:

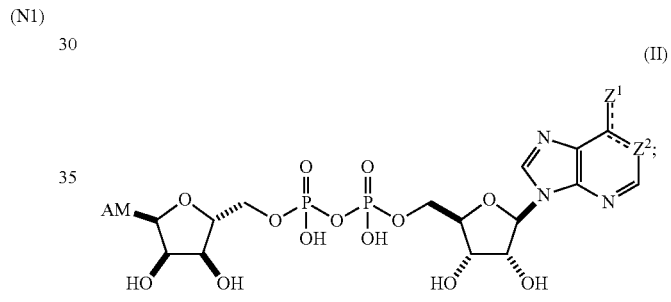  (II)

wherein
------ is a single or double bond; and
Z$^1$ is O and Z$^2$ is NH, wherein ------ on Z$^1$ is a double bond and ------ on Z$^2$ is a single bond; or
Z$^1$ is NH$_2$ and Z$^2$ is N, wherein ------ on Z$^1$ is a single bond and ------ on Z$^2$ is a double bond.

In yet other embodiments, the compound is:

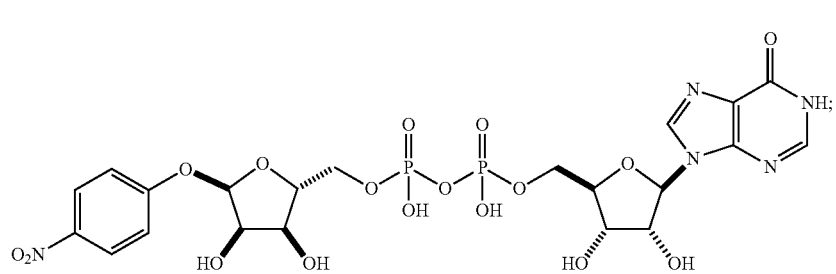  (1)

-continued

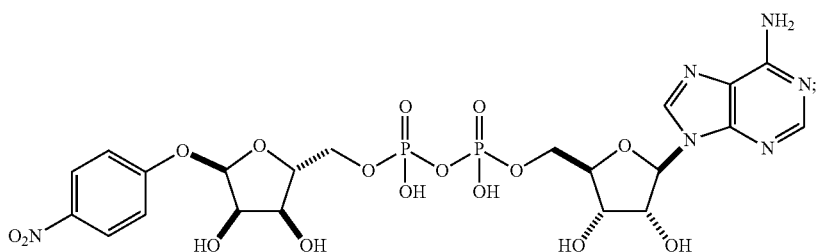

(2)

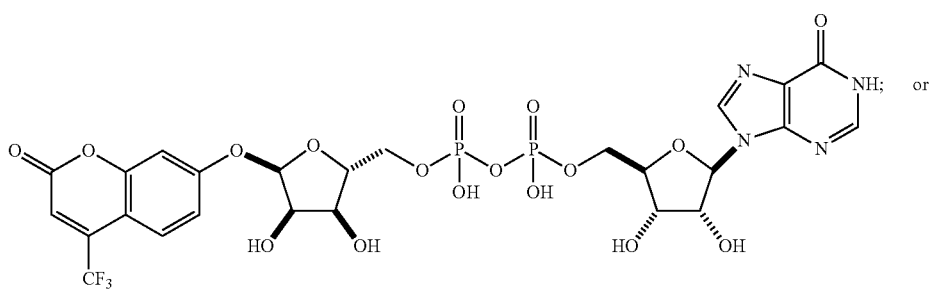

(3)

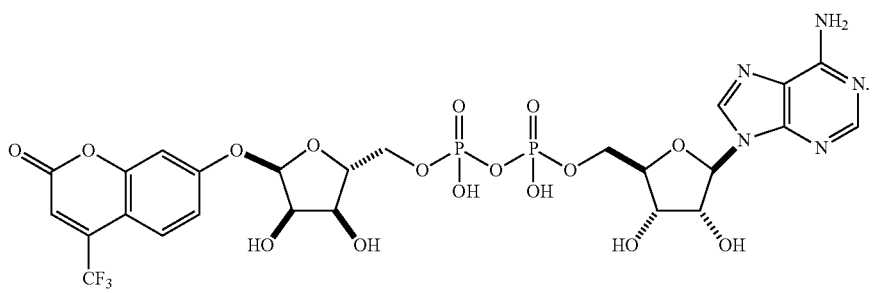

(4)

This disclosure also provides various embodiments of a compound of Formula III:

AA-FS1-PP-FS2-NB    (III);

or a salt thereof,
wherein
  AA is an amino acid;
  FS1 and FS2 are furanose moieties;
  PP is a monophosphate, diphosphate, or triphosphate; and
  NB is a nucleobase;
  wherein the C5-carbons of FS1 and FS2 are covalently bonded to PP via a C—O bond, the C1-carbon of FS2 is covalently bonded to NB via a C—N bond, and the C1-carbon of FS1 is covalently bonded to AA via a C—N bond;
  with the proviso that AA is not arginine when NB is adenine and PP is diphosphate. In some embodiments, the compound of Formula III is a compound of Formula IV:

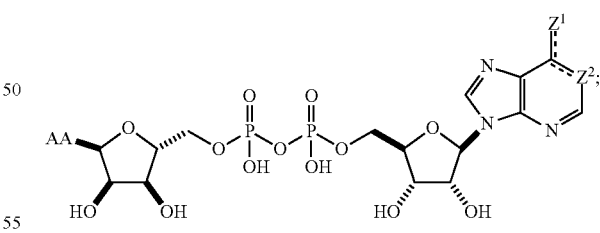

(IV)

wherein
  ------ is a single or double bond; and
  $Z^1$ is O and $Z^2$ is NH, wherein ------ on $Z^1$ is a double bond and ------ on $Z^2$ is a single bond; or
  $Z^1$ is $NH_2$ and $Z^2$ is N, wherein ------ on $Z^1$ is a single bond and ------ on $Z^2$ is a double bond.

In other additional embodiments, the compound is an inhibitor of ADP-ribosylhydrolase 3 (ARH3) or poly(ADP-ribose) glycohydrolase (PARG).

In yet other embodiments, the compound is:

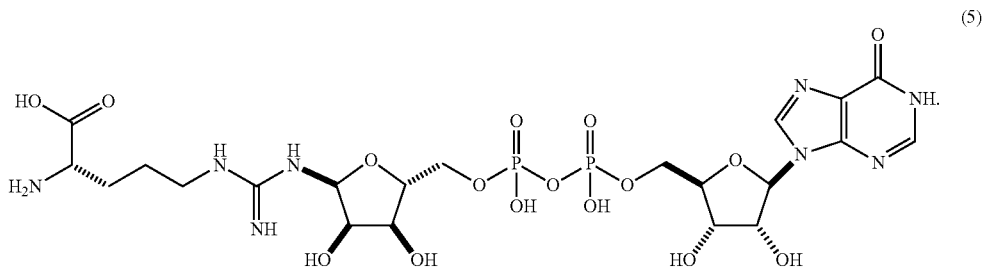

(5)

Additionally, this disclosure provides embodiments of a method of detecting poly(ADP-ribose) (PAR) cellular activity comprising:
a) contacting a compound described above and constituents of a cell or a whole cell lysate to form a mixture; and
b) detecting changes in fluorescence in the mixture;
wherein: the compound is a substrate of poly(ADP-ribose) glycohydrolase (PARG), and PARG selectively hydrolyses the compound to release the AM moiety as AM-OH;
the compound is a substrate of ADP-ribosylhydrolase 3 (ARH3), and ARH3 selectively hydrolyses the compound to release the AM moiety as AM-OH;
or a combination thereof; wherein AM-OH is fluorescent and an increase in fluorescence indicates PAR cellular activity.

In some embodiments, the constituents of a cell are from a whole-cell lysate. In other embodiments, the whole-cell lysate is a whole-cell lysate of cancer cells. In additional embodiments, PAR cellular activity is continuously interrogated by monitoring changes in fluorescence. In further embodiments, the kinetics of PAR cellular activity are measured by changes in fluorescence. In yet other embodiments, an increase in fluorescence further indicates PAR degrading activity.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion

Design and Synthesis of PARG Substrates

Reporter substrates for PARG and ARH3, pNP-ADPr and TFMU-ADPr, were designed, inspired by the natural substrate, PAR. The 2',1"-glycosidic bond that is cleaved in PAR (shown in Scheme 1A) was replaced with a phenolic glycoside. Initial efforts focused on utilizing 4-nitrophenol (pNP) as a chromaphore reporter but also extended to the fluorophore 4-(trifluoromethyl)umbelliferone (TFMU) for applications requiring greater sensitivity and specificity. Retrosynthetic analysis of pNP-ADPr identified two major synthetic hurdles (Scheme 1B): a late-stage pyrophosphate coupling and a 1,2-cis selective glycosylation of a furanoside. Recent work on the synthesis of dimeric PAR (J. Am. Chem. Soc. 2015, 137, 3558) overcame similar challenges, and it was envisioned that an analogous strategy could be applied to the synthesis of this simplified PARG substrate.

TABLE 1

Docking scores for sugar nucleotides in PARG and ARH3. See FIG. 1.

| Enzyme | Ligand | SP score (kcal/mol) | SP Difference (kcal/mol) | XP score (kcal/mol) | XP difference (kcal/mol) |
|---|---|---|---|---|---|
| L. chalumnae ARH3 | ADPr | −7.539 | — | −6.254 | — |
| | IDPr | −6.729 | 0.810 | −7.000 | −0.746 |
| | GDPr | −6.692 | 0.847 | −6.131 | 0.123 |
| | XDPr | −7.100 | 0.439 | −6.732 | −0.478 |
| H. sapiens PARG | ADPr | −12.229 | — | −8.262 | — |
| | IDPr | −10.332 | 1.897 | −6.613 | 1.649 |
| | GDPr | −10.906 | 1.323 | −6.323 | 1.939 |
| | XDPr | −11.292 | 0.937 | −6.090 | 2.172 |

Scheme 1. Design of PARG/ARH3 substrate. A. PAR is cleaved by PARG and ARH3 via hydrolysis of the glycosyl bond (arrow). B. Synthetic PARG/ARH3 substrates mimic ADP-ribose and release a chromophore or fluorophore upon hydrolysis. Synthesis of these compounds requires a late-stage pyrophosphate formation and 1,2-cis selective glycosylation.

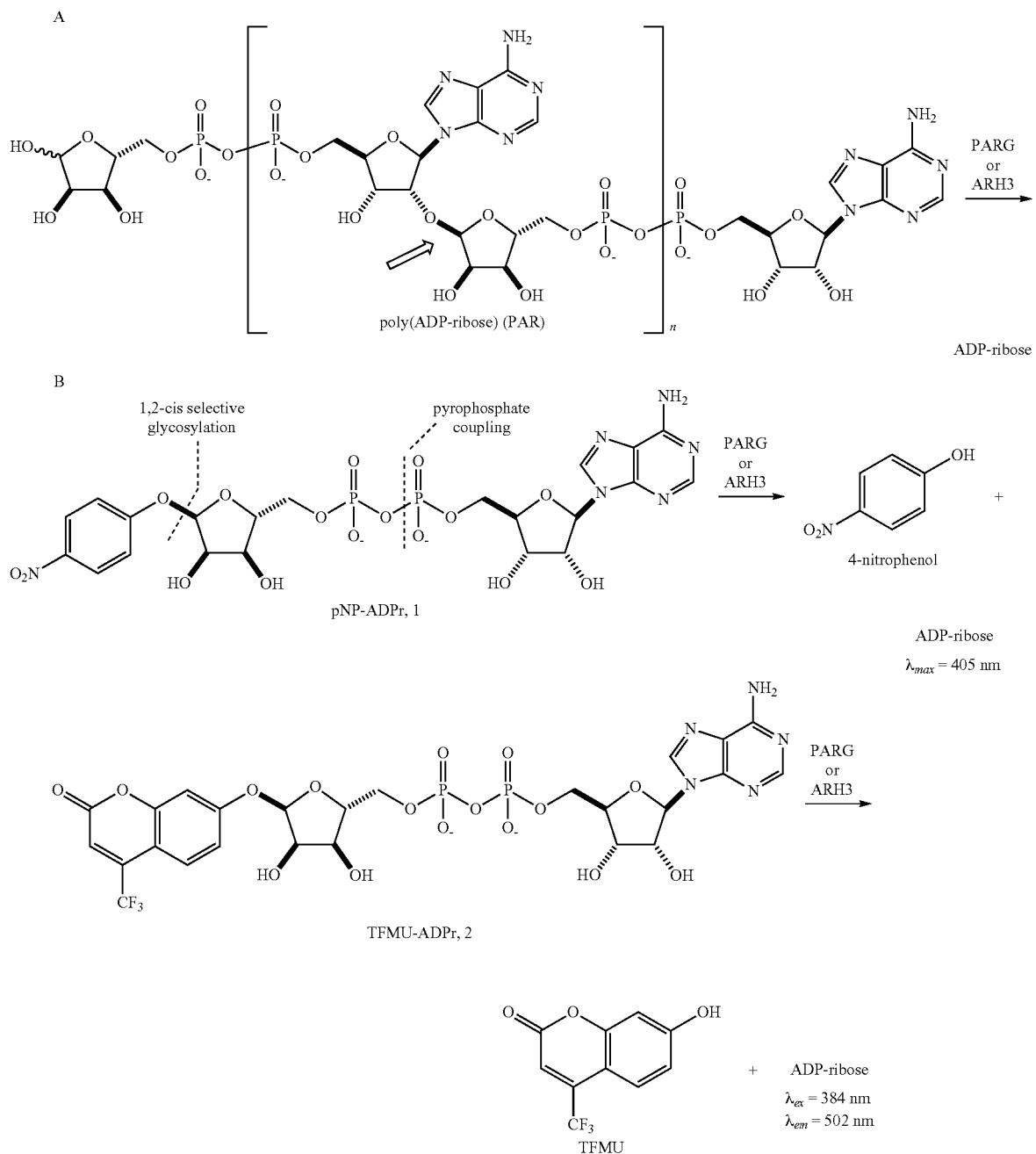

Glycosylation of electron-deficient phenols such as pNP and TFMU is often challenging. Most methods rely of anchimeric assistance leading to the undesired 1,2-trans product. It was found that acceptable α-selectivity could be achieved by directly activating a hemi-acetal with bulky protecting groups under Mitsunobu conditions. As outlined in Scheme 2, this strategy was employed using orthogonally protected ribose 3, prepared in three steps from D-ribonic γ-lactone (Scheme 4A); subsequent removal of the trityl group proceeded smoothly under strictly anhydrous conditions to prevent hydrolysis of the glycoside, producing 4 and 5. Although direct phosphorylation with $POCl_3$ was possible, it was found that phosphoramidite coupling followed by fluorenylmethyl removal more amenable on scale to give phosphates 6 and 7 (Scheme 2, Scheme 4B, 4C). Pyrophosphate formation was accomplished via in situ oxidative chlorination of H-phosphonate 8 (Scheme 2, Scheme 4D), to produce 9 and 10, followed by global desilylation to provide pNP-ADPr and TFMU-ADPr.

Scheme 2. Synthesis of pNP-ADPr and TFMU-ADPr. Abbreviations: ADDP = 1,1'-(azodicarbonyl)
dipiperidine, DIAD = diisopropyl azodicarboxylate, Fm = 9H-fluorenylmethyl, DCI = 4,5-dicyanoimidazole,
NCS = N-chlorosuccinimide, DBU = 1,8-diazabicycloundec-7-ene, TBS = tertbutyldimethylsilyl.

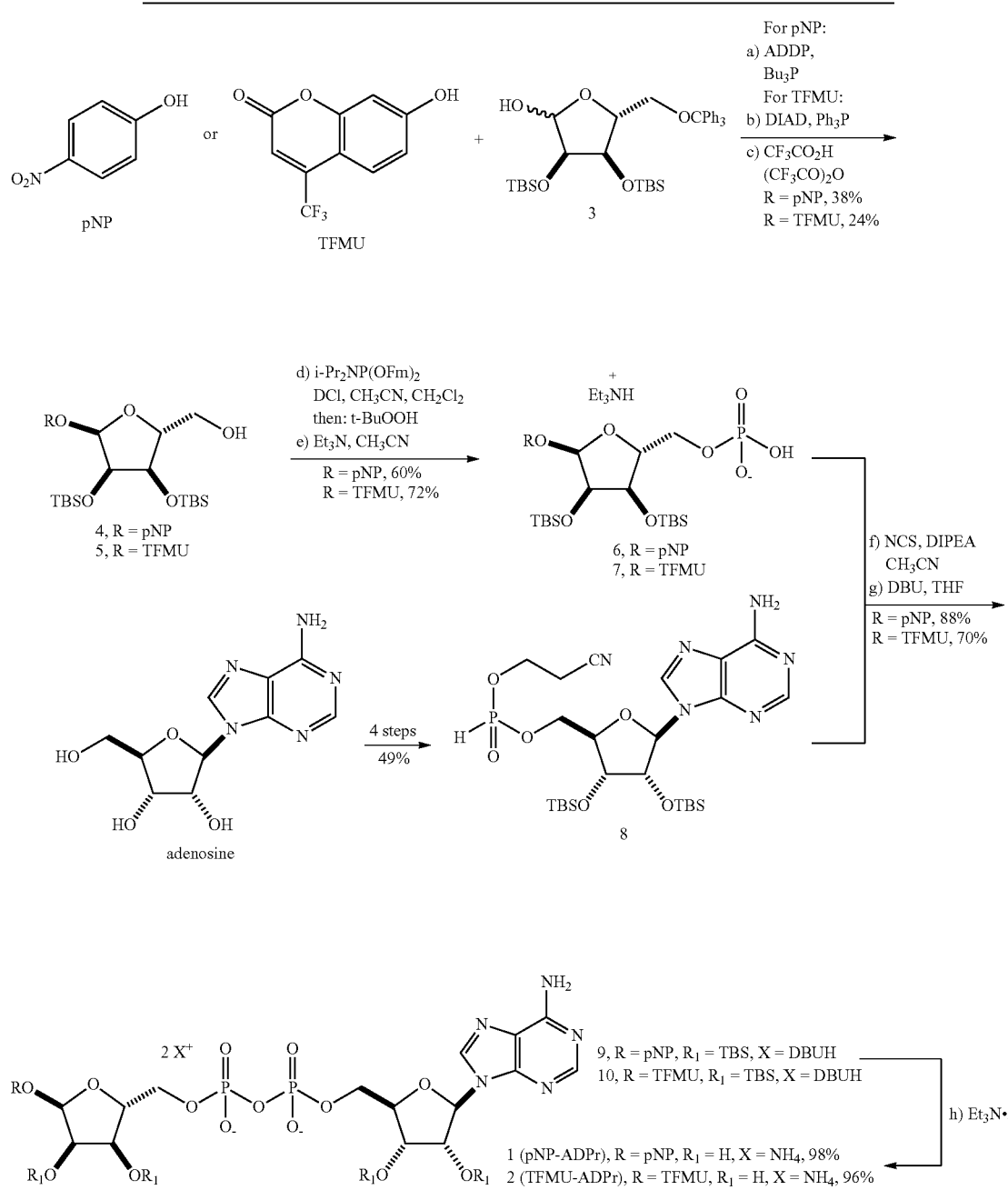

The late-stage pyrophosphate coupling featured in the synthesis of these compounds also facilitates the construction of other non-natural substrates for PARG. The recently co-crystalized structure of *L. chalumnae* ARH3 with ADPr (not shown, co-submitted) indicates that the binding modes of hPARG and LchARH3 are dramatically different. In particular, the adenine binding site of LchARH3 is much less organized and more solvent exposed.

Molecular docking sugar nucleotides with varied purine bases suggests that PARG is highly discriminatory while ARH3 would accommodate other bases (Table 1). Key interactions between ADPr and hPARG Glu727 and Ile726 cannot be recapitulated with IDPr, and the hPARG binding site is too restrictive to allow for additional favorable interactions (FIG. 1B). Conversely, the LchARH3 binding site is predicted to allow IDPr to shift and make additional interactions with Lys132 (FIG. 1C). It was hypothesized that replacing the nucleobase of phenolic substrates, specifically substitution of adenine for hypoxanthine, would provide a substrate selective for ARH3. Therefore, the compounds TFMU-IDPr and pNP-IDPr were designed and synthesized from inosine (Scheme 3, and Scheme 5).

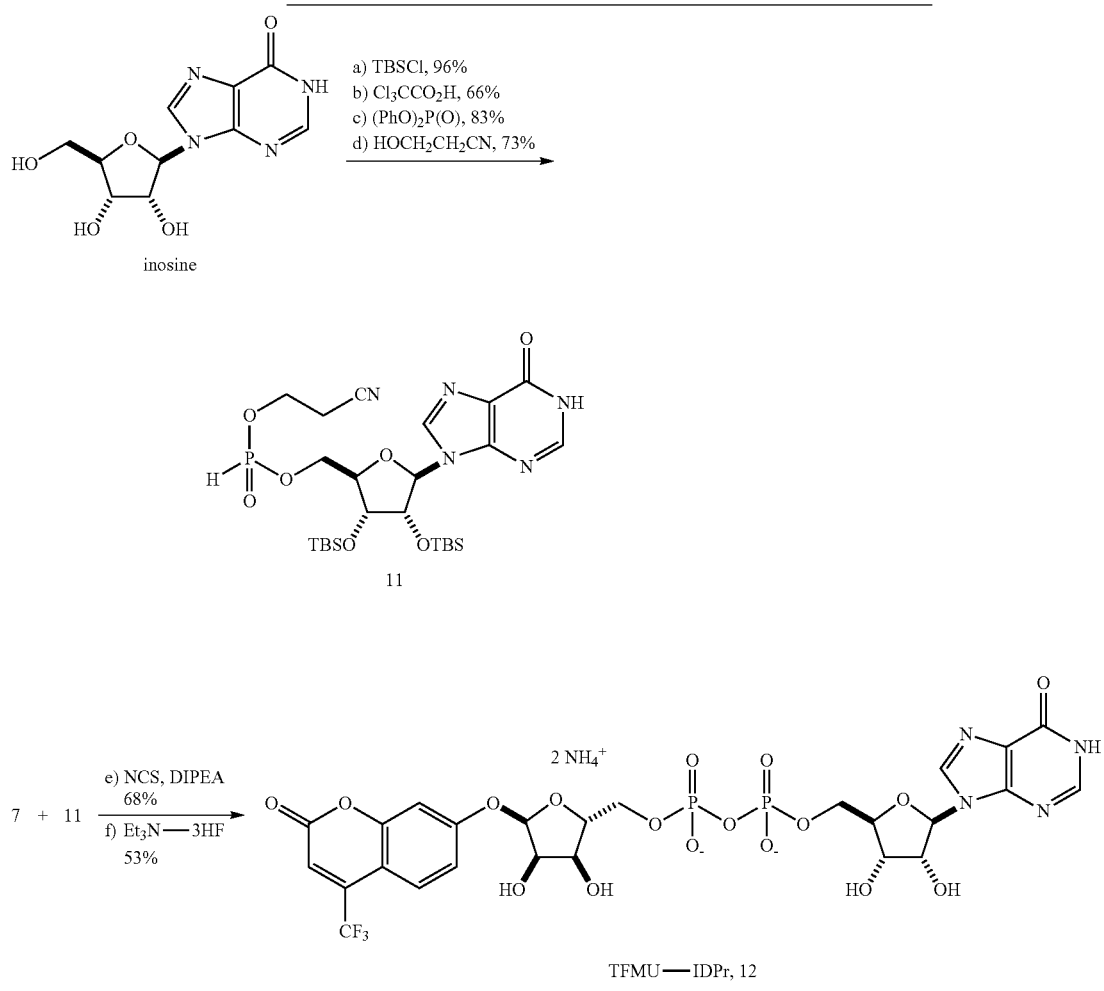

Scheme 3. Synthesis of TFMU—IDPr; for pNP—IDPr synthesis see Scheme 5.

In Vitro Processing of Substrates

Figure 2:
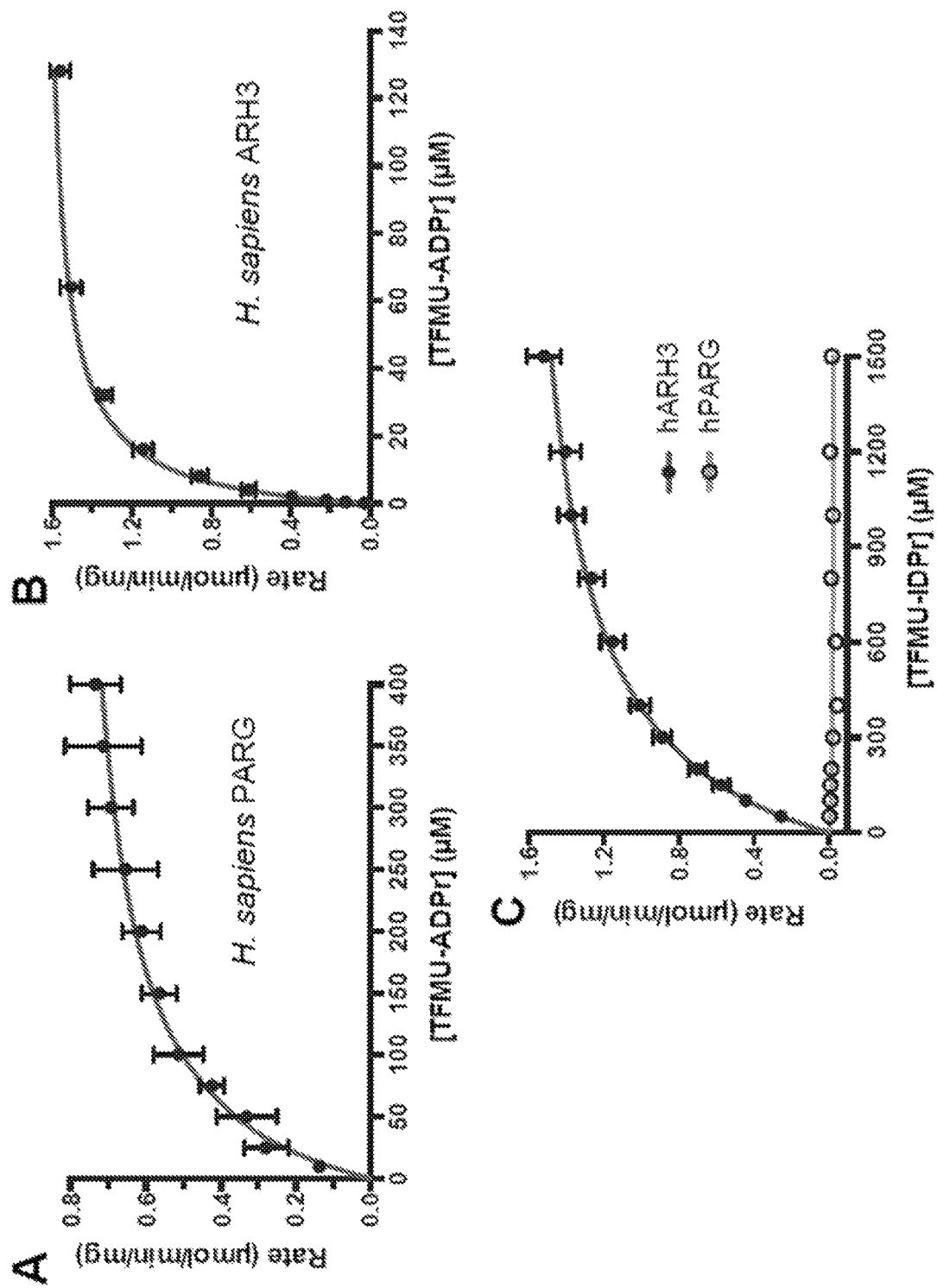
FIG. 2. Michaelis-Menton kinetics of recombinantly expressed human PARG and ARH3. A. Kinetics of human PARG processing TFMU-ADPr. B. Kinetics of human ARH3 processing TFMU-ADPr. C. Selectivity of TFMU-IDPr for processing by human ARH3 over human PARG. Error bars indicate SEM, n=3.
Figure 5:
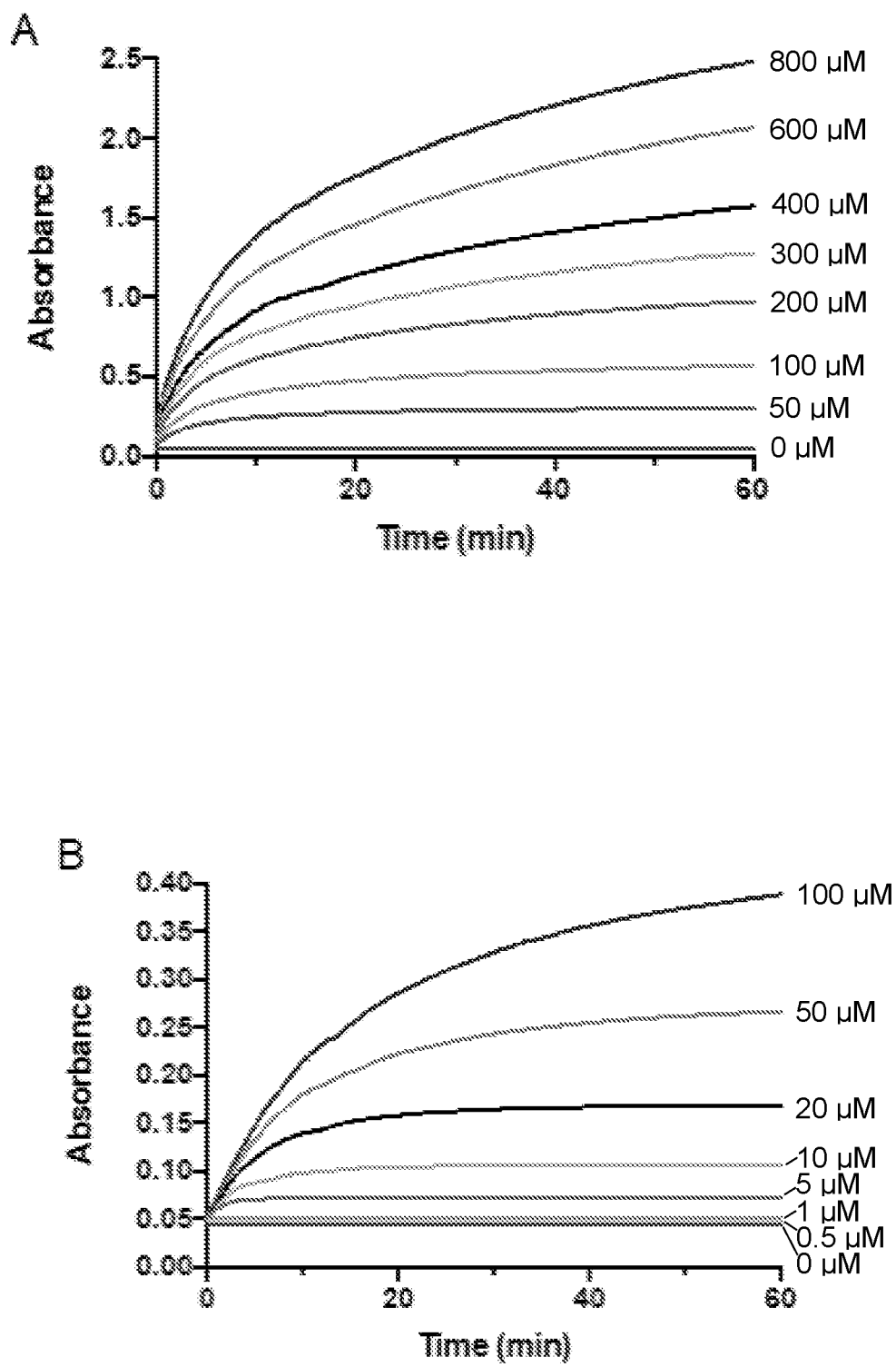
FIG. 5. Related to FIG. 2. A. Reaction progress curves of ttPARG-catalyzed hydrolysis of pNPADPr. Enzyme (50 nM) was incubated with varying concentration of pNP-ADPr in 50 μL of appropriate reaction buffer in a 384-well plate. Reaction was monitored every 2 s for 60 min. B. Same as B but with hARH3. C. Stereoselectivity of PARG and ARH3 for a glycosidic bonds. ttPARG (50 nM) was incubated with varying concentrations of α and β pNP-ADPr in 50 μL of appropriate reaction buffer in a 384-well plate. Initial reaction rates were obtained by monitoring reaction progress using an absorbance plate reader (405 nm). D. Same as C but with hARH3. E. Structures of α and β pNP-ADPr. F. Processing of TFMU-ADPr by catalytically active (WT) and inactive (E756N) hPARG. G. Processing of TFMU-ADPr by catalytically active (WT) and inactive (D77N/D78N) hARH3. Error bars represent SEM, n=3.
Figure 5:
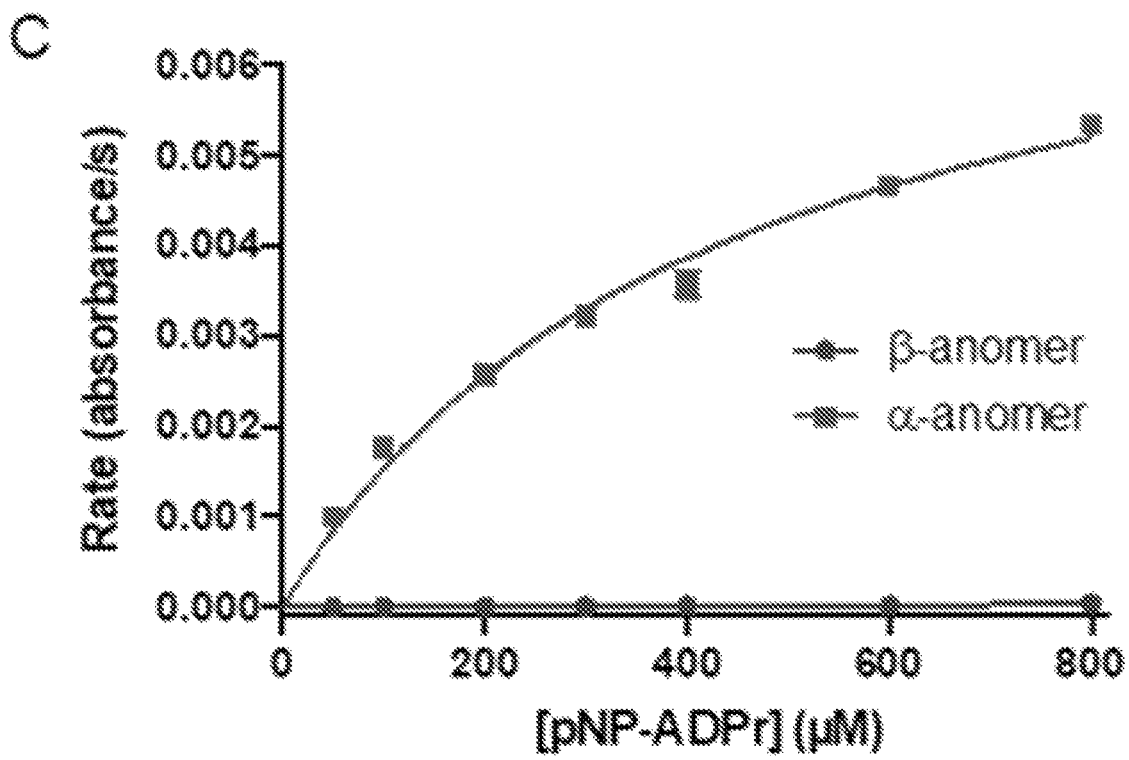
Figure 5:
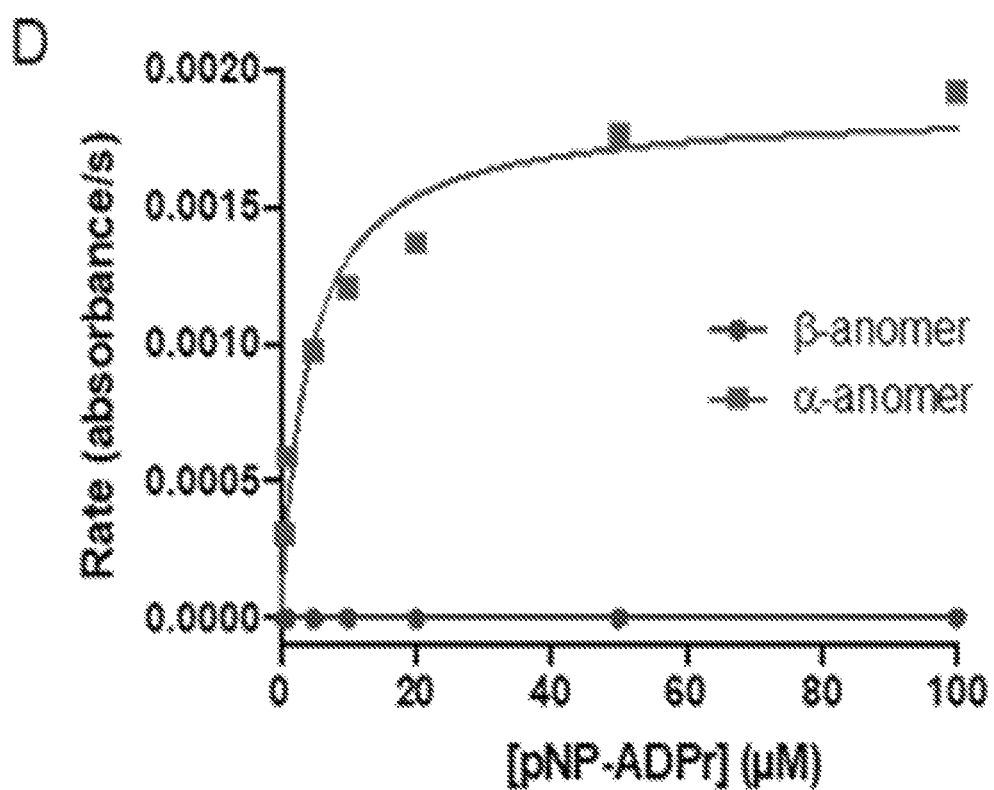
Figure 5:
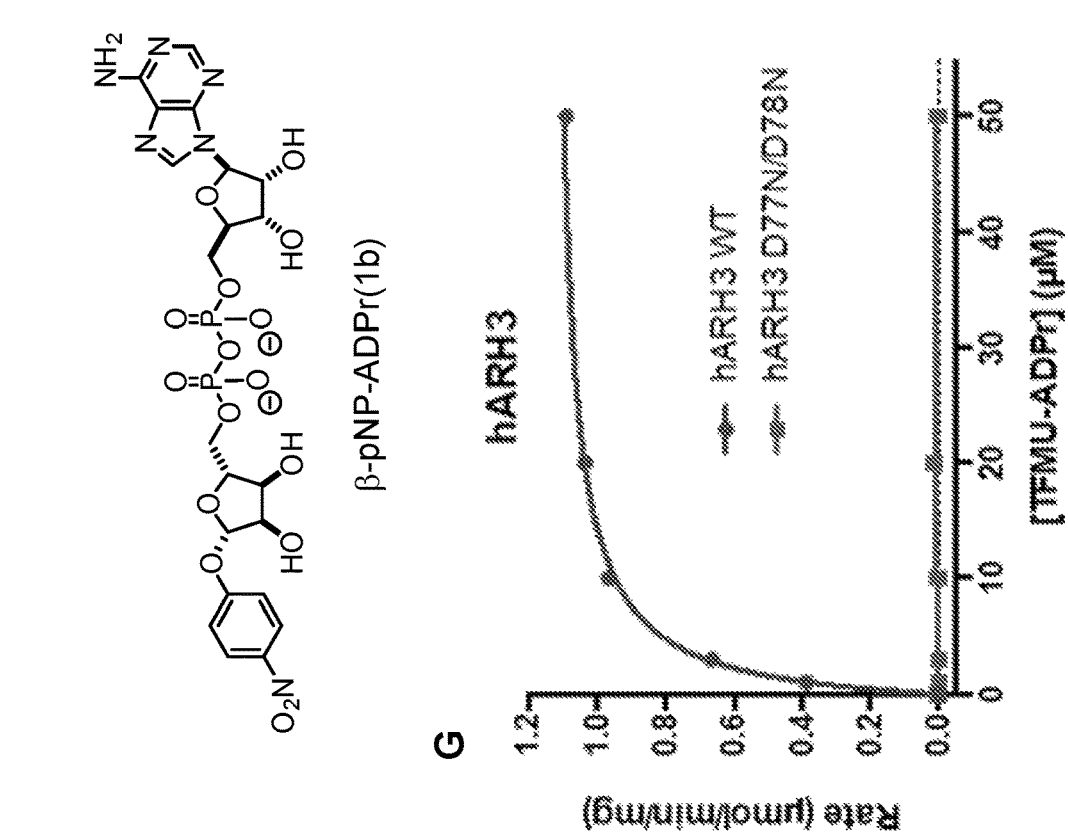
Figure 5:
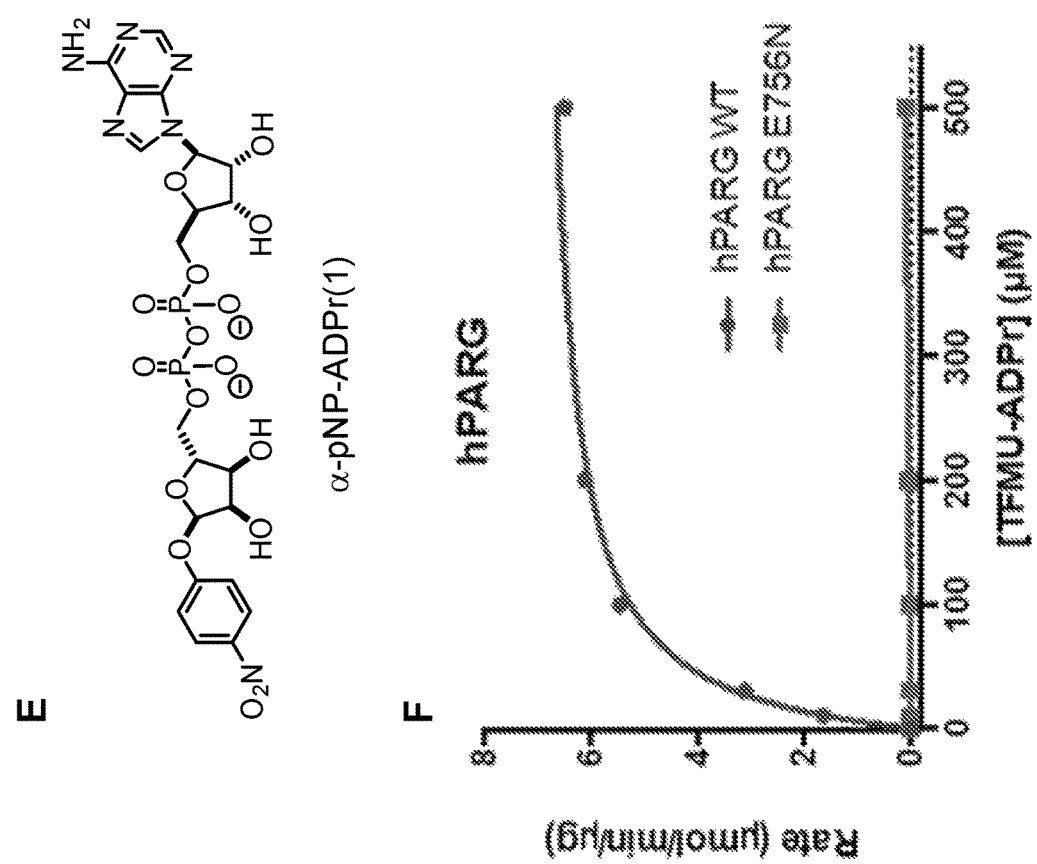
Figure 6:
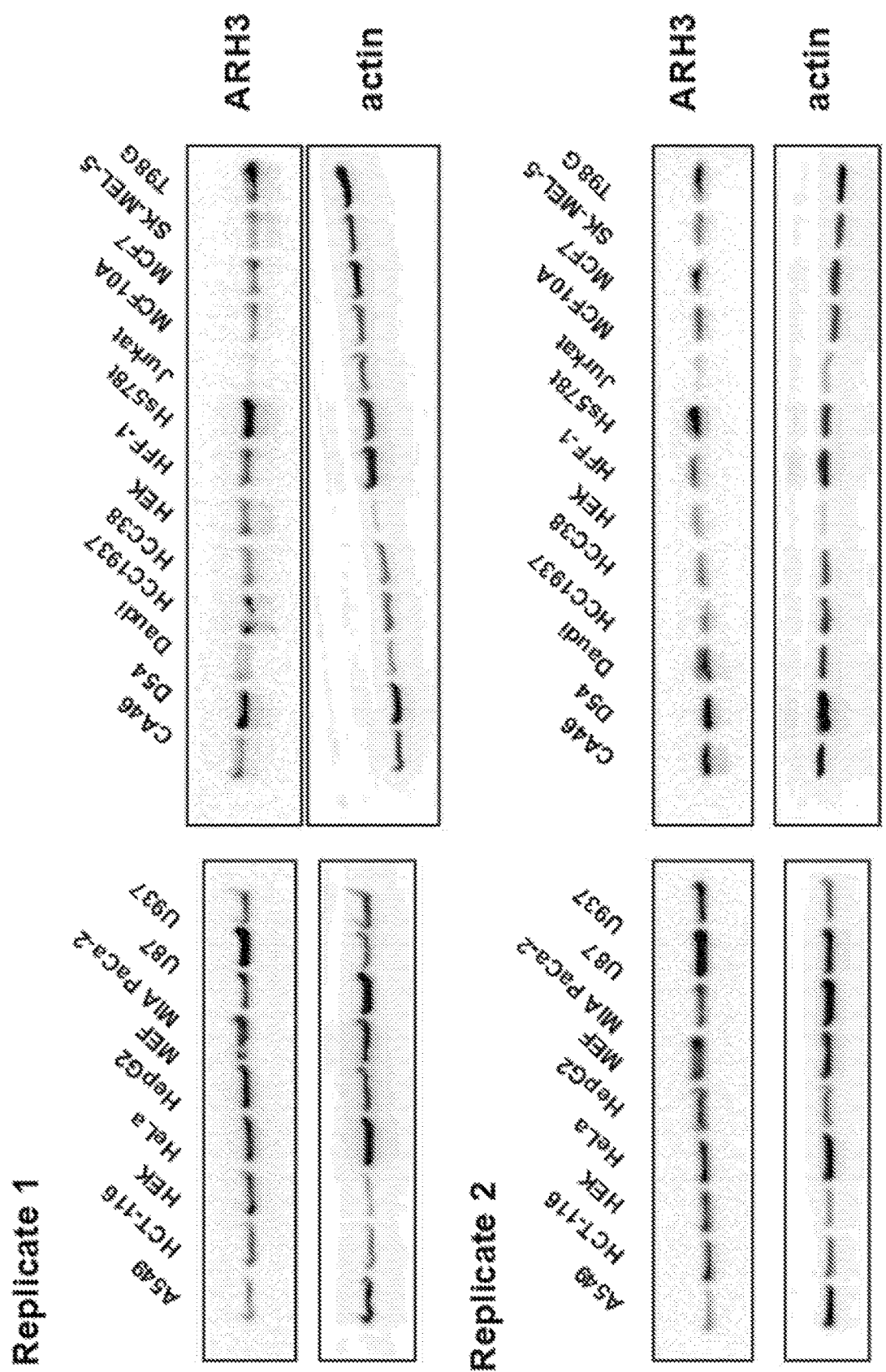
FIG. 6. Related to FIG. 3. Expanded images of Western blotting to evaluate ARH3 expression. Replicate 1 is same as shown in FIG. 3D but without straightening. Anti-ARH3 (1:1000), anti-PARP1 (1:3000), anti-actin (1:3000).

Using pNP-ADPr and TFMU-ADPr, the first continuous PARG and ARH3 activity assays were developed. Enzymatic hydrolysis of phenolic glycosides was easily monitored by an increased absorbance or fluorescence (FIG. 5A, B). Kinetic parameters for human PARG and ARH3 were determined by non-linear fitting of initial reaction rates (Table 2 and FIG. 2A, B). A commonly used ortholog of PARG from $T.$ $thermophila$ (ttPARG) was also characterized and found to effectively hydrolyze pNP-ADPr and TFMU-ADPr (Table 2 and FIG. 5A). The measured KM of ARH3 was similar to the enzyme's reported activity against O-acetyl-ADP-ribose. The kinetic parameters of pNP-ADPr and TFMU-ADPr were quite similar likely due to the leaving groups having similar $pK_a$s (7.15 and 7.26). Gratifyingly, the predicted selectivity of TFMU-IDPr for ARH3 over PARG was confirmed (FIG. 2C). Further, both PARG and ARH3 selectively hydrolyzed the α anomer of pNP-ADPr over the β anomer as is consistent with their natural substrates (FIG. 5C, D). Hydrolysis of substrates depends on catalytically active protein; inactivating mutations in hPARG (the E756N mutant, and hARH3 (the D77N/D78N mutant, abolish substrate processing (FIG. 5F, G).

TABLE 2

Kinetic parameters derived for ADP-ribosylhydrolase substrates.

| Substrate | Enzyme | $K_M$ (μM) | $V_{max}$ (μmol/min/mg) |
|---|---|---|---|
| TFMU-ADPr | hPARG[a] | 66.2 ± 15 | 0.84 ± 0.05 |
|  | ttPARG[b] | 210 ± 13 | 28.6 ± 0.6 |
|  | hARH3[c] | 6.3 ± 0.2 | 1.61 ± 0.02 |
| TFMU-IDPr | hPARG | >1500 | n.d. |
|  | ttPARG | >1500 | n.d. |
|  | hARH3 | 312 ± 30 | 1.79 ± 0.06 |
| pNP-ADPr | ttPARG | 210 ± 10 | 16.9 ± 0.5 |
|  | hARH3 | 3.2 ± 0.6 | 1.7 ± 0.1 |
| pNP-IDPr | ttPARG | >1500 | n.d. |
|  | hARH3 | 410 ± 20 | 5.2 ± 0.2 |

ADPr, adenine diphosphate ribose;
ARH3, ADP-ribosyl hydrolase 3;
IDPr, inosine diphosphate ribose;
n.d., not determined;
PARG, poly(ADPribose) glycohydrolase;
pNP, 4-nitrophenol;
TFMU, fluorophore 4-(trifluoromethyl)umbelliferone.
[a]$H.$ $sapiens$ full length PARG
[b]$T.$ $thermophila$ PARG
[c]$H.$ $sapiens$ full length ARH3

Use of Substrates to Monitor ARH3 Activity Assay in Cell Culture

Figure 3:
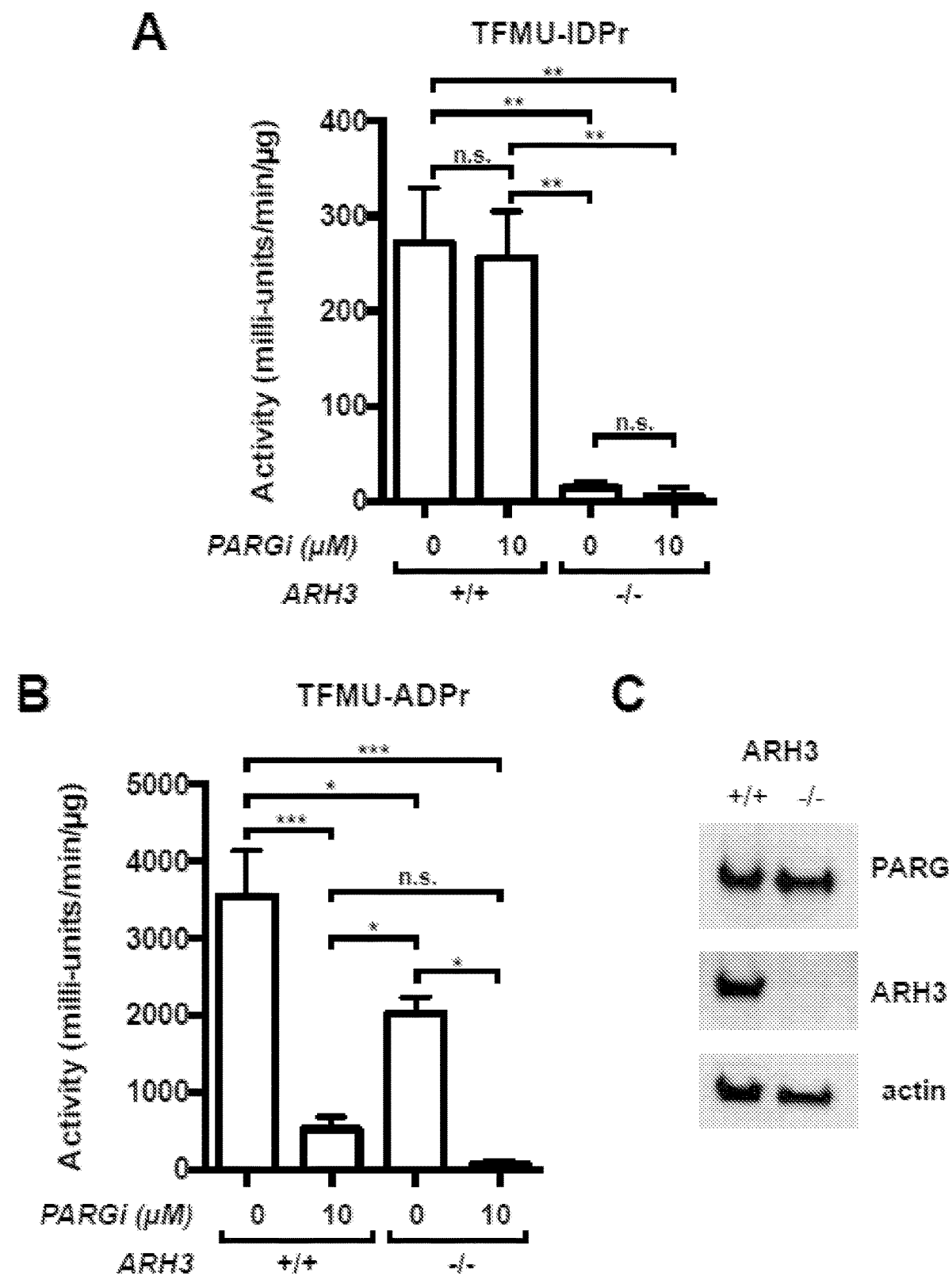
FIG. 3. Measurement of PARG activity in cell lysate and validation of TFMU-IDPr selectivity. A. Selectivity for ARH3 by TFMU-IDPr validated by CRISPR-Cas9 knock-out of ARH3 in U2OS cells. PARG activity was measured in the presence and absence of PARG inhibitor PDD00017273 using TFMU-IDPr at 200 μM. Error bars indicated SEM, n=3. Significance levels are given by asterisks: $p<0.05$ (*), $p<0.01$ (), $p<0.001$ (*), $p>0.05$ (n.s.). B. Same as A but with 200 μM TFMU-ADPr. C. Validation of ARH3 knock-out in U2OS as measured by Western blotting. D. Western blotting to determine ARH3 expression levels in various indicated cell lines; representative blot of two independent replicates shown, see FIG. 6 for all replicates. E. Correlation of ARH3 expression (measured by Western blotting) with ARH3 activity (measured by TFMU-IDPr hydrolysis). Data points reflect average values from different mammalian cell lines. Circle point on x-axis indicates MCF10A. ARH3 activity was measured with 200 μM TFMU-IDPr.
Figure 3:
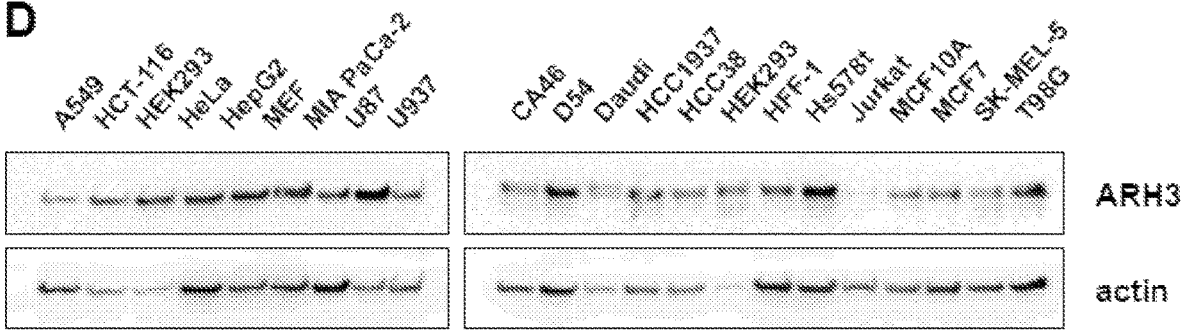
Figure 3:
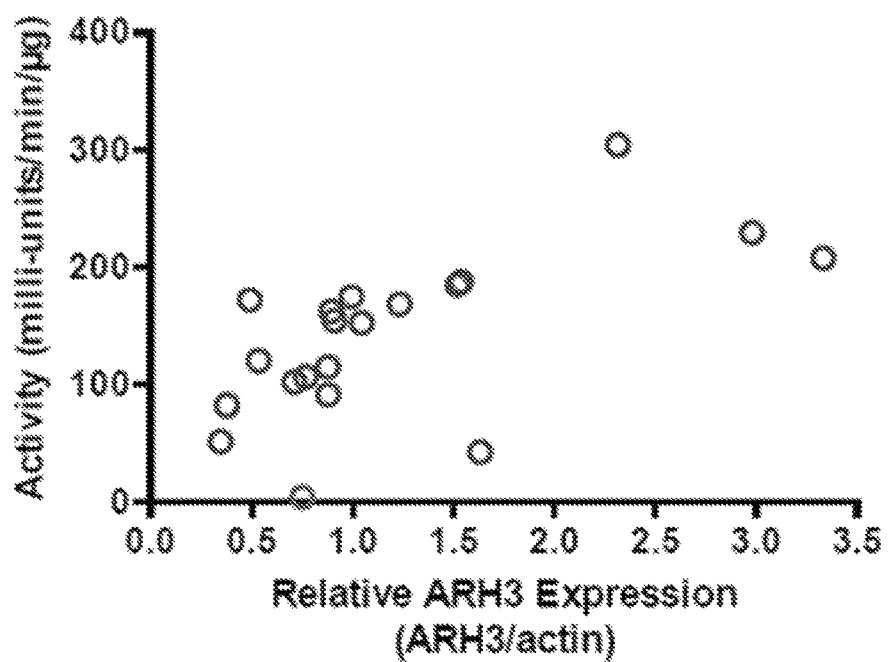

The ability of TFMU-IDPr to selectively report on ARH3 activity within the cellular milieu would be an important application of these probes. While the experiments in FIG. 2 demonstrate the selectivity of this substrate for ARH3 over PARG in a purified enzymatic system, in cells other hydrolases that recognize ADP-ribose could potentially process this substrate, thus two experiments were conducted to assess the activity of ARH3 and PARG with these substrates in cell lysate. First, the hydrolysis of TFMU-IDPr was evaluated in cell lysate from a ARH3 knockout isogenic cell line pair derived from U2OS cells. Knockout of ARH3 resulted in near complete loss of TFMU-IDPr activity (FIG. 3A) while TFMU-ADPr hydrolysis was only partially decreased (FIG. 3B). Second, substrate processing was evaluated in the presence of the selective PARG inhibitor PDD00017273. Hydrolysis of TFMU-ADPr was completely abolished by PDD00017273 in ARH3$^{-/-}$ cell lysate, but TFMU-IDPr was unaffected by PARG inhibitor. Taken together, these experiments indicate that TFMU-IDPr is selectively cleaved by ARH3 in cell lysate, and TFMU-ADPr is cleaved only by ARH3 and PARG.

Survey of Cancer Cell Lines

As the activity of ARH3 in various cell types is unknown, experiments were conducted to assess ARH3 activity in a variety of cancer cell lines. Twenty cell lines were analyzed for ARH3 activity, measured using TFMU-IDPr, and compared to ARH3 abundance (measured by Western blot, FIG. 3D); in general, ARH3 activity and abundance are well correlated (FIG. 3E, Table 3). Strikingly, no ARH3 activity is observed with MCF10A cells despite the obvious presence of ARH3 by Western blot. Thus, it was hypothesized that in this cell line ARH3 is mutated or being affected by an endogenous inhibitor.

Figure 7:
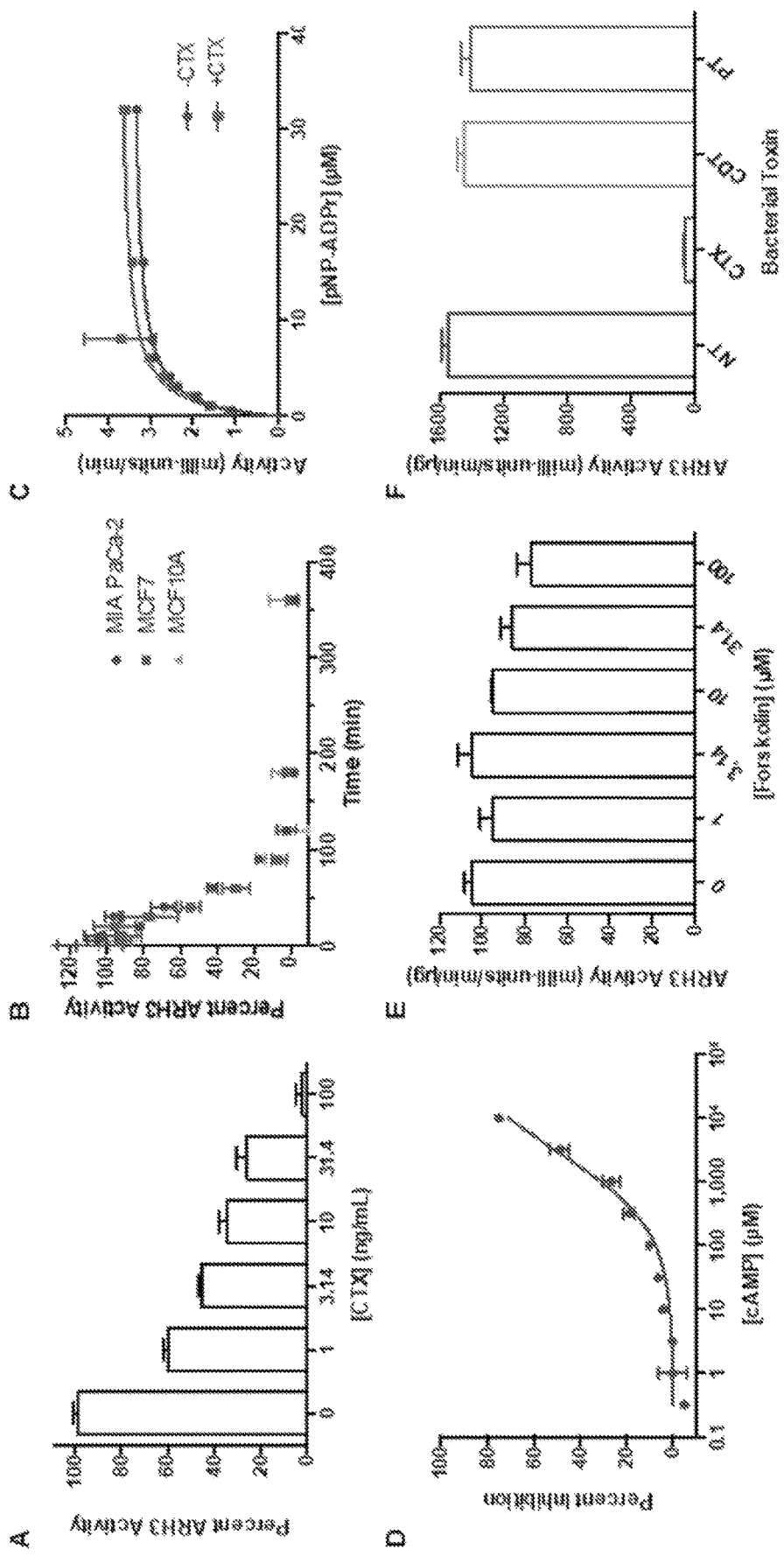
FIG. 7. Related to FIG. 4. A. MCF10A cells were cultured in the absence of CTX for five passages. Cells were plated 1×105 cells/well in 6-well plate. Cells were treated with varied concentration of CTX for 48 h. Remaining ARH3 activity was measured with 200 μM TFMU-IDPr. B. Cells were plated 3×105 cells/well in 6-well plate. Cells were treated with 100 ng/mL CTX for the indicated period of time. Remaining ARH3 activity was measured with 200 μM TFMU-IDPr. C. In vitro activity of purified ARH3 in the presence or absence of 100 ng/mL CTX. D. Dose-response curve of ARH3 inhibition by cAMP using 200 μM TFMU-IDPr. E. MCF10A cells treated with forskolin for 1 h. F. A549 cells treated with various bacterial toxins for 24 h. Following treatment, ARH3 activity in cell lysate was assessed. CTX, cholera toxin 100 ng/mL; CDT, *C. difficile* toxin 200 ng/mL CDTa 400 ng/mL CDTb; PT, pertussis toxin 100 ng/mL. G. Metabolic profiling of MCF7 cells treated with 100 ng/mL CTX for 6 h. Metabolites (ADPr-Arg, cAMP, ADP-ribose, $NAD^+$, and arginine) in methanolic cell extract were quantified by LC-MS/MS. Samples below the limit of detection are indicated by open points. Error bars represent standard deviation, n=6. P values are from unpaired t-test with Welch's correction H. Same as G but with U2OS cells.
Figure 7:
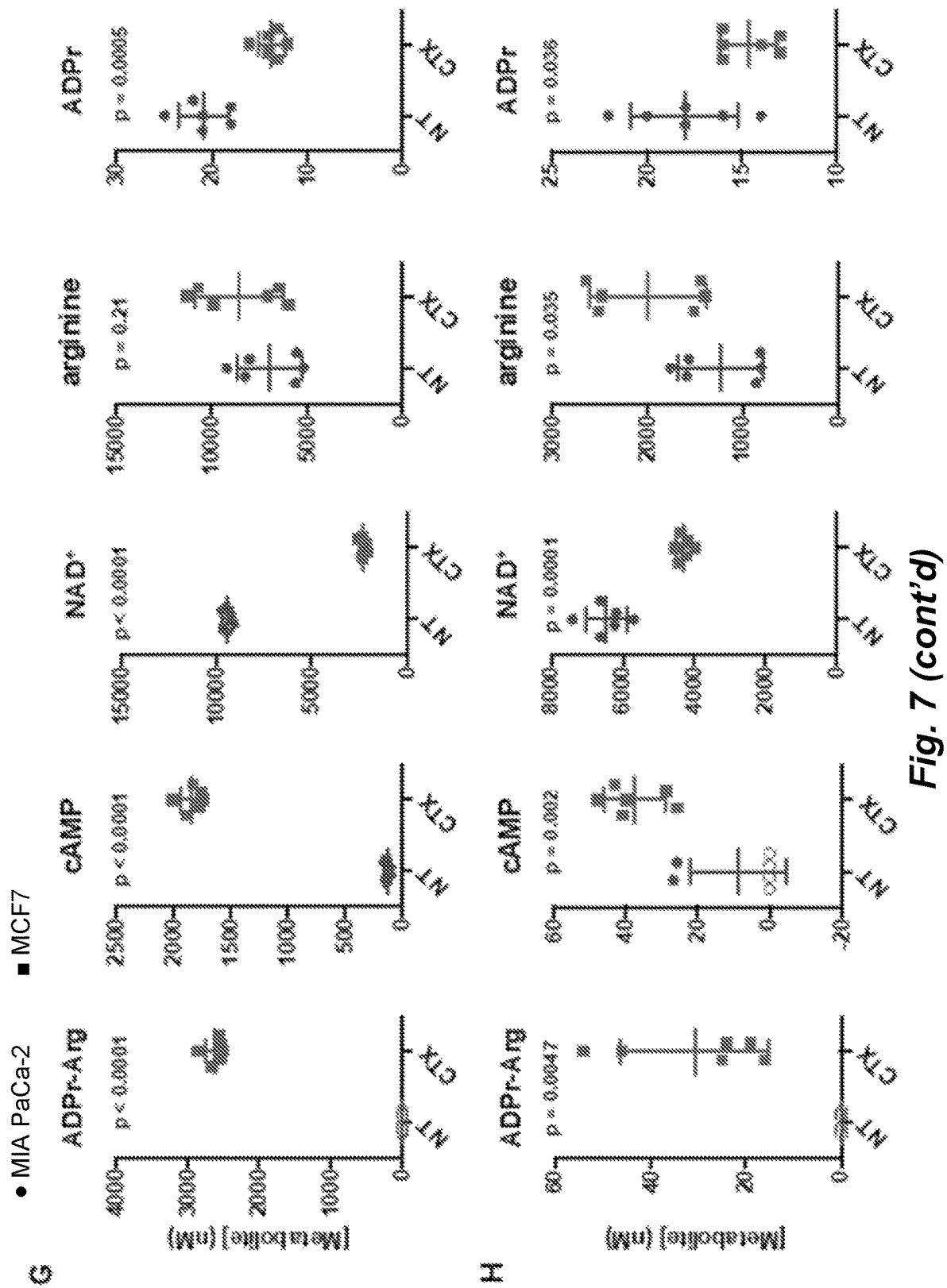

A unique feature of MCF10A cells are the particular additives in the growth media, and most notable is the inclusion of cholera toxin (CTX), a known ADP-ribosyl-transferase (Gill and Meren, 1978; Wang and Schultz, 2014). Suspecting that the presence of CTX may impact ARH3 activity, MCF10A cells were passaged five times in the absence of CTX, and ARH3 activity was restored (FIG. 7A). This recovery of activity was reversed (in a dose and time-dependent manner) with subsequent addition CTX, and this phenotype was reproduced in other cell lines (MCF7 and MIA PaCa-2) (FIG. 7A, B). In all these cell lines, CTX-mediated ARH3 inhibition occurred rapidly ($t_{1/2}$<60 min, FIG. 7B). The treatment of cells with CTX appears to be the first example of selective inhibition ARH3 in cells.

TABLE 3

Data used to construct FIG. 3D.

| Cell Line | ARH3 Activity (milli-units/min/μg) | Relative ARH3 expression (ARH3/actin) |
|---|---|---|
| U87 | 290 ± 52 | 2.3 ± 0.4 |
| HepG2 | 215 ± 19 | 3.0 ± 0.9 |
| HEK | 192 ± 20 | 3.3 ± 0.4 |
| HCT-116 | 173 ± 17 | 1.54 ± 0.06 |
| Hs578t | 170 ± 34 | 1.5 ± 0.6 |
| HeLa | 159 ± 18 | 1.0 ± 0.2 |
| MIA PaCa-2 | 157 ± 25 | 0.49 ± 0.08 |
| MEF | 153 ± 38 | 1.24 ± 0.09 |
| D54 | 147 ± 34 | 0.90 ± 0.05 |
| T98G | 139 ± 7 | 0.9 ± 0.2 |
| U937 | 137 ± 34 | 1.0 ± 0.3 |
| HFF-1 | 105 ± 20 | 0.5 ± 0.1 |

TABLE 3-continued

Data used to construct FIG. 3D.

| Cell Line | ARH3 Activity (milli-units/min/μg) | Relative ARH3 expression (ARH3/actin) |
|---|---|---|
| HCC38 | 100 ± 19 | 0.88 ± 0.09 |
| MCF 7 | 92 ± 40 | 0.8 ± 0.3 |
| SK-MEL-5 | 87 ± 13 | 0.7 ± 0.2 |
| HCC1937 | 76 ± 4 | 0.9 ± 0.2 |
| A549 | 67 ± 23 | 0.38 ± 0.02 |
| Jurkat | 36 ± 7 | 0.3 ± 0.2 |
| Daudi | 27 ± 35 | 1.6 ± 0.7 |
| MCF10A | −5 ± 12 | 0.8 ± 0.3 |

Mechanism of ARH3 Inhibition by ADP-Ribosyl-Arginine

Figure 4:
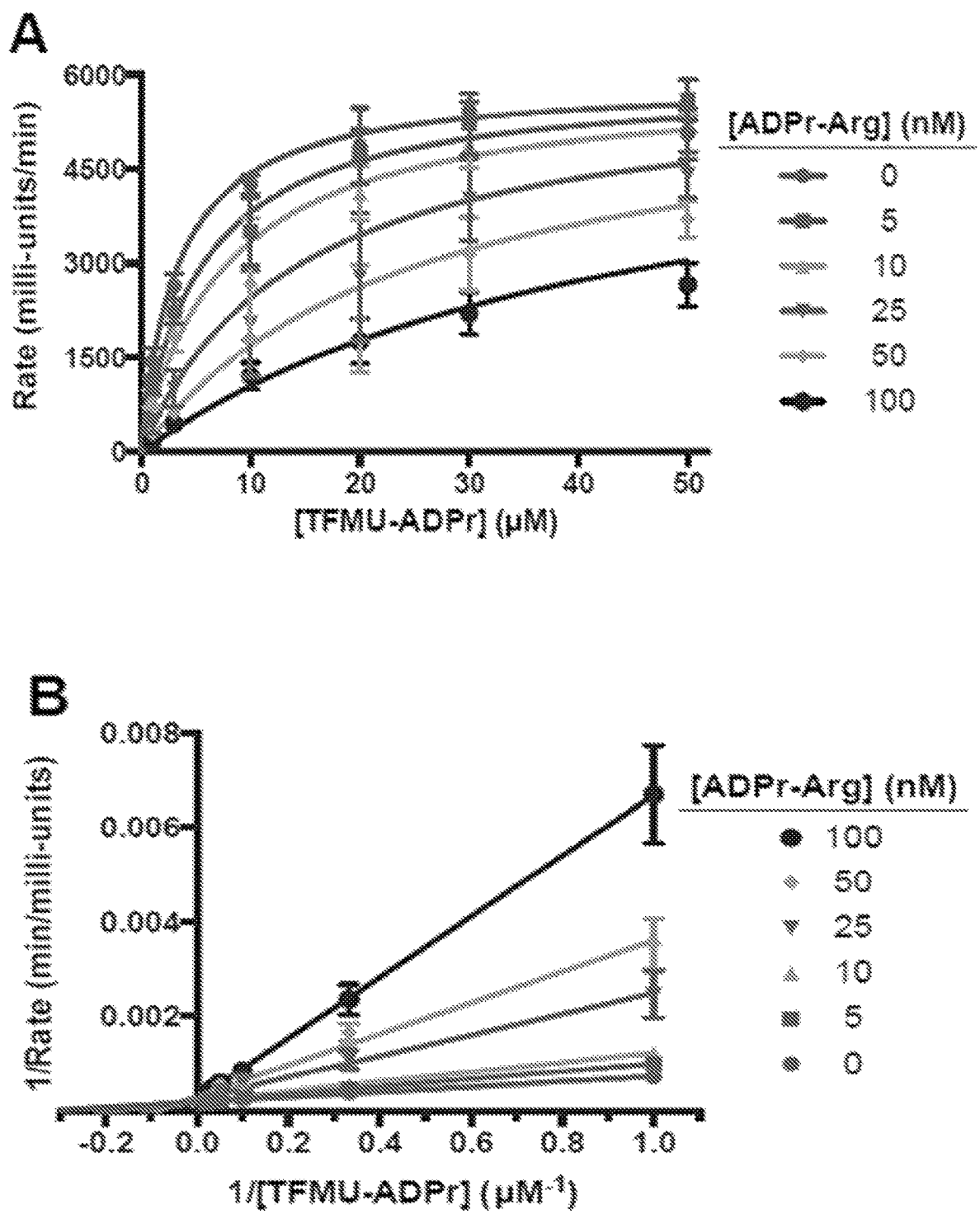
FIG. 4. Selective inhibition of ARH3 by ADP-ribosylated arginine. A. Kinetics of inhibition of ARH3 by ADPr-Arg. B. Lineweaver-Burke plot of ADPr-Arg inhibition of ARH3. C. Selectivity of ADPr-Arg for ARH3 over hPARG is indicated by a shift in dose-response curve. D. Structure of ADPr-Arg.
Figure 4:
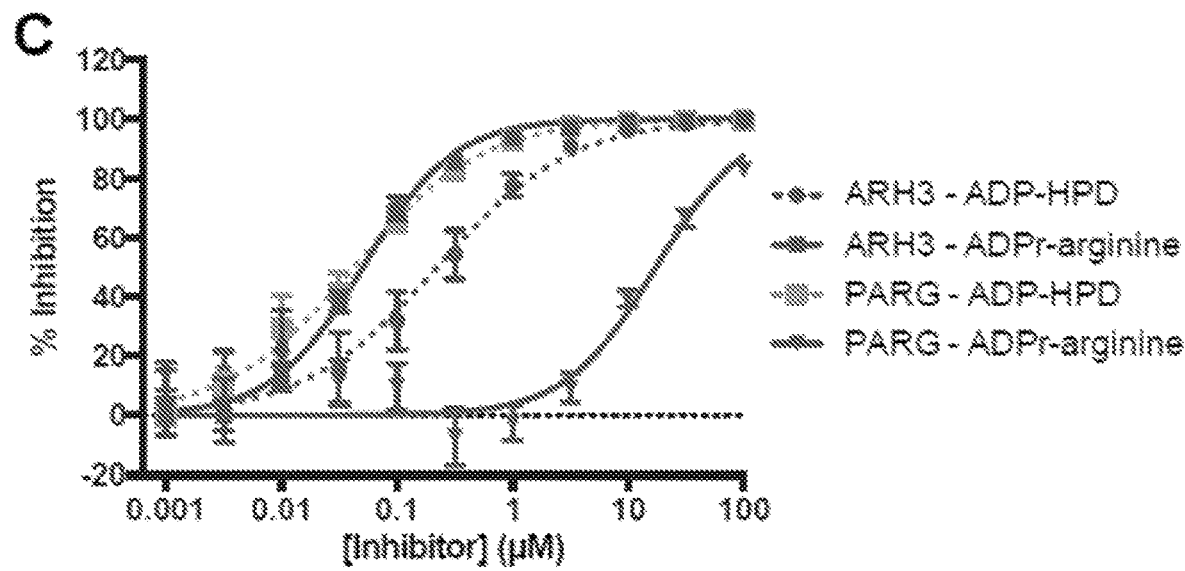
Figure 4:
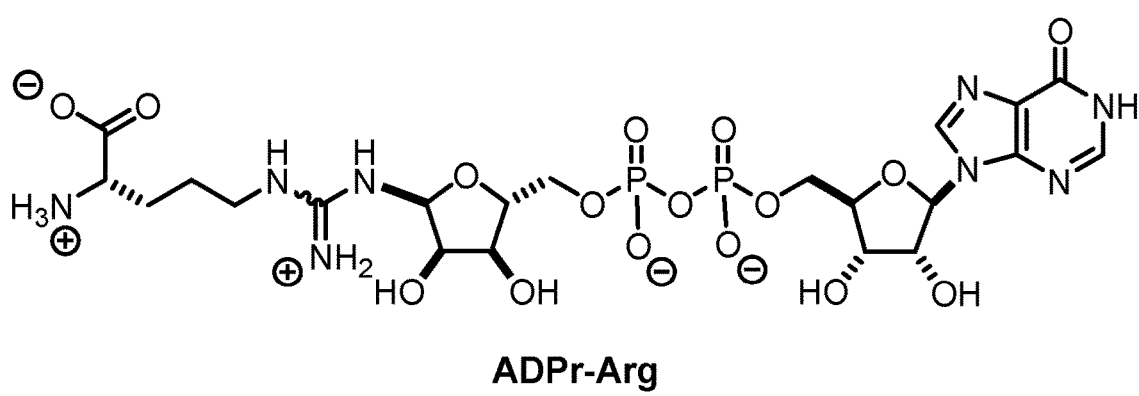
Figure 8:
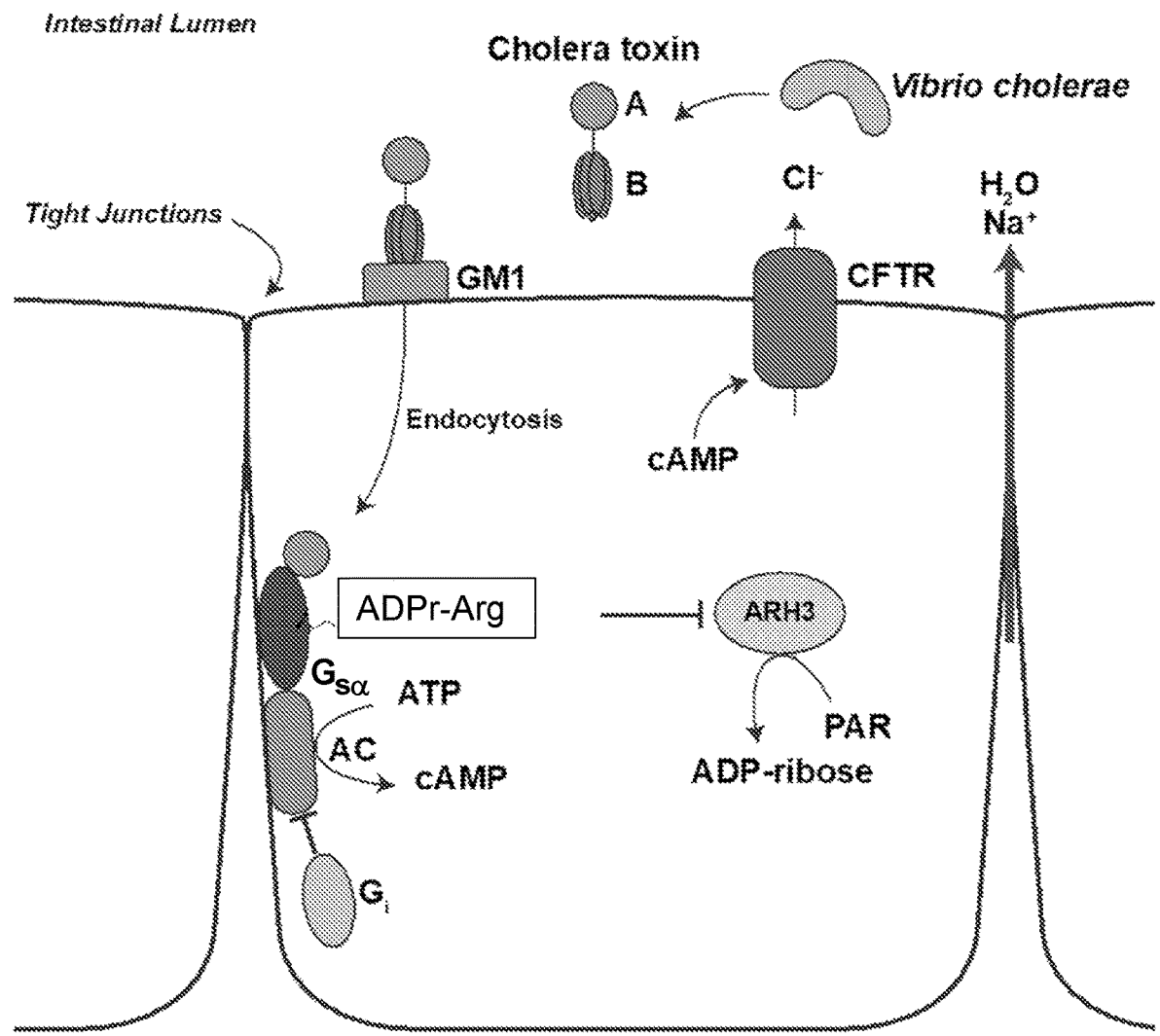
FIG. 8. Related to FIG. 4. Canonical mechanism of action for cholera toxin and involvement of ARH3. Cholera toxin is secreted as a binary toxin by *Vibrio cholera* within the intestinal lumen. Subunit B binds to GM1 receptor and is endocytosed. Subunit A contains an ADP-ribosyltransferase domain that ADP-ribosylates Gsa. This PTM causes constitutive activation of Gsa, which activates AC leading to cAMP synthesis. Increased cAMP concentrations lead to cystic fibrosis transmembrane conductance regulator (CFTR) activation and efflux of chloride. Tight junctions are weakened leading to sodium and water leakage through the intercellular space, resulting in dehydration and loss of electrolytes (Thiagarajah and Verkman, 2012). Pertussis toxin acts through a similar manner by ADP-ribosylation of Gi which also gives rise to increased cAMP synthesis.

Having identified cholera toxin as causing ARH3 inhibition in cell culture, several experiments were performed to elucidate the toxin's mechanism of action. CTX was first found to have no direct effect on ARH3 in vitro (FIG. 7C). The canonical mechanism of CTX involves mono-ADP-ribosylation of an active-site arginine on Gα (G-protein alpha subunit); this post-translational modification results in the constitutive activation of adenylyl cyclase (AC), which synthesizes cAMP (FIG. 8). Thus, the role of AC and cAMP in CTX-dependent ARH3 inactivation were investigated. cAMP was found to only weakly inhibit ARH3 ($IC_{50}$=2.96±0.05 mM, FIG. 7D). Furthermore, treatment with forskolin, a known activator of AC, did not result in ARH3 inhibition (FIG. 7E). Finally, other ADP-ribosyltransferase bacterial ecto-toxins that target other amino acid residues do not inhibit ARH3 activity (FIG. 7F). With these experiments pointing upstream of AC, direct interaction with ADP-ribosyl arginine (ADPr-Arg) was considered. To make assessments, ADPr-Arg was synthesized as described previously (Oppenheimer, 1978) and assessed in the in vitro assay. This compound was found to potently inhibit ARH3 in vitro, with a $K_i$ value of 18±2 nM (FIG. 4A, B). Interestingly, ADPr-Arg demonstrates markedly reduced activity against PARG (FIG. 4C). This differential inhibition is in contrast to the results for the substrate analogue inhibitor of PARG, the compound ADP-HPD; analysis of ADP-HPD shows that this compound inhibits both PARG and ARH3 (FIG. 4C). Importantly, ADPr-Arg substantially accumulated in MCF7 cells following CTX treatment, from concentrations below the limit of detection in untreated cells to 2.62±0.05 μM in the treated cells (FIG. 7G). Changes in related metabolites were also observed: cAMP concentration increased as expected for the canonical activity of CTX, $NAD^+$ concentration decreased (it is a substrate for ADPr-Arg synthesis), but arginine remained unchanged, perhaps due to the presence of exogenous arginine in media. The same trend for these metabolic changes was also observed in U2OS cells (FIG. 7H).

Discussion

This disclosure describes the first continuous substrates for the glycohydrolases that catabolize PAR. The syntheses of these substrates are robust and scalable (hundreds of milligrams of each were prepared), and as such these compounds should find routine use for the measurement of kinetics, the assessment of inhibitors, and for high-throughput screening applications. In addition, their ability to report on this enzymatic activity in cell lysate will enable a variety of experiments where PARG or ARH3 activity is the needed readout, and in such experiments the ARH3-selective substrate TFMU-IDPr can be used to differentiate cellular ARH3 enzymatic activity from PARG activity.

Selective enzyme assays are powerful for assessment of the differential contribution of enzyme family members to total enzymatic activity. The potential impact such experiments can have is apparent in the widespread use of a variety of compounds as caspase substrates. For caspases, specificity can be imbued through use of peptide sequences known to be specifically recognized by different caspases isozymes, and such tool compounds have been widely employed to understand conditions under which specific caspases are activated, and have been critical to mapping the apoptotic cell death pathway. The lack of analogous reagents for monitoring of PAR processing has necessitated reliance on non-ideal methods such as isozyme-general processing of radiolabeled substrates. In the case of PAR-processing enzymes, the development of specific substrates is considerably more complicated than for a protease (where specificity can be built in though understanding of the endogenous protein substrates). The recently solved X-ray structures of ARH3 and PARG, and subsequent docking studies, has now allowed for the design of reporter substrates, one that is general for ARH3 and PARG, and one that is specific for ARH3.

As a first application, these substrates have been used to discover that CTX suppresses cellular ARH3 activity through the production of ADPr-arginine, an ARH3-selective inhibitor. While the effect of bacterial exotoxins on cAMP synthesis and downstream processes has been extensively described (FIG. 8), their effects off-pathway are less understood. CTX, *Clostridium difficile* binary toxin (CDT), and pertussis toxin (PT) catalyze the mono-ADP-ribosylation of arginine (CTX and CDT) and cysteine (PT) residues. While the background ADP-ribosylation of arginine by CTX has been observed with isolated protein (Oppenheimer, 1978), the activity of CTX has largely been regarded to be highly selective for proteinaceous arginine. Observation and quantification ADP-ribosylation of free arginine was observed for the first time in a cell culture at concentrations that rationalize ARH3 inhibition. The absence of ARH3 inhibition following CDT treatment, despite creating the same PTM, may result from differential propensities to produce free and proteinaceous ADPr-arginine. However, the possibility remains that the observed ADPr-arginine results from proteolytic breakdown of ADP-ribosylated G proteins rather than direct ADP-ribosylation. In this case, the differential activities of bacterial toxins can be attributed to stabilities of their respective protein targets. Some of the phenotypes described upon treatment by bacterial toxins (i.e. loss of tight junctions) has also been described for PAR overproduction. While the exact mechanism by which these processes operate is yet unknown, inhibition of ARH3 may assist in toxins' ability to elevate PAR concentrations. The ready availability of these ARH3 and PARG substrates will now facilitate additional discoveries about the regulation of cellular PAR processing.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5$^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Experimental Method Details

Cell Lines

A549, D54, HCC1937, HCC38, HCT-116, Jurkat, and U937 cells were grown in RPMI 1640 supplemented with 10% fetal bovine serum (Gemini) and 1% pen/strep. U2OS, Daudi, HEK293TN, HeLa, Hs578t, MEF, MIA PaCa-2, and SK-MEL-5 cells were grown in Dulbecco's modified Eagle's medium supplemented with 10% fetal bovine serum and 1% pen/strep. HFF-1 cells were grown in Dulbecco's modified Eagle's medium supplemented with 15% fetal bovine serum and 1% pen/strep. HepG2, MCF7, T98G, and U87 cells were grown in Eagle's Minimum Essential Medium supplemented with 10% fetal bovin serum and 1% pen/strep. MCF10A cells were grown in Dulbecco's modified Eagle's medium supplemented with 2% horse serum, 20 ng/mL EGF, 0.5 µg/mL hydrocortisone, 10 µg/mL insulin, 100 ng/mL cholera toxin, and 1% pen/strep. Phenol red was added to all media except for MCF10A as a pH indicator. All cells were cultured at 37° C. in a 5% $CO_2$ environment. Media were prepared by the University of Illinois School of Chemical Sciences Cell Media Facility.

Buffer Composition:
  PARG Activity Lysis Buffer: 30 mM Tris (pH 7.5), 500 mM NaCl, 20% glycerol, 1% Triton X-100, 1:500 protease inhibitor cocktail.
  Lysate Activity Buffer: 50 mM $K_2HPO_4$ (pH 7.4), 50 mM KCl, 5 mM $MgCl_2$, 5 mM DTT.
  *T. thermophila* PARG reaction buffer: 50 mM $K_2HPO_4$, 50 mM KCl, 10 mM β-mercaptoethanol, pH 7.40.
  Human PARG reaction buffer: 50 mM $K_2HPO_4$, 50 mM KCl, 10 mM β-mercaptoethanol, pH 7.40.
  Human ARH3 reaction buffer: 50 mM $Na_2HPO_4$, 10 mM $MgCl_2$, 5 mM DTT, pH 7.40.
  PARG Purification Lysis buffer: 50 mM $NaH_2PO_4$, 300 mM NaCl, 10 mM imidazole, 0.5 mg/mL lysozyme, 1 ug/mL leupeptin, 1 ug/mL pepstatin A, 2 ug/mL aprotinin, 1 mM PMSF, pH 8.0.
  PARG Purification Wash buffer: 50 mM $NaH_2PO_4$, 300 mM NaCl, 10 mM imidazole, pH 8.0.
  PARG Purification Elution buffer: 50 mM $NaH_2PO_4$, 300 mM NaCl, 300 mM imidazole, pH 8.0.
  PARG Purification Dialysis buffer: 25 mM Tris, 50 mM NaCl, 1 mM DTT, 10% glycerol, pH 7.5.
  Towbin Transfer Buffer: 20% $CH_3OH$, 192 mM glycine, 50 mM Tris, pH 8.3.

In Vitro Enzyme Kinetics

10× dilutions of substrate were prepared from 10 mM stock solutions in MilliQ $H_2O$ into reaction buffer. 5 µL 10× substrate was added to a 384-well plate. 45 µL 2.2 nM enzyme solution in reaction buffer was added to a single column of the 384-well plate via 16-channel Matrix pipet. Plate was placed into plate reader. After shaking for 5 s, absorbance or fluorescence was recorded at 2 s intervals for 5 min. Initial reaction rates were determined by fitting the linear portions of reaction progress curves using SoftMax Pro 6.4. Initial rates were plotted against substrate concentration and fit to the Michaelis-Menton equation using a non-linear curve-fitting algorithm with GraphPad Prism 6. For pNP detection, plate reader was configured: absorbance at 405 nm. For TFMU detection, plate reader was configured: Excitation 385 nm, Cutoff 495 nm, Emission 502 nm, 6 reads/well, Low Gain.

Cell Lysate ARH3 Activity Assay

Cells were cultured in T75 flasks in appropriate medium. Cells were trypsinized, and scrapped (if necessary), and counted. $1 \times 10^6$ cells were harvested and washed with cold PBS 2×. Cell pellet was lysed by addition of activity lysis buffer (150 µL) and incubated on ice for 30 min. Lysate was clarified by centrifugation at 14,300×g at 4° C. for 10 min. Supernatant was transferred to chilled, empty 500 µL tube. Total protein content of lysate was evaluated by BCA assay. ARH3 expression level was determined by western blotting analysis. 5 µL lysate was added to well of 384-well black plate. 45 µL TFMU-IDPr (200 µM final) in reaction buffer was added to well. Reaction progress was monitored by fluorescent plate reader (ex 385 nm, cutoff 495, em 502 nm, 6 reads/well, high gain).

ADP-Ribosylated Arginine Enzymatic Synthesis

CTX (100 µL, 500 µg/mL, 10 µg/mL final) was added to 5 mL buffer (400 mM $K2HPO_4$, 20 mM DTT, pH 7.2) containing 200 mM arginine and 10 mM NAD. Mixture was incubated at 37° C. for 16 h. Protein was removed from reaction mixture by filtration through 3 k MWCO spin filter. Filtrate was direction subjected to ion-pairing preparative HPLC using Luna C1821.5×150 mm column. Solvent A: 20 mM $Et_3N$·HOAc (pH 7.2), solvent B: acetonitrile. Gradient (A:B, 20 mL/min): 98:2, 0 min; 98:2, 2 min; 75:25, 16 min; 75:25, 23 min; 40:60, 27 min, 40:60, 30 min. ADP-ribosylated arginine eluted at ~5 min as two separate anomers. Individual anomers gradually interconverted in ~1 h, so characterization and inhibition experiments were performed with mixture of anomers. Product-containing fractions were determined by LCMS and lyophilized to yield flocculent white solid (7.8 mg, 21%). $^1H$ NMR was consistent with previous reports (J. Biol. Chem. 1978, 253, 4907).

Metabolic Profiling

Six-well plates were seeded with cells at $3 \times 10^5$ cells/well. When cells were ~80% confluent, cells were treated with 100 ng/mL CTX for 6 h. Cells were washed with PBS once and detached with trypsin, quenching trypsin with media with 10% FBS. Cell viability was verified by Trypan Blue exclusion. Cells were centrifuged at 400×g at 4° C. for 4 min and washed with PBS twice. Cell pellets were resuspended with cold 70:30 methanol:water and placed on ice. Cell suspension was sonicated on ice (20%, 10 s on, 10 s off, 30 s total) and continued to be incubated on ice for 30 min. Lysate was clarified by centrifugation at 14,300×g at 4° C. for 30 min. Supernatant was transferred to an empty 0.5 mL tube and stored at −80° C. until analysis. Samples were analyzed with the 5500 QTRAP LC/MS/MS system (Sciex, Framingham, MA) in Metabolomics Lab of Roy J. Carver Biotechnology Center, University of Illinois at Urbana-Champaign. Software Analyst 1.6.2 was used for data acquisition and analysis. The 1200 series HPLC system (Agilent Technologies, Santa Clara, CA) includes a degasser, an autosampler, and a binary pump. The LC separation was performed on an Agilent SB-Aq (4.6×50 mm, 5 m) with mobile phase A (0.1% formic acid in water) and mobile phase B (0.1% formic acid in acetonitrile). The flow rate was 0.3 mL/min. The linear gradient was as follows: 0-3 min, 100% A; 5-10 min, 2% A; 11-15 min, 100% A. The autosampler was set at 10° C. The injection volume was 5 µL. Mass spectra were acquired under positive electrospray ionization (ESI) with the ion spray voltage of +5500 V. The source temperature was 450° C. The curtain gas, ion source gas 1, and ion source gas 2 were 36, 65, and 60, respectively. Multiple reaction monitoring (MRM) was used for quantitation: Arg m/z 175.1→m/z 70.1; ADP-Arg m/z 716.2→m/z 428.1; cAMP m/z 330.2→232.0; ADP-ribose m/z 560.1→m/z 348.1; NAD m/z 664.2→m/z 136. Limit of quantitation (LOQ) for the compounds were: 10 ng/mL ADPr-Arg, 10 ng/mL ADP-ribose, 10 ng/mL arginine, 20 ng/mL cAMP, and 100 ng/mL NAD*.

Recombinant Protein Expression and Purification

Human ARH3 was expressed as previously described (Nat. Commun. 2013, 4, 2164). Briefly, human ARH3 cloned into a pDEST vector with an N-terminal His$_6$-tag was obtained from Hening Lin (Cornell University, Cornell, NY) was transformed into Rosetta2 (DE3) *E. coli* cells. 500 mL culture of LB (100 µg/mL ampicillin and 20 µg/mL chloramphenicol) was inoculated with 10 mL of overnight culture. The culture was grown at 37° C. to mid-log phase ($OD_{600}$=0.5) and cooled to 18° C. Protein expression was induced with 0.1 mM IPTG for 18 h and harvested. Pellet was resuspended in 13 mL lysis buffer and lysed by sonication. Lysate was clarified by centrifugation (35,000×g, 30 min, 4° C.). Supernatant was purified on Ni-NTA beads by batch protocol. Fractions containing pure protein were combined, dialyzed, and stored at –80° C. Protein concentration was determined by BCA assay.

*T. thermophila* PARG enzyme was expressed using a modified protocol a previously reported (Nat. Commun. 2012, 3, 878). Briefly, *T. thermophila* PARG2 cloned into a pET28a vector was obtained from Ivan Ahel (University of Oxford, Oxford, UK) and transformed into Rosetta2 (DE3) *E. coli*. 500 mL culture of LB (100 µg/mL kanamycin and 20 µg/mL chloramphenicol) was inoculated with 10 mL of overnight culture. The culture was grown to mid-log phase ($OD_{600}$=0.7). Culture was induced with 0.3 mM IPTG at 30° C. for 3 h and harvested. Pellet was resuspended in 13 mL lysis buffer and lysed by sonication. Lysate was clarified by centrifugation. Protein was purified on Ni-NTA beads by batch protocol. Fractions containing pure protein were combined, dialyzed, and stored at –80° C. Protein concentration was determined by BCA assay.

Human PARG cloned into a pColdTF vector was obtained from Ivan Ahel (University of Oxford, Oxford, UK) and transformed into Rosetta2 (DE3) *E. coli*. Culture of Terrific Broth supplemented with appropriate antibiotics was grown to an $OD_{600}$=0.6-0.8 at 37° C. Culture was induced with 0.1 mM IPTG at 18° C. for 16 h and harvested. Pellet was resuspended in lysis buffer (40 mM HEPES, 300 mM NaCl, 20 mM imidazole, 10% glycerol, 1 mM TCEP, pH 8.0) supplemented with benzonase, lysozyme and protease inhibitor (Roche Complete EDTA-free protease inhibitor tablet) and lysed by freeze/thaw. Lysate was clarified by centrifugation. Protein was purified on Ni-NTA beads by batch and eluted with lysis buffer supplemented with 500 mM imidazole.

Western Blot Analysis

Samples loading was normalized based on total protein content as assessed by BCA assay and subjected to SDS-PAGE. Protein was transferred to PVDF membranes (Merck Millipore). Membranes were cut along molecular weight markers and then blocked with TBS-T buffer (25 mM Tris-HCl, 150 mM NaCl, 0.05% Tween 20, pH 7.5) supplemented with either 5% BSA (PARP1) or 5% non-fat dried milk (ARH3) for 1 h. Membrane strips were incubated overnight with primary antibodies in blocking buffer at 4° C. with gentle rocking. Membranes were washed 3× with TBS-T and incubated with H1RP-conjugated secondary antibody in TBS-T for 1 h. Membranes were washed 3× with TBS-T, developed using SuperSignal West Pico and imaged using a ChemiDoc MP system. Membrane strip containing ARH3 bands was stripped and reimaged with anti-actin antibody. Dilutions for antibodies were: anti-PARP1 (1:3000), anti-ARH3 (1:1000), anti-actin (1:3000), anti-rabbit (1:3000), and anti-mouse (1:3000). Band quantification was performed using FIJI.

Molecular Docking

Protein and ligand preparation, docking, and scoring was performed using the Schrodinger Suite 2018-1. Proteins were prepared using the Protein Prep Wizard using standard settings with pH set to 7.4. Receptor grids were generated based on bound ADP-ribose. Additional positional constraints were applied so that the nucleobase occupies the adenine binding site and the ribose ring occupies the active site. Sugar nucleotide protonation state and tautomer form was determined using LigPrep. Docking was performed with Glide using both standard precision (SP) and extra precision (XP). Docking poses were exported and rendered using PyMOL.

General Chemical Synthesis

All reactions were run in flame or oven dried glassware under and atmosphere of dry nitrogen unless otherwise noted. Acetonitrile, tetrahydrofuran, methanol, dimethylformamide, toluene, and methylene chloride using in reactions were obtained from a solvent dispensing system. 4 Å molecular sieves were dried at 150° C. on high vacuum overnight. Pyridine, diazabicyclo[5.4.0]undec-7-ene, diisopropylethylamine, and trimethylamine were distilled from $CaH_2$ and stored on 4 Å sieves. All other reagents were of standard commercial purity and were used as received. Analytical thin-layer chromatography was performed on EMD Merck silica gel plates with F254 indicator. Plates were visualized with UV light (254 nm) or staining with p-anisaldehyde. Silica gel for column chromatography was purchased from Macherey-Nagel (40-63 µm particle size).

Unless otherwise indicated, $^1$H, $^{13}$C, $^{19}$F, and $^{31}$P NMR spectra were recorded at 500, 126, 470, and 202 MHz, respectively. $^1$H and $^{13}$C NMR spectra were referenced to the residual solvent peak. $^{19}$F NMR spectra were referenced using absolute referencing based on 1H spectra. $^{31}$P NMR spectra were externally referenced to 85% $H_2PO_4$ (0.00 ppm) in water. Chemical shifts are reported in ppm and multiplicities are reported as s (singlet), d (doublet), t (triplet), q (quartet), p (pentet), h (hextet), m (multiplet), and br (broad). Mass spectrometry analysis was performed by the University of Illinois Mass Spectrometry Center.

Preparative C18 chromatography was performed using a Teledyne Isco Combiflash Rf system with RediSep Gold columns. Silyl ether protected intermediates were separated using a gradient of $H_2O/CH_3CN$ beginning with 95% $H_2O$:

5% CH₃CN, ramping to 65% H₂O:35% CH₃CN over 6 min, ramping to 100% CH₃CN over 6 min, and holding 100% CH₃CN for 5 min. Unprotected substrates were separated using a gradient of 10 mM Et₃N·HOAc (pH 7.2)/CH₃CN beginning with 100% buffer, ramping to 15% buffer:85% CH₃CN over 10 min, ramping to 50% buffer:50% CH₃CN over 6 min, and holding 50% buffer:50% CH₃CN for 4 min.

Quantification and Statistical Analysis

All the data were presented as mean±standard error of mean from at least three independent trials. All data fitting and statistical analysis was performed using GraphPad Prism (version 6).

Example 2. Synthesis of PARG Substrates

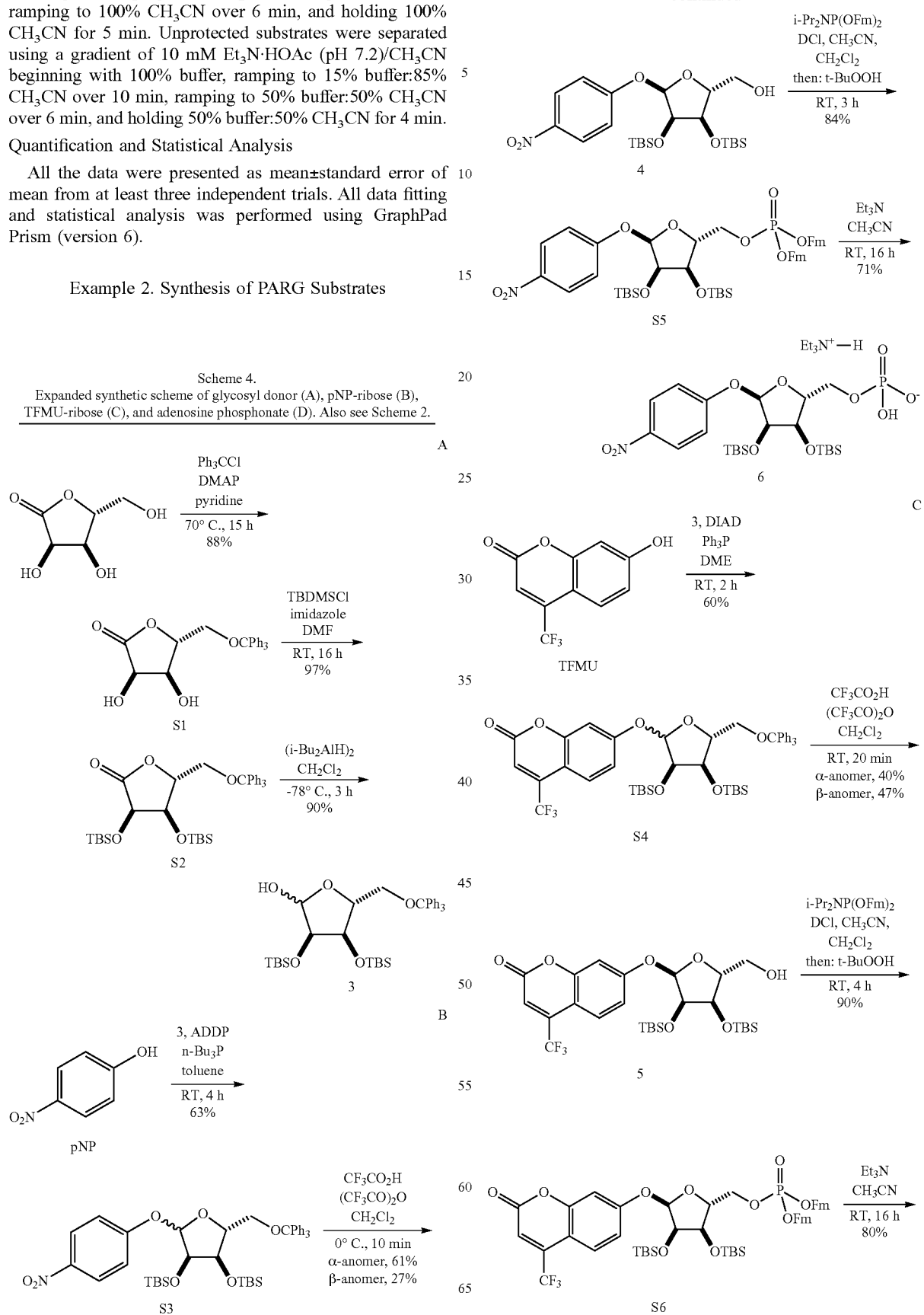

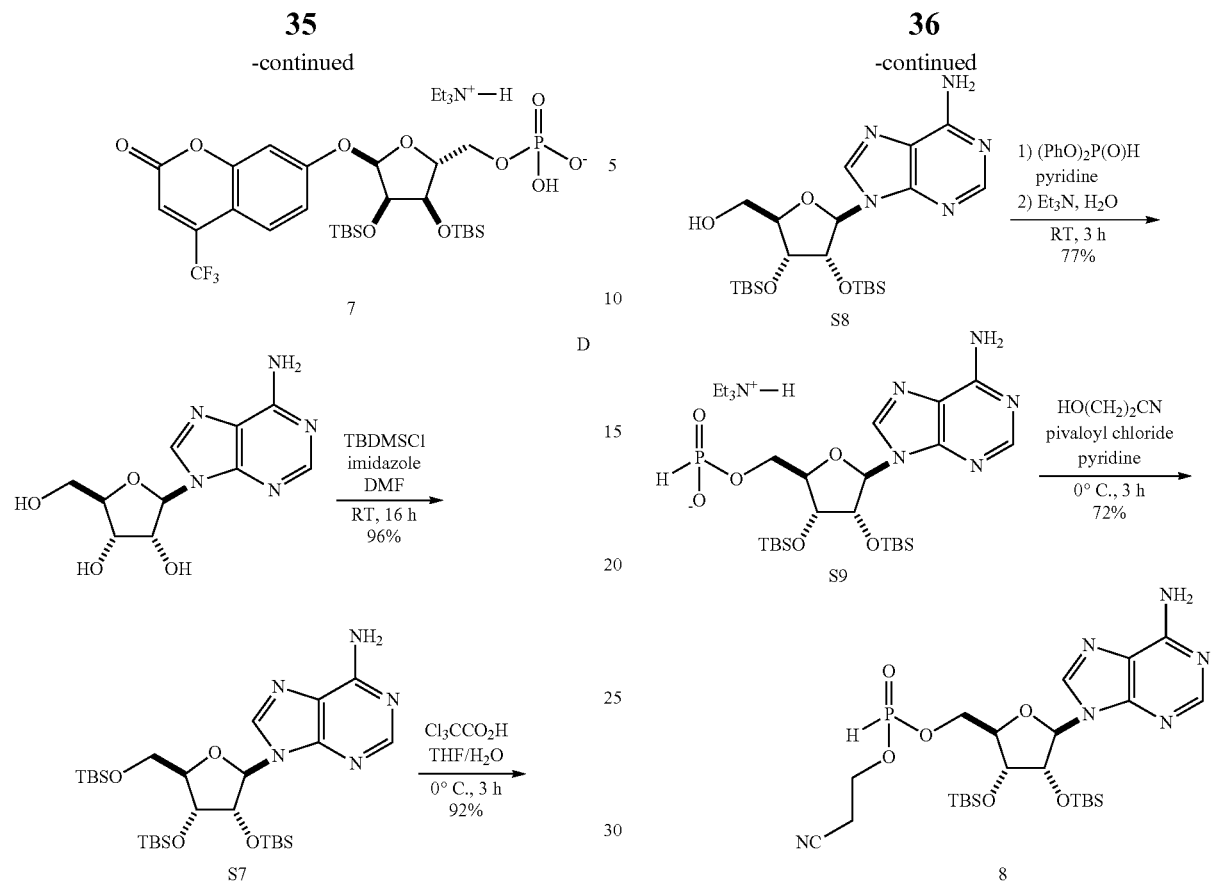
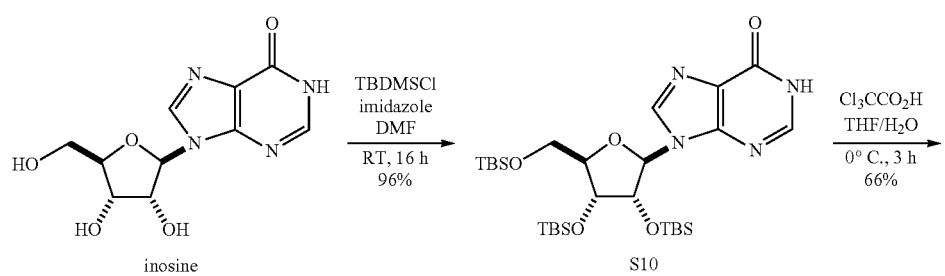
Scheme 5. Synthesis of pNP—IDPr. See also Scheme 3.
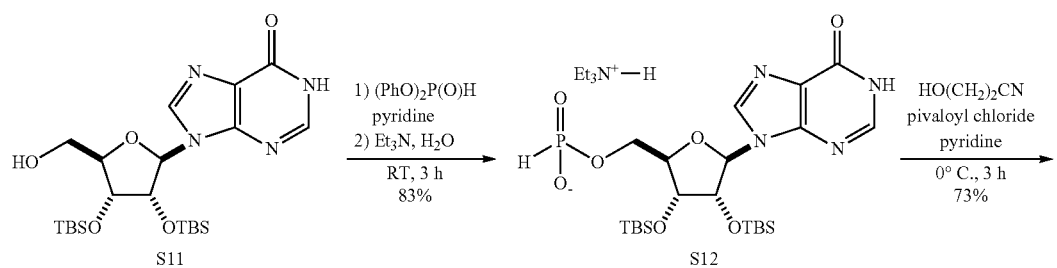

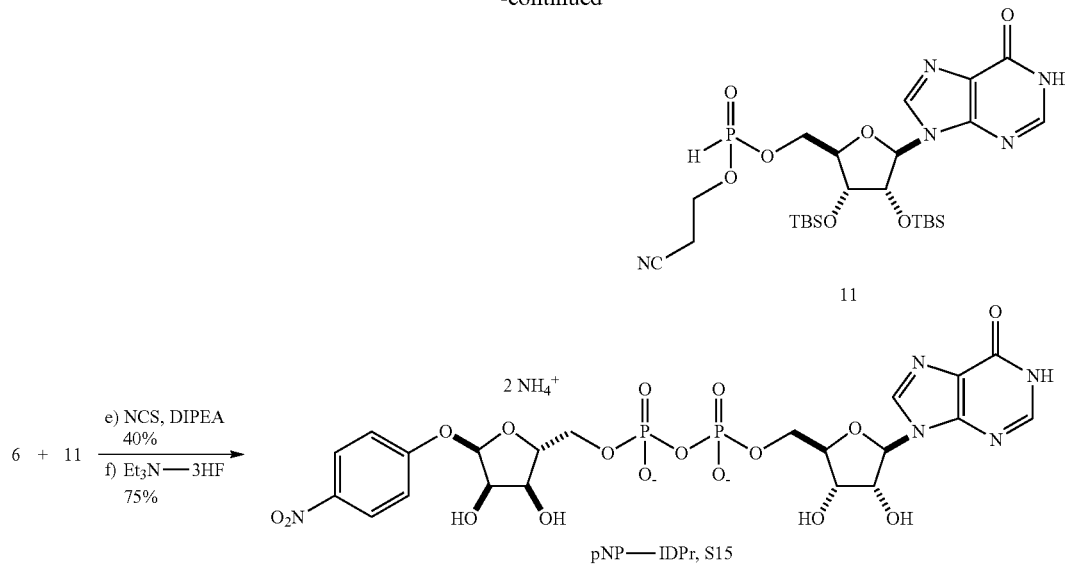

The synthesis of ADPr-Arg is shown in Scheme 6.

Scheme 6. Synthesis and numbering of ADPr-Arg.

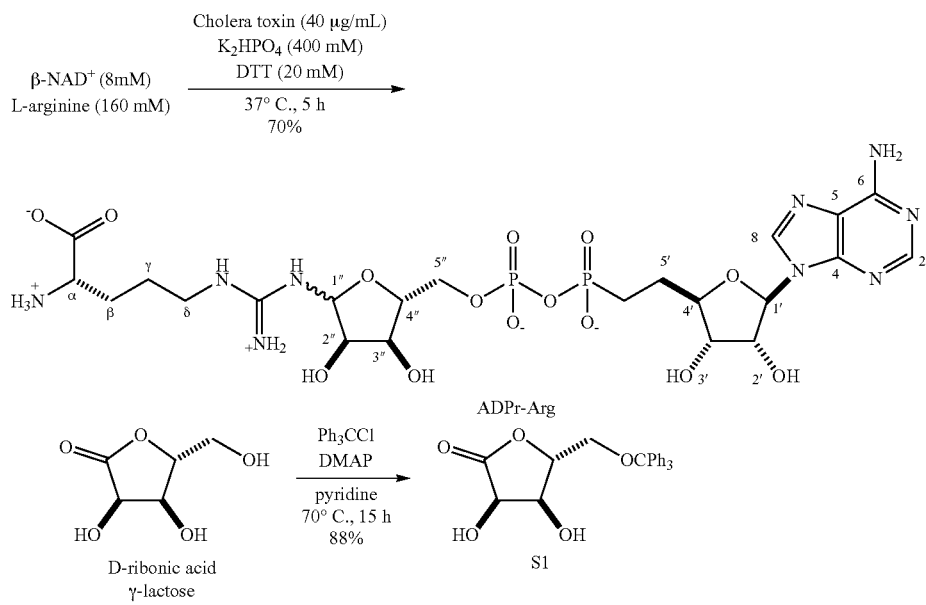

5-O-trityl-D-ribono-1,4-lactone (S1): Synthesized with modification of previous report (J. Org. Chem. 2002, 67, 4466). Specifically, to a 250 mL round bottom flask was added D-ribonic acid γ-lactone (2.15 g, 14.5 mmol, 1 eq), 4-dimethylaminopyridine (360 mg, 2.9 mmol, 0.2 eq), and pyridine (42 mL). Once fully dissolved, triphenylmethyl chloride (4.86 g, 17.4 mmol, 1.2 eq) was added as a solid in one portion to the stirring reaction mixture at room temperature. The solution was stirred at 70° C. for 16 h. The cooled reaction mixture was diluted with dichloromethane and washed with 1 M HCl twice and satd aq NaHCO$_3$ once. The organic layer was dried over MgSO$_4$, filtered through a pad of celite, and concentrated in vacuo. The residue was purified by silica gel chromatography, eluting with 1:1 hexanes-EtOAc, yielding compound S1 as a white solid (5.0 g, 88%).

$^1$H NMR (500 MHz, DMSO-d$_6$) δ 7.41-7.24 (m, 15H), 5.93 (d, J=7.6 Hz, 1H), 5.45 (d, J=4.0 Hz, 1H), 4.54 (dd, J=7.6, 5.5 Hz, 1H), 4.39-4.34 (m, 1H), 4.02 (ddd, J=5.3, 4.0, 1.2 Hz, 1H), 3.41-3.33 (m, 1H), 3.14 (dd, J=11.0, 3.8 Hz, 1H).

$^{13}$C NMR (126 MHz, DMSO-d$_6$) δ 176.2, 143.2, 128.2, 128.1, 127.3, 86.7, 83.4, 69.4, 68.6, 63.0.

HRMS (ESI-TOF) m/z: [M+Na]$^+$ Calcd for C$_{24}$H$_{22}$O$_5$Na 413.1365. Found 413.1362.

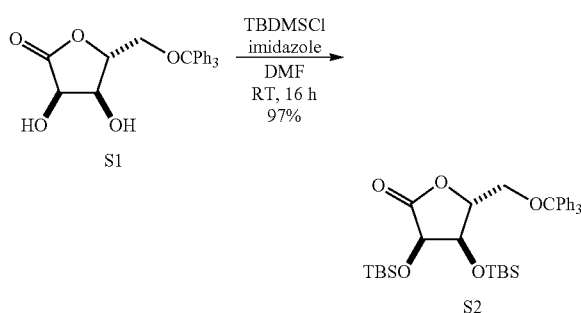

2,3-bis-O-tert-butyldimethylsilyl-5-O-trityl-D-ribono-1,4-lactone (S2): Synthesized with modification of previous reports (J. Org. Chem. 2002, 67, 4466). Specifically, to a 100 mL round bottom flask was added S1 (2.0 g, 5.1 mmol, 1 eq), imidazole (1.9 g, 27 mmol, 5 eq), and dimethylformamide (20 mL). The solution was cooled to 0° C. Tert-butyldimethylsilyl chloride (2.9 g, 19 mmol, 4 eq) was added as a solid in one portion. Solution was allowed to warm to room temperature and was stirred for 16 h. Reaction mixture was diluted with diethyl ether and quenched with the addition of satd aq NH$_4$Cl. Organic layer was washed with satd aq NaHCO$_3$ thrice and brine once. Organic layer was dried over Na$_2$SO$_4$, filtered, and concentrated. Residue was purified by silica gel chromatography, eluting with 5% Et$_2$O-hexane, to yield compound S2 as a white foam (3.1 g, 97%).

$^1$H NMR (500 MHz, CDCl$_3$) δ 7.40 (d, J=8.4 Hz, 6H), 7.31 (t, J=7.6 Hz, 6H), 7.25 (t, J=7.1 Hz, 3H), 4.68 (d, J=5.2 Hz, 1H), 4.29 (t, J=3.0 Hz, 1H), 3.95 (dd, J=5.2, 1.1 Hz, 1H), 3.62 (dd, J=11.0, 3.7 Hz, 1H), 3.21 (dd, J=11.0, 2.8 Hz, 1H), 0.93 (s, 9H), 0.80 (s, 9H), 0.18 (s, 3H), 0.11 (s, 3H), 0.01 (s, 3H), −0.06 (s, 3H).

$^{13}$C NMR (126 MHz, CDCl$_3$) δ 175.27, 143.19, 128.63, 128.18, 127.49, 84.70, 77.16, 72.16, 70.44, 62.39, 25.96, 25.75, 18.51, 18.20, −3.45, −4.47, −4.70, −5.04.

HRMS (ESI-TOF) m/z: [M+Na]$^+$ Calcd for C$_{36}$H$_{50}$O$_5$Si$_2$Na 641.3094. Found 641.3093.

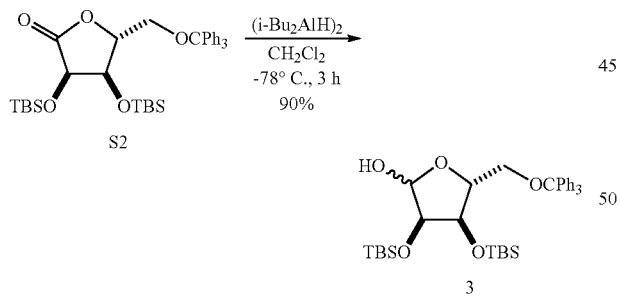

2,3-bis-O-tert-butyldimethylsilyl-5-O-trityl-D-ribose (3): A 1 M solution of (i-Bu$_2$AlH)$_2$ in hexane (17.5 mL, 17.5 mmol, 1.5 eq) was added dropwise via addition funnel over 5 min to a stirring solution of S2 (7.25 g, 11.7 mmol, 1 eq) in CH$_2$Cl$_2$ (120 mL) at −78° C. The resulting solution was stirred at −78° C. for 3 h. Reaction was quenched with the addition of CH$_3$OH (4 mL) added dropwise via addition funnel and allowed to warm to 0° C. After stirring for 30 min, 200 mL 0.5 M potassium sodium tartrate was added, and mixture was stirred until aluminum salts were fully dissolved. Extracted mixture with CH$_2$Cl$_2$ three times. The combined organic layers were dried over MgSO$_4$, filtered through a pad of celite, and concentrated. The residue was purified by silica gel chromatography, eluting with 10% Et$_2$O-hexanes, to yield an interconverting mixture of diastereomers of compound 3 as a white foam (6.5 g, 90%).

β anomer (major)

$^1$H NMR (500 MHz CDCl$_3$) δ 7.50-7.43 (m, 6H), 7.35-7.30 (m, 6H), 7.29-7.24 (m, 3H), 5.13 (dd, J=11.4, 4.3 Hz, 1H), 4.24 (d, J=11.4 Hz, 1H), 4.16 (t, J=4.5 Hz, 1H), 3.92 (d, J=4.6 Hz, 1H), 3.26 (dd, J=10.4, 4.9 Hz, 1H), 3.11 (dd, J=10.4, 3.3 Hz, 1H), 0.93 (s, 9H), 0.85 (s, 9H), 0.13 (s, 3H), 0.10 (s, 3H), 0.04 (s, 3H), −0.02 (s, 3H).

α Anomer (Minor)

$^1$H NMR (500 MHz CDCl$_3$) δ 7.50-7.43 (m, 6H), 7.35-7.30 (m, 6H), 7.29-7.24 (m, 3H), 5.19 (d, J=4.6 Hz, 1H), 4.40 (dd, J=7.3, 4.0 Hz, 1H), 4.20 (t, J=4.0 Hz, 1H), 4.11 (ddd, J=7.0, 3.8, 2.6 Hz, 1H), 3.97 (d, J=4.1 Hz, 1H), 3.49 (dd, J=10.3, 2.7 Hz, 1H), 3.10 (dd, J=10.2, 3.9 Hz, 1H), 2.71 (d, J=4.6 Hz, 1H), 0.91 (s, 9H), 0.75 (s, 9H), 0.11 (s, 3H), 0.09 (s, 3H), −0.03 (s, 3H), −0.19 (s, 3H).

Both Anomers $^{13}$C NMR (126 MHz, CDCl$_3$) δ 143.80, 129.01, 128.77, 128.01, 127.95, 127.26, 127.23, 102.19, 97.90, 87.05, 87.01, 84.43, 81.78, 77.06, 74.56, 72.58, 71.74, 63.77, 63.31, 26.06, 25.96, 25.92, 25.86, 18.42, 18.26, 18.11, 18.09, −4.08, −4.29, −4.46, −4.49, −4.55, −4.67, −4.90, −4.94.

HRMS (ESI-TOF) m/z: [M+Na]$^+$ Calcd for C$_{36}$H$_{52}$O$_5$NaSi$_2$ 643.3251. Found 643.3251.

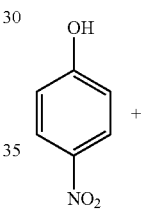

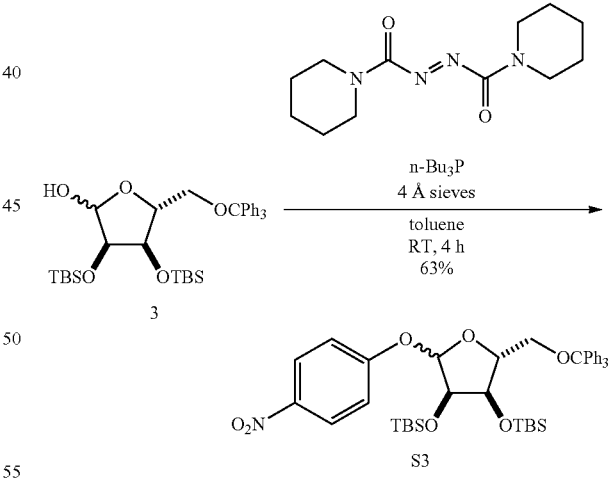

4-nitrophenyl 2,3-bis-O-tert-butyldimethylsilyl-5-O-trityl-D-ribofuranoside (S3): To a 250 mL round bottom flask, were added 3 (3.80 g, 6.11 mmol, 1 eq), 4-nitrophenol (2.51 g, 18.1 mmol, 3 eq), 4 Å molecular sieves (200 mg), and toluene (100 mL). Cooled mixture to 0° C. Added n-Bu$_3$P (3.80 mL, 0.81 g/mL, 3.1 g, 15 mmol, 2.5 eq) dropwise via syringe. Added 1,1'-(azodicarbonyl)dipiperidine as a solid in one portion. Mixture was stirred at 0° C. for 30 min and then allowed to warm to room temperature and stirred for an additional 4 h. The reaction mixture was cooled to 0° C., and 30% H$_2$O$_2$ (5 mL) was added to fully quench phosphine.

After stirring for 30 min, the reaction mixture was diluted with hexane (100 mL). The resulting yellow precipitate was removed by filtration through a pad of celite. The filtrate was washed with satd aq NaHCO$_3$ five times, dried over Na$_2$SO$_4$, filtered, and concentrated. The residue was purified by silica gel chromatography, eluting with 5% Et$_2$O-hexanes, to yield compounds S3 (a mixture of anomers, α:β69:31) as a pale-yellow foam (2.87 g, 63%).

α-anomer $^1$H NMR (500 MHz, CDCl$_3$) δ 8.21 (d, J=9.0 Hz, 2H), 7.48-7.43 (m, 6H), 7.32 (t, J=7.7 Hz, 6H), 7.29-7.24 (m, 3H), 7.13 (d, J=9.3 Hz, 2H), 5.65 (d, J=4.1 Hz, 1H), 4.38 (t, J=4.7 Hz, 1H), 4.18 (q, J=3.0 Hz, 1H), 4.05 (dd, J=5.2, 2.2 Hz, 1H), 3.42 (dd, J=10.5, 3.5 Hz, 1H), 3.12 (dd, J=10.6, 3.1 Hz, 1H), 0.92 (s, 9H), 0.84 (s, 9H), 0.09 (s, 3H), 0.08 (s, 3H), 0.04 (s, 3H), −0.12 (s, 3H).

$^{13}$C NMR (126 MHz, CDCl$_3$) δ 162.98, 143.82, 142.01, 128.79, 128.04, 127.33, 125.94, 116.35, 100.21, 86.98, 86.66, 73.83, 72.23, 63.43, 26.00, 25.86, 18.44, 18.17, −4.37, −4.39, −4.40, −4.73.

HRMS (ESI-TOF) m/z: [M+Na]$^+$ Calcd for C$_{42}$H$_{55}$NO$_7$Si$_2$Na 764.3415. Found 764.3413

β-Anomer $^1$H NMR (500 MHz, CDCl$_3$) δ 8.20 (d, J=9.2 Hz, 2H), 7.38-7.33 (m, 6H), 7.20-7.13 (m, 11H), 5.59 (d, J=1.4 Hz, 1H), 4.41 (dd, J=6.9, 4.1 Hz, 1H), 4.30 (dd, J=4.1, 1.4 Hz, 1H), 4.23 (ddd, J=6.9, 4.1, 2.6 Hz, 1H), 3.38 (dd, J=10.6, 2.7 Hz, 1H), 3.00 (dd, J=10.6, 4.2 Hz, 1H), 0.92 (s, 9H), 0.76 (s, 9H), 0.13 (s, 3H), 0.13 (s, 3H), 0.02 (s, 3H), −0.16 (s, 3H).

$^{13}$C NMR (126 MHz, CDCl$_3$) δ 162.09, 143.74, 142.27, 128.82, 127.75, 127.09, 125.87, 116.26, 105.06, 86.55, 83.33, 76.60, 71.64, 62.95, 25.92, 25.89, 18.26, 18.11, −3.99, −4.28, −4.38, −4.86.

HRMS (ESI-TOF) m/z: [M+Na]$^+$ Calcd for C$_{42}$H$_{55}$NO$_7$Si$_2$Na 764.3415. Found 764.3414.

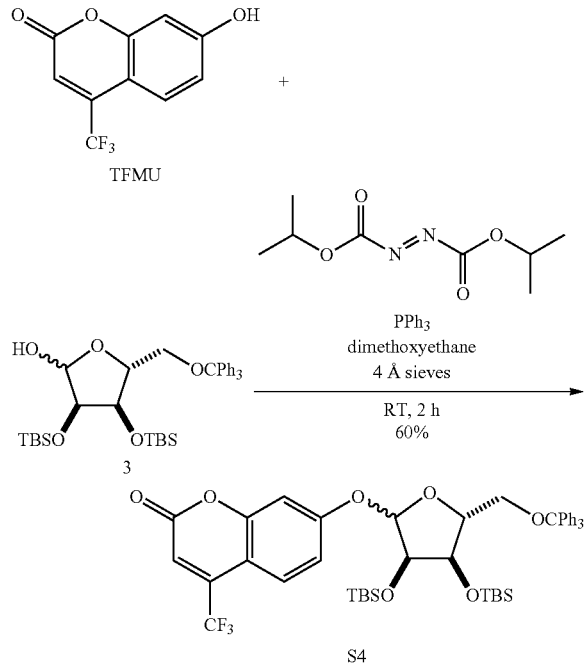

4-(trifluoromethyl)umbellifer-7-yl 2,3-bis-O-tert-butyldimethylsilyl-5-O-trityl-D-ribofuranoside (S4): A 100 mL round bottom flask was charged with 4-(trifluoromethyl) umbelliferone (1.69 g, 7.36 mmol, 1.5 eq), 2,3-di-(tert-butyldimethylsilyl)-5-(triphenylmethyl)-D-ribofuranose (3) (3.05 g, 4.91 mmol, 1 eq), triphenylphosphine (1.93 g, 7.37 mmol, 1.5 eq), and 4 Å molecular sieves (600 mg). Material was dissolved in dimethoxyethane (35 mL) and stirred for 15 min at room temperature. DIAD (1.45 mL, 7.36 mmol, 1.5 eq) was added dropwise. Reaction mixture was stirred at room temperature for 2 hours and then poured into hexane (400 mL). Resulting precipitate was removed by filtration. Filtrate was washed with satd aq NaHCO$_3$ 4×. Organic phase was dried over Na$_2$SO$_4$ and evaporated. Residue was purified by silica gel (5% Et$_2$O:hexane) to give S4 (2.47 g, 60%) as a mixture of anomers. While anomers were could be separated by silica gel chromatography, the mixture of diastereomers was routinely carried into the next step as they were more easily separable with the trityl group removed.

α-anomer $^1$H NMR (500 MHz, CDCl$_3$) δ 7.55 (dt, J=9.1, 1.9 Hz, 1H), 7.39-7.34 (m, 6H), 7.27-7.21 (m, 6H), 7.20-7.15 (m, 3H), 7.03 (d, J=2.3 Hz, 1H), 6.95 (dd, J=9.0, 2.4 Hz, 1H), 6.54 (s, 1H), 5.55 (d, J=4.2 Hz, 1H), 4.31 (dd, J=5.3, 4.3 Hz, 1H), 4.08 (q, J=3.1 Hz, 1H), 3.96 (dd, J=5.2, 1.9 Hz, 1H), 3.32 (dd, J=10.6, 3.4 Hz, 1H), 3.03 (dd, J=10.6, 3.1 Hz, 1H), 0.83 (s, 9H), 0.75 (s, 9H), −0.00 (s, 6H), −0.05 (s, 3H), −0.21 (s, 3H).

$^{13}$C NMR (126 MHz, CDCl$_3$) δ 161.79, 159.62, 156.25, 143.83, 141.75 (q, $^2J_{CF}$=32.8 Hz), 128.79, 128.07, 127.34, 126.43 (d, $^3J_{CF}$=2.3 Hz), 121.79 (q, $^1J_{CF}$=275.5 Hz), 114.85, 112.50 (q, $^3J_{CF}$=5.7 Hz), 107.61, 104.46, 100.23, 87.03, 86.87, 73.87, 72.25, 63.49, 26.01, 25.85, 18.44, 18.16, −4.37, −4.41, −4.43, −4.72.

$^{19}$F NMR (471 MHz, CDCl$_3$) δ −64.68.

β-Anomer $^1$H NMR (500 MHz, CDCl$_3$) δ 7.50 (dq, J=8.9, 1.8 Hz, 1H), 7.25-7.20 (m, 6H), 7.06-7.01 (m, 10H), 6.99 (dd, J=9.0, 2.5 Hz, 1H), 6.48 (s, 1H), 5.45 (d, J=1.3 Hz, 1H), 4.32 (dd, J=6.9, 4.0 Hz, 1H), 4.17 (dd, J=4.1, 1.4 Hz, 1H), 4.09 (dt, J=6.8, 3.3 Hz, 1H), 3.30 (dd, J=10.6, 2.8 Hz, 1H), 2.86 (dd, J=10.7, 3.8 Hz, 1H), 0.80 (s, 9H), 0.63 (s, 9H), 0.00 (s, 3H), 0.00 (s, 3H), −0.11 (s, 3H), −0.28 (s, 3H).

$^{13}$C NMR (126 MHz, CDCl$_3$) δ 160.98, 159.37, 156.10, 143.77, 141.55 (q, $^2J_{CF}$=32.7 Hz), 128.85, 127.75, 127.07, 126.43 (q, $^3J_{CF}$=2.4 Hz), 121.70 (q, $^1J_{CF}$=275.6 Hz), 114.14, 112.96 (q, $^3J_{CF}$=5.7 Hz), 107.92, 105.19, 104.79, 86.55, 83.32, 76.62, 71.46, 62.51, 25.93, 25.90, 18.27, 18.11, −3.98, −4.28, −4.37, −4.84.

$^{19}$F NMR (471 MHz, CDCl$_3$) δ −64.75.

HRMS (ESI-TOF) m/z: [M+Na]$^+$ Calcd for C$_{46}$H$_{55}$O$_7$F$_3$NaSi$_2$ 855.3336. Found 855.3342.

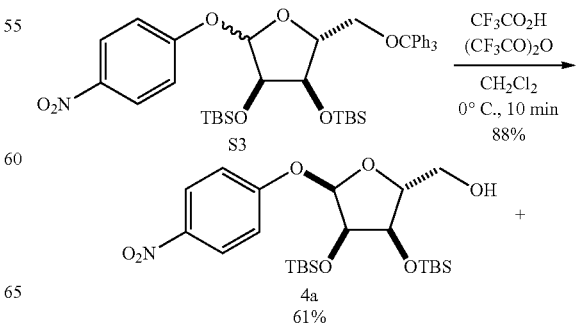

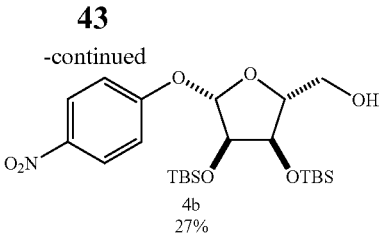

4b
27%

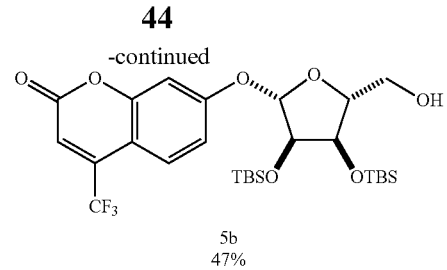

5b
47%

4-nitrophenyl 2,3-bis-O-tert-butyldimethylsilyl-D-ribofuranoside (4): To a stirring solution of compound S3 (5.26 g, 7.09 mmol, 1 eq) in dichloromethane (60 mL) at 0° C. was added trifluoroacetic anhydride (4.00 mL, 1.487 g/mL, 5.95 g, 28.3 mmol, 4 eq) as a 2 M solution in $CH_2Cl_2$ dropwise via addition funnel. Trifluoroacetic acid (1.6 mL, 1.489 g/mL, 2.38 g, 20.9 mmol, 3 eq) was added as a 2 M solution in $CH_2Cl_2$ dropwise via addition funnel. Reaction was stirred at room temperature for another 10 min. Reaction mixture was quenched with the addition of $Et_3N$ (4 mL, 0.7255 g/mL, 2.9 g, 29 mmol, 4.1 eq) followed by $CH_3OH$ (30 mL). Mixture was stirred for an additional 15 min at room temperature before being diluted with $H_2O$. Extracted three times with $CH_2Cl_2$. Combined organic layers were dried over $Na_2SO_4$ and concentrated in vacuo. Resulting residue was purified by silica gel chromatography (5:1 Hexane:EtOAc) to yield compound 4a (2.15 g, 61%) and compound 4b (0.96 g, 27%).

α-anomer (4a)

$^1$H NMR (500 MHz, $CDCl_3$) δ 8.17 (d, J=9.2 Hz, 2H), 7.10 (d, J=9.3 Hz, 2H), 5.60 (d, J=3.6 Hz, 1H), 4.20-4.15 (m, 3H), 3.81 (ddd, J=12.2, 4.5, 2.5 Hz, 1H), 3.67 (ddd, J=12.3, 7.0, 3.1 Hz, 1H), 1.94 (dd, J=7.4, 4.5 Hz, 1H), 0.91 (s, 18H), 0.12 (s, 3H), 0.09 (s, 3H), 0.07 (s, 6H).

$^{13}$C NMR (126 MHz, $CDCl_3$) δ 162.65, 142.13, 125.91, 116.34, 100.21, 86.99, 77.16, 73.96, 71.45, 62.32, 25.96, 25.90, 18.42, 18.20, −4.30, −4.39, −4.40, −4.71.

HRMS (ESI-TOF) m/z: [M+Na]$^+$ Calcd for $C_{23}H_{41}NNaO_7Si_2$ 522.2314. Found 522.2297

β-Anomer (4b)

$^1$H NMR (500 MHz, $CDCl_3$) δ 8.15 (d, J=9.2 Hz, 2H), 7.07 (d, J=9.2 Hz, 2H), 5.46 (d, J=1.3 Hz, 1H), 4.36 (dd, J=7.0, 4.1 Hz, 1H), 4.21 (dd, J=4.2, 1.3 Hz, 1H), 4.15 (dt, J=6.7, 3.1 Hz, 1H), 3.80 (ddd, J=12.5, 4.4, 2.7 Hz, 1H), 3.54 (ddd, J=12.4, 8.8, 3.5 Hz, 1H), 1.68 (dd, J=8.8, 4.3 Hz, 1H), 0.91 (s, 9H), 0.91 (s, 9H), 0.13 (s, 6H), 0.10 (s, 3H).

$^{13}$C NMR (126 MHz, $CDCl_3$) δ 161.52, 142.47, 125.92, 116.23, 105.00, 84.24, 77.16, 76.85, 70.72, 61.21, 25.94, 25.85, 18.20, 18.17, −4.15, −4.44, −4.46, −4.90.

HRMS (ESI-TOF) m/z: [M−H]$^−$ Calcd for $C_{23}H_{40}NO_7Si_2$ 498.2343. Found 498.2336

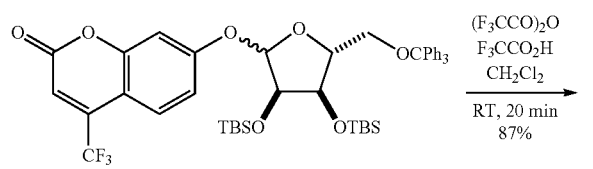

S4

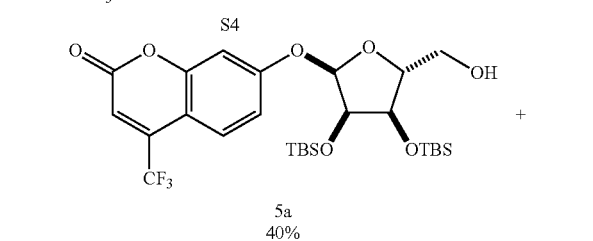

5a
40%

4-(trifluoromethyl)umbellifer-7-yl 2,3-bis-O-tert-butyldimethylsilyl-D-ribofuranoside (5): To a 100 mL-RBF equipped with addition funnel was added S4 (2.31 g, 2.77 mmol) and dichloromethane (24 mL). Trifluoroacetic anhydride (1.56 mL, 11.0 mmol, 4 eq) diluted with 5 mL of dichloromethane was added to stirring solution via addition funnel at room temperature. Trifluoroacetic acid (0.64 mL, 8.4 mmol, 3 eq) diluted with 5 mL of dichloromethane was added to stirring solution dropwise. Reaction mixture was stirred at room temperature for 20 min. Reaction mixture was neutralized by addition of neat triethylamine (5.0 mL, 36 mmol, 13 eq) via addition funnel followed by methanol (10 mL). Fuming mixture was stirred for 30 min and poured into satd aq $NH_4Cl$. Layers were separated, and aqueous layer extracted 3× with dichloromethane. Combined organic layers were dried over $Na_2SO_4$, filtered, and evaporated. Residue was purified by silica gel chromatography (6:1 hexane:EtOAc) to give separable anomers 5a (658 mg, 40%) and 5b (767 mg, 47%) as white solids.

α-anomer (5a)

$^1$H NMR (600 MHz, $CDCl_3$) δ 7.63 (dd, J=9.0, 1.8 Hz, 1H), 7.09 (d, J=2.4 Hz, 1H), 7.03 (dd, J=9.0, 2.4 Hz, 1H), 6.62 (s, 1H), 5.60 (d, J=3.7 Hz, 1H), 4.22-4.14 (m, 3H), 3.81 (dd, J=12.3, 2.7 Hz, 1H), 3.67 (dd, J=12.2, 3.1 Hz, 1Hf), 1.82 (bs, 1H), 0.920 (s, 9H), 0.918 (s, 9H), 0.12 (s, 3H), 0.09 (s, 3H), 0.08 (s, 3H), 0.08 (s, 3H).

$^{13}$C NMR (151 MHz, $CDCl_3$) δ 161.44, 159.55, 156.17, 141.73 (q, $^2J_{CF}$=32.72 Hz), 126.49 (q, $^3J_{CF}$=2.40 Hz), 121.74 (q, $^1J_{CF}$=275.62 Hz), 114.80, 112.68 (q, $^3J_{CF}$=5.68 Hz), 107.80, 104.46, 100.25, 87.04, 74.01, 71.45, 62.34, 25.98, 25.91, 18.44, 18.21, −4.29, −4.36, −4.37, −4.69.

$^{19}$F NMR (564 MHz, $CDCl_3$) δ −64.74.

HRMS (ESI-TOF) m/z: [M+H]$^+$ Calcd for $C_{27}H_{42}O_7F_3Si_2$ 591.2421. Found 591.2437.

β-Anomer (5b)

$^1$H NMR (500 MHz, $CDCl_3$) δ 7.64 (dd, J=8.9, 1.9 Hz, 1H), 7.06 (d, J=2.4 Hz, 1H), 7.01 (dd, J=9.0, 2.4 Hz, 1H), 6.65 (s, 1H), 5.47 (d, J=1.2 Hz, 1H), 4.38 (dd, J=7.2, 4.1 Hz, 1H), 4.21 (dd, J=4.1, 1.2 Hz, 1H), 4.17 (dt, J=7.2, 3.0 Hz, 1H), 3.86-3.79 (m, 1H), 3.56 (ddd, J=12.4, 9.1, 3.3 Hz, 1H), 1.46 (dd, J=9.1, 4.2 Hz, 1H), 0.93-0.92 (s, 18H), 0.14 (s, 9H), 0.12 (s, 3H).

$^{13}$C NMR (151 MHz, $CDCl_3$) δ 160.36, 159.23, 156.13, 141.54 (q, $^2J_{CF}$=32.82 Hz), 126.71 (q, $^3J_{CF}$=2.40 Hz), 121.69 (q, $^1J_{CF}$=275.34 Hz), 114.34, 113.23 (q, $^3J_{CF}$=5.66 Hz), 108.27, 105.14, 104.57, 84.23, 76.90, 76.68, 61.22, 25.99, 25.91, 18.28, 18.23, −4.08, −4.38, −4.41, −4.83.

$^{19}$F NMR (564 MHz, $CDCl_3$) δ −64.77.

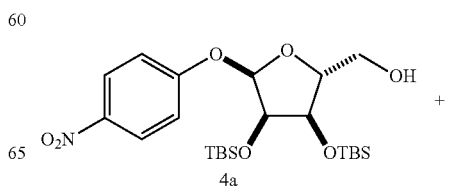

4a

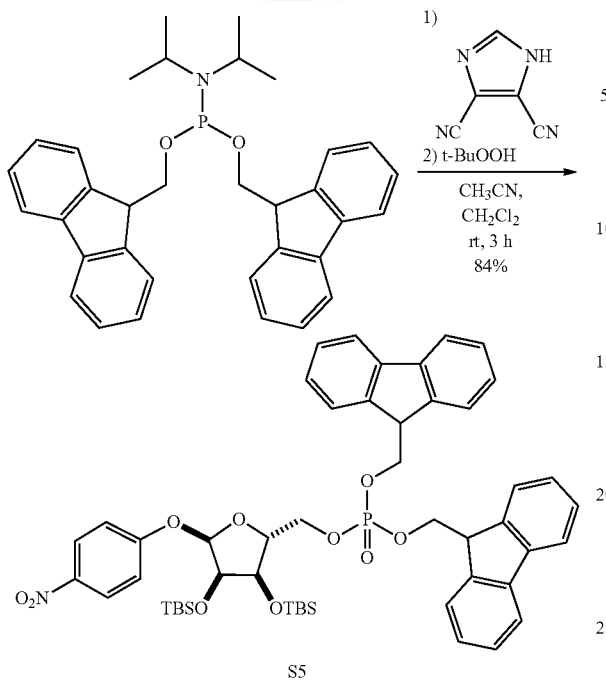

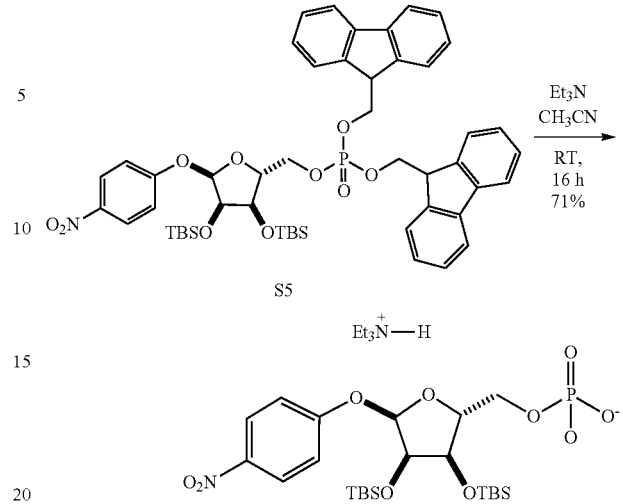

4-nitrophenyl 2,3-bis-O-tert-butyldimethylsilyl-α-D-ribose-5-(difluorenylmethyl phosphate) (S5): To a 20 mL reaction vial, 4a (71.1 mg, 0.142 mmol, 1 eq) and bis-(9H-fluoren-9-ylmethyl)-N,N-diisopropylamidophosphite (95.5 mg, 0.183 mmol, 1.3 eq) were added. Dissolved material by addition of $CH_2Cl_2$ (1.25 mL). Cooled solution to 0° C. 4,5-dicyanoimidazole (24.0 mg, 0.203 mmol, 1.4 eq) was added as a solution in acetonitrile (0.25 mL). After stirring at 0° C. for 15 min, mixture was allowed to warm to room temperature and was stirred for an additional 2 h. Once starting material was consumed as indicated by TLC (75:25 hexane:EtOAc), mixture was cooled to 0° C. and subjected to dropwise addition of tert-butyl hydroperoxide (0.14 mL, 0.70 mmol, 5 eq) as a 5 M solution in decane. Mixture was stirred for an additional 1 h and quenched with $H_2O$. Mixture was extracted with $CH_2Cl_2$ three times. Combined organic layers were dried over $Na_2SO_4$, concentrated, and purified by silica gel chromatography eluting with 60:40 hexane:EtOAc to yield compound S5 as a white foam (111.5 mg, 84%).

$^1$H NMR (500 MHz, $CDCl_3$) δ 8.00 (d, J=9.2 Hz, 2H), 7.77-7.70 (m, 4H), 7.57 (dd, J=18.2, 7.5 Hz, 2H), 7.52 (dd, J=7.3, 6.3 Hz, 2H), 7.44-7.34 (m, 4H), 7.32-7.24 (m, 4H), 6.91 (d, J=9.2 Hz, 2H), 5.26 (m, 1H), 4.38-4.26 (m, 4H), 4.22-4.12 (m, 3H), 4.06 (ddd, J=11.4, 5.8, 3.1 Hz, 1H), 4.04-4.00 (m, 2H), 3.91 (ddd, J=11.1, 7.0, 3.8 Hz, 1H), 0.91 (s, 9H), 0.90 (s, 9H), 0.11 (s, 3H), 0.05 (s, 3H), 0.03 (s, 6H).

$^{13}$C NMR (126 MHz, $CDCl_3$) δ 162.23, 143.16, 143.10, 142.98, 142.94, 142.10, 141.47, 141.44, 128.10, 128.08, 128.06, 127.27, 127.22, 125.78, 125.21, 125.17, 125.13, 125.07, 120.19, 120.18, 120.15, 116.09, 99.76, 83.93, 83.87, 77.16, 73.46, 71.13, 69.56, 69.51, 69.48, 69.43, 66.55, 66.51, 48.03, 48.00, 47.97, 47.93, 25.90, 25.86, 18.38, 18.12, −4.25, −4.37, −4.47, −4.80.

$^{31}$P NMR (202 MHz, $CDCl_3$) δ −0.41.

HRMS (ESI-TOF) m/z: [M+Na]$^+$ Calcd for $C_{51}H_{62}NO_{10}NaSi_2P$ 958.3548. Found 958.3554.

Triethylammonium 4-nitrophenyl 2,3-bis-O-tert-butyldimethylsilyl-α-D-ribose-5-phosphate (6): 20 mL reaction vial was charged with compound S5 (464 mg, 0.50 mmol, 1 eq). Added acetonitrile (5 mL) and triethylamine (freshly distilled from $CaH_2$, 1 mL) successively. Stirred at room temperature for 16 h. Added 1 mL toluene to stirring solution and concentrated in vacuo. Residue was redissolved in methanol (0.5 mL) and purified by C-18 chromatography to yield the triethylammonium salt of compound 6 as a tan foam (241 mg, 71%).

$^1$H NMR (500 MHz, $CD_3OD$) δ 8.20 (d, J=9.3 Hz, 2H), 7.17 (d, J=9.3 Hz, 2H), 5.71 (d, J=4.2 Hz, 1H), 4.39 (dd, J=5.4, 4.2 Hz, 1H), 4.31 (dd, J=5.4, 2.3 Hz, 1H), 4.20 (dq, J=3.9, 1.9 Hz, 1H), 3.99 (ddd, J=10.1, 4.4, 3.1 Hz, 1H), 3.95 (ddd, J=9.1, 4.6, 3.4 Hz, 1H), 3.17 (q, J=7.3 Hz, 6H), 1.31 (t, J=7.3 Hz, 9H), 0.94 (s, 9H), 0.93 (s, 9H), 0.16 (s, 3H), 0.13 (s, 3H), 0.13 (s, 3H), 0.10 (s, 3H).

$^{13}$C NMR (126 MHz, $CD_3OD$) δ 164.14, 143.13, 126.62, 117.36, 101.35, 87.69 (d, J=8.9 Hz), 74.75, 73.14, 65.98 (d, J=5.2 Hz), 47.40, 26.49, 26.46, 19.15, 18.96, 9.11, −4.10, −4.31 (2C), −4.43.

$^{31}$P NMR (202 MHz, $CD_3OD$) δ 0.77.

HRMS (ESI-TOF) m/z: [M−H]$^-$ Calcd for $C_{23}H_{41}NO_{10}PSi_2$ 578.2012. Found 578.2017.

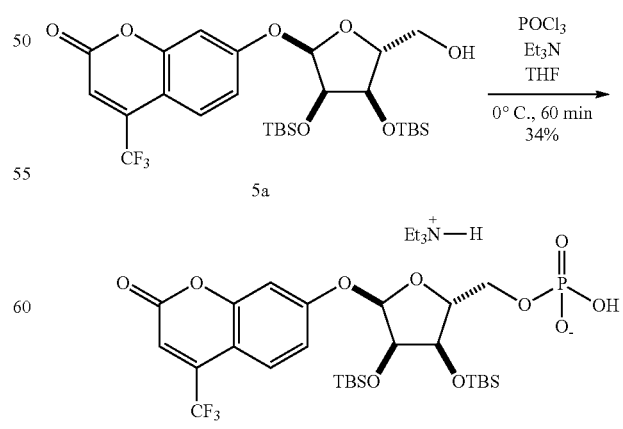

Triethylammonium 4-(trifluoromethyl)umbellifer-7-yl 2,3-bis-O-tert-butyldimethylsilyl-α-D-ribose-5-phosphate (7) (method A): To a stirring solution of 5a (507 mg, 0.858 mmol) in THF (8 mL) at 0° C. was added triethylamine (1.4 mL, 10 mmol, 12 eq) followed by phosphorus oxychloride (0.16 mL, 1.7 mmol, 2 eq). Reaction mixture was stirred at 0° C. for 40 min then warmed to room temperature and stirred for an additional 20 min. After cooling to 0° C. once again, reaction was quenched with addition of water (1 mL). Mixture was stirred for an additional 30 min at room temperature then solvent was removed by rotary evaporator. Residue was purified by C18 chromatography to give 7 (225 mg, 34%) as a white solid.

$^1$H NMR (500 MHz, CD$_3$OD) δ 7.68 (dd, J=8.8, 2.0 Hz, 1H), 7.12-7.06 (m, 2H), 6.71 (s, 1H), 5.72 (d, J=4.3 Hz, 1H), 4.41 (dd, J=5.4, 4.2 Hz, 1H), 4.32 (dd, J=5.4, 2.2 Hz, 1H), 4.21 (dq, J=3.9, 1.9 Hz, 1H), 4.01-3.91 (m, 2H), 3.19 (q, J=7.3 Hz, 6H), 1.31 (t, J=7.3 Hz, 9H), 0.95 (s, 9H), 0.93 (s, 9H), 0.16 (s, 3H), 0.14 (s, 6H), 0.11 (s, 3H).

$^{13}$C NMR (126 MHz, CD$_3$OD) δ 163.04, 160.83, 157.41, 142.36 (q, $^2J_{CF}$=32.30 Hz) 127.32 (q, $^3J_{CF}$=1.72 Hz), 123.22 (q, $^1J_{CF}$=274.75 Hz), 115.81, 113.88 (q, $^3J_{CF}$=5.81 Hz), 108.56, 105.05, 101.51, 87.94 (d, $^3J_{CF}$=9.1 Hz), 74.81, 73.20, 65.99 (d, $^2J_{CP}$=5.2 Hz), 47.56, 26.48f, 26.46, 19.16, 18.99, 9.15, −4.12, −4.34 (2C), −4.43.

$^{19}$F NMR (470 MHz, CD$_3$OD) δ −66.10.

$^{31}$P NMR (202 MHz, CD$_3$OD) δ 0.83.

HRMS (ESI-TOF) m/z: [M−H]$^-$ Calcd for C$_{27}$H$_{41}$F$_3$O$_{10}$PSi$_2$ 669.1933. Found 669.1918.

$^1$H NMR (500 MHz, CDCl$_3$) δ 7.76-7.68 (m, 4H), 7.58-7.46 (m, 5H), 7.43-7.32 (m, 4H), 7.31-7.22 (m, 5H), 6.95 (d, J=2.4 Hz, 1H), 6.86 (dd, J=9.0, 2.4 Hz, 1H), 6.61 (s, 1H), 5.34-5.30 (m, 1H), 4.34 (td, J=6.3, 1.4 Hz), 4.29 (ddt, J=9.9, 6.8, 3.7 Hz), 4.20-4.12 (m, 3H), 4.05-4.00 (m, 3H), 3.90 (ddd, J=11.1, 7.1, 3.8 Hz, 1H), 0.90 (s, 9H), 0.89 (s, 9H), 0.10 (s, 3H), 0.04 (s, 3H), 0.02 (s, 3H), 0.02 (s, 3H).

$^{13}$C NMR (126 MHz, CDCl$_3$) δ 161.13, 159.34, 156.03, 143.16 (d, J=11.6 Hz), 143.04 (d, J=9.6 Hz), 141.53 (q, $^2J_{CF}$=32.8 Hz), 141.52, 141.47, 128.07 (d, J=1.7 Hz), 127.28 (d, J=1.2 Hz), 127.26, 126.45 (q, $^3J_{CF}$=2.2 Hz), 125.22 (d, J=6.8 Hz), 125.16 (d, J=4.2 Hz), 121.72 (q, $^1J_{CF}$=275.5 Hz), 120.19 (d, J=1.9 Hz), 120.16, 114.20, 112.80 (q, $^3J_{CF}$=5.7 Hz), 107.81, 104.59, 99.82, 84.30 (d, J=7.4 Hz), 73.54, 71.26, 69.54 (t, J=5.7 Hz), 66.66 (d, J=5.8 Hz), 48.04 (dd, J=7.9, 5.7 Hz), 25.94, 25.88, 18.42, 18.15, −4.25, −4.36, −4.42, −4.74.

$^{19}$F NMR (471 MHz, CDCl$_3$) δ −64.71.

$^{31}$P NMR (203 MHz, CDCl$_3$) δ −1.55.

HRMS (ESI-TOF) m/z: [M+Na]$^+$ Calcd for C$_{55}$H$_{62}$O$_{10}$F$_3$NaSi$_2$P 1049.3469. Found 1049.3500.

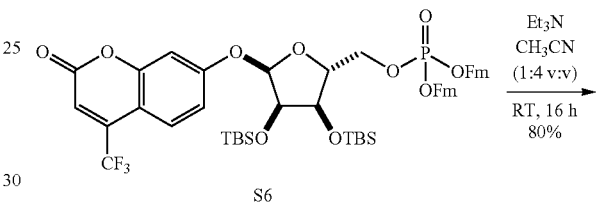

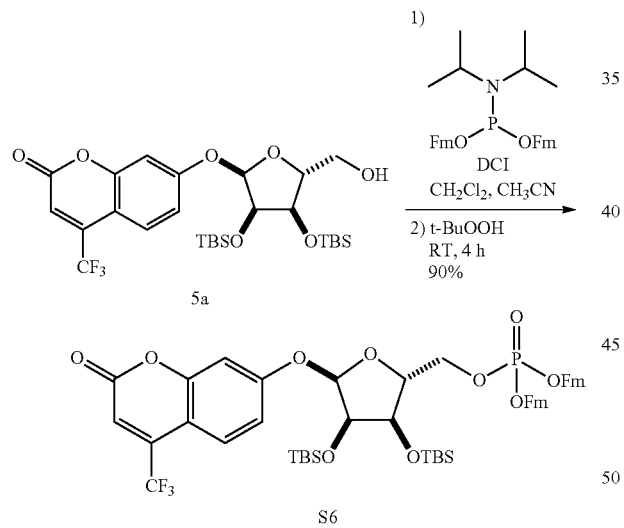

4-(trifluoromethyl)umbellifer-7-yl 2,3-bis-O-tert-butyldimethylsilyl-α-D-ribose-5-(difluorenylmethyl phosphate) (S6): To a stirring solution of compound 5a (373.9 mg, 0.633 mmol) and N,N-diisopropyl bis(9-methylfluorenyl)phosphoramidite (403.8 mg, 0.774 mmol) in CH$_2$Cl$_2$ (12 mL). Dicyanoimidazole (151 mg, 1.3 mmol) was added as a solution in acetonitrile (4.8 mL). Stirred at room temperature for 3 h. Reaction mixture was cooled to 0° C. added t-butylperoxide as a 5 M solution in decane (0.6 mL). Stirred at 0° C. for 1 h. Reaction mixture was quenched with water and extracted with CH$_2$Cl$_2$. Combined organic layers were dried over Na$_2$SO$_4$ and evaporated. Residue was purified by silica gel chromatography (1:1 hexane:EtOAc) to give compound S6 as a yellow foam (579.5 mg, 90%).

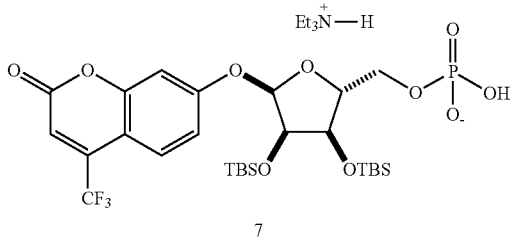

Triethylammonium 4-(trifluoromethyl)umbellifer-7-yl 2,3-bis-O-tert-butyldimethylsilyl-α-D-ribose-5-phosphate (7) (method B): To a stirring solution of compound S6 (1.18 g, 1.00 mmol) in acetonitrile (10 mL) was added Et$_3$N (freshly distilled from CaH$_2$, 2.5 mL). Mixture was stirred at room temperature for 16 h. Reaction mixture was co-evaporated with toluene to dryness. Residue was purified by C18 reverse phase chromatography to give compound 7 as a white solid (80%).

$^1$H NMR (500 MHz, CDCl$_3$) δ 7.57 (dt, J=9.0, 1.8 Hz, 1H), 7.04 (d, J=2.4 Hz, 1H), 7.00 (dd, J=9.0, 2.4 Hz, 1H), 6.56 (s, 1H), 5.54 (d, J=4.1 Hz, 1H), 4.25 (dd, J=5.4, 4.1 Hz, 1H), 4.22 (dd, J=5.4, 1.9 Hz, 1H), 4.16 (dt, J=4.0, 2.2 Hz, 1H), 3.98 (ddd, J=11.3, 5.4, 3.8 Hz, 1H), 3.93 (ddd, J=11.2, 5.6, 4.1 Hz, 1H), 3.06 (q, J=7.3 Hz, 6H), 1.30 (t, J=7.3 Hz, 9H), 0.86 (s, 9H), 0.86 (s, 9H), 0.07 (s, 3H), 0.04 (s, 3H), 0.03 (s, 3H), 0.02 (s, 3H).

$^{13}$C NMR (126 MHz, CDCl$_3$) δ 161.76, 159.58, 156.06, 141.72 (q, $^2J_{CF}$=32.6 Hz), 126.33 (q, $^3J_{CF}$=1.70 Hz), 121.66 (q, $^1J_{CF}$=275.6 Hz), 114.93, 112.20 (q, $^3J_{CF}$=5.7 Hz), 107.32, 104.07, 100.00, 86.72 (d, $^3J_{CP}$=8.6 Hz), 73.52, 71.66, 64.78 (d, $^2J_{CP}$=4.8 Hz), 45.47, 25.90, 25.84, 18.29, 18.08, 8.62, −4.46, −4.47, −4.49, −4.66.

$^{19}$F NMR (471 MHz, CDCl$_3$) δ −64.74.

$^{31}$P NMR (203 MHz, CDCl$_3$) δ 1.69.

HRMS (ESI-TOF) m/z: [M+Na]$^+$ Calcd for C$_{27}$H$_{42}$O$_{10}$NaPF$_3$Si$_2$ 693.1904. Found 693.1901.

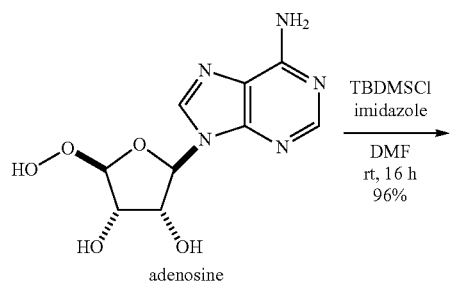

adenosine

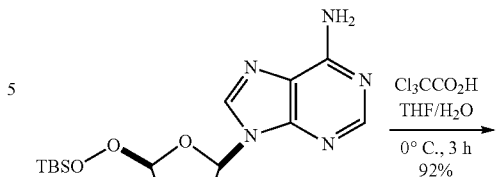

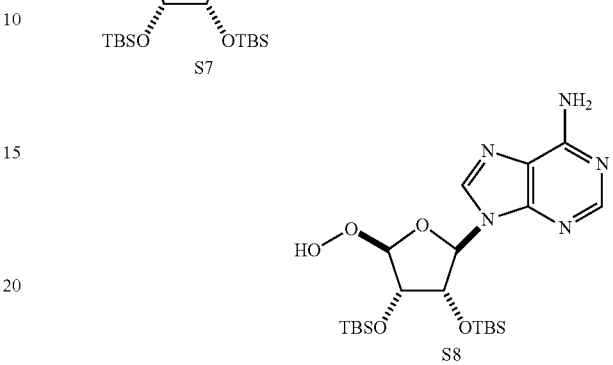

2',3',5'-tris-O-(tert-butyldimethylsilyl)-adenosine (S7): To a 100 mL round-bottom flask, adenosine (5.0 g, 19 mmol, 1 eq), imidazole (6.9 g, 102 mmol, 5.4 eq), and dimethylformamide (40 mL) were added. Once fully dissolved, solution was cooled to 0° C. Tert-butyldimethylsilyl chloride (12.2 g, 81 mmol, 4.2 eq) was added to the stirring solution. Once fully dissolved, reaction vessel was allowed to warm to room temperature. Stirred at room temperature for 16 h. Reaction was quenched by the addition of satd aq NH$_4$Cl. Extracted three times with CH$_2$Cl$_2$. Combined organic layers were dried over MgSO$_4$, filtered through a pad of celite, and evaporated. Residue was purified by silica gel chromatography eluting with 50:50 hexane:EtOAc to yield S7 as a white foam (12.5 g, 96%).

H NMR (500 MHz, CDCl$_3$) δ 8.32 (s, 1H), 8.15 (s, 1H), 6.11 (bs, 2H), 6.02 (d, J=5.2 Hz, 1H), 4.68 (t, J=4.8 Hz, 1H), 4.31 (t, J=3.9 Hz, 1H), 4.12 (q, J=3.5 Hz, 1H), 4.02 (dd, J=11.4, 4.2 Hz, 1H), 3.77 (dd, J=11.3, 2.9 Hz, 1H), 0.94 (s, 9H), 0.92 (s, 9H), 0.78 (s, 9H), 0.13 (s, 3H), 0.12 (s, 3H), 0.09 (s, 3H), 0.09 (s, 3H), −0.06 (s, 3H), −0.24 (s, 3H).

$^{13}$C NMR (126 MHz, CDCl$_3$) δ 155.70, 153.03, 150.05, 139.69, 120.19, 88.41, 85.58, 75.89, 72.11, 62.66, 26.20, 25.98, 25.81, 18.65, 18.22, 17.99, −4.28, −4.57, −4.59, −4.95, −5.24 (2C).

HRMS (ESI-TOF) m/z: [M+H]$^+$ Calcd for C$_{28}$H$_{56}$N$_5$O$_4$Si$_3$ 610.3640. Found 610.3647

2',3'-bis-O-(tert-butyldimethylsilyl)-adenosine (S8): A 500 mL round-bottom flask was charged with S7 (4.4 g, 7.2 mmol, 1 eq). Compound was dissolved in wet tetrahydrofuran (120 mL). Solution was cooled to 0° C. To vigorously stirring solution, trichloroacetic acid (56 g, 340 mmol, 47 eq) was added as an ice-cold solution in H$_2$O (25 mL). Stirred reaction mixture at 0° C. for 3 h. Quenched reaction by slowly cannulating reaction mixture into ice cold satd aq NaHCO$_3$. Once evolution of gas ceased, extracted three times with EtOAc. Dried organic layer over Na$_2$SO$_4$, filtered, and evaporated. Residue was purified by silica gel chromatography eluting with 95:5 CH$_2$Cl$_2$:CH$_3$OH to yield compound S8 as a white solid (3.3 g, 92%).

$^1$H NMR (500 MHz, 1:1 CDCl$_3$:DMSO (v:v)) δ 8.24 (s, 1H), 8.11 (s, 1H), 7.29 (s, 2H), 6.08 (dd, J=9.3, 3.3 Hz, 1H), 5.86 (d, J=7.1 Hz, 1H), 4.87 (dd, J=7.2, 4.5 Hz, 1H), 4.26 (dd, J=4.4, 1.4 Hz, 1H), 4.01 (q, J=2.1 Hz, 1H), 3.75 (dt, J=12.6, 3.2 Hz, 1H), 3.58 (ddd, J=12.1, 9.4, 2.6 Hz, 1H), 0.90 (s, 9H), 0.69 (s, 9H), 0.09 (s, 3H), 0.08 (s, 3H), −0.18 (s, 3H), −0.52 (s, 3H).

$^{13}$C NMR (126 MHz, 1:1 CDCl$_3$:DMSO (v:v)) δ 156.22, 151.89, 148.40, 140.12, 119.86, 88.45, 87.40, 73.99, 73.06, 61.60, 25.52, 25.33, 17.65, 17.36, −4.88, −4.97, −5.07, −6.02.

HRMS (ESI-TOF) m/z: [M+H]$^+$ Calcd for C$_{22}$H$_{42}$N$_5$O$_4$Si$_2$ 496.2775. Found 496.2774

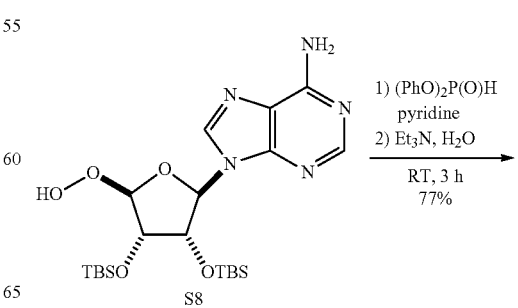

51

-continued

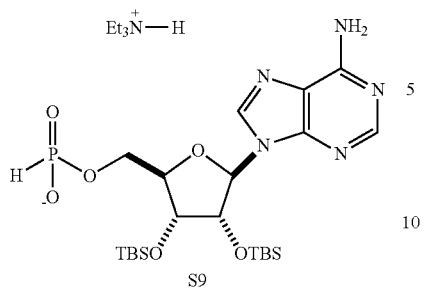

S9

Triethylammonium 2',3'-bis-O-(tert-butyldimethylsilyl)-adenosin-5'-yl H-phosphonate (S9): To a 20 mL reaction vial was added compound S8 (324 mg, 0.654 mmol, 1 eq). Added dry pyridine (6.5 mL). Once fully dissolved, diphenyl phosphite (0.65 mL, 1.22 g/mL, 795 mg, 3.4 mmol, 5 eq) was added, and reaction mixture was stirred at room temperature for 1.5 h. Then, water (0.5 mL) was added followed by triethylamine (0.5 mL). After stirring for an additional 30 min, the reaction mixture was concentrated and purified by C-18 chromatography to yield the triethylammonium salt of compound S9 as a white foam (331 mg, 77%).

$^1$H NMR (500 MHz, CD$_3$OD) δ 8.51 (s, 1H), 8.22 (s, 1H), 6.83 (d, $^1J_{HP}$=618.5 Hz, 1H), 6.10 (d, J=6.7 Hz, 1H), 4.87 (dd, J=6.7, 4.4 Hz, 1H), 4.41 (dd, J=4.4, 1.9 Hz, 1H), 4.21 (td, J=3.9, 2.1 Hz, 1H), 4.14 (ddd, J=11.0, 6.7, 4.2 Hz, 1H), 4.08 (ddd, J=11.4, 6.7, 3.8 Hz, 1H), 3.15 (q, J=7.3 Hz, 6H), 1.27 (t, J=7.3 Hz, 9H), 0.97 (s, 9H), 0.74 (s, 9H), 0.18 (s, 3H), 0.16 (s, 3H), −0.02 (s, 3H), −0.31 (s, 3H).

$^{13}$C NMR (126 MHz, CD$_3$OD) δ 157.20, 153.66, 151.00, 141.41, 120.32, 88.64, 86.71 (d, $^3J_{CP}$=8.1 Hz), 77.07, 74.49, 64.22 (d, $^2J_{CP}$=4.5 Hz), 47.61, 26.44, 26.24, 18.90, 18.68, 9.16, −4.17, −4.28 (2C), −5.08.

$^{31}$P NMR (202 MHz, CD$_3$OD) δ 4.14

HRMS (ESI-TOF) m/z: [M−H]$^−$ Calcd for C$_{22}$H$_{41}$N$_5$O$_6$PSi$_2$ 558.2338. Found 558.2323.

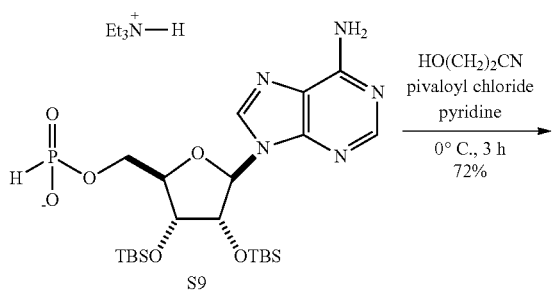

52

-continued

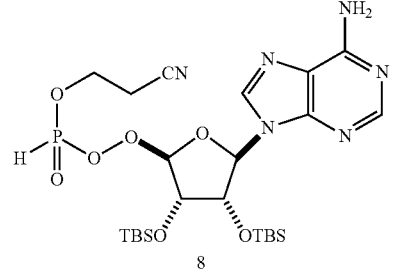

8

2',3'-bis-O-(tert-butyldimethylsilyl)-adenosin-5'-yl 2-cyanoethyl phosphonate (8): To a 25 mL round-bottom flask was added compound S9 (238 mg, 0.360 mmol, 1 eq). Dried material by co-azeotroping with dry acetonitrile three times. Pyridine was added (4 mL) and solution was cooled to 0° C. 3-hydroxypropionitrile (0.070 mL, 1.04 g/mL, 73 mg, 1.0 mmol, 3 eq) was added to stirring solution. Pivaloyl chloride (0.09 mL, 0.98 g/mL, 88 mg, 0.73 mmol, 2 eq) was added dropwise. After stirring at 0° C. for 2.5 h, reaction mixture was concentrated, azeotroping with toluene. Resulting residue was redissolved in acetonitrile and purified by C-18 chromatography to yield compound 8 as a white solid as a mixture of diastereomers (159 mg, 72%).

$^1$H NMR (500 MHz, CDCl$_3$) δ 8.30 (s, 1H), 8.30 (s, 1H), 8.00 (s, 1H), 7.98 (s, 1H), 6.91 (d, J=720.9 Hz, 1H), 6.83 (d, J=723.5 Hz, 1H) 6.50 (d, J=7.8 Hz, 2H), 5.87 (dd, J=5.8, 4.2 Hz, 2H), 4.89 (q, J=4.1 Hz, 2H), 4.52-4.14 (m, 10H), 2.72 (t, J=6.3 Hz, 2H), 2.69 (t, J=6.2 Hz, 2H), 0.90 (s, 9H), 0.90 (s, 9H), 0.80 (s, 18H), 0.10 (s, 3H), 0.09 (s, 3H), 0.09 (s, 3H), 0.08 (s, 3H), −0.03 (s, 6H), −0.19 (s, 3H), −0.19 (s, 3H).

$^{13}$C NMR (126 MHz, CDCl$_3$) δ 156.00, 155.96, 153.01, 149.52, 149.49, 140.14, 139.98, 120.54, 116.33, 89.94, 89.83, 82.60, 82.57, 82.55, 82.52, 77.16, 74.42, 74.33, 71.68, 71.60, 64.90, 64.85, 64.77, 64.73, 60.20, 60.16, 60.12, 60.08, 25.87, 25.76, 19.98, 19.93, 18.09, 17.94, −4.30, −4.31, −4.61, −4.63, −4.75, −4.76, −4.83, −4.85.

$^{31}$P NMR (202 MHz, CDCl$_3$) δ 8.70, 8.23.

HRMS (ESI-TOF) m/z: [M−H]$^−$ Calcd for C$_{25}$H$_{44}$N$_6$O$_6$PSi$_2$ 611.2604. Found 611.2594.

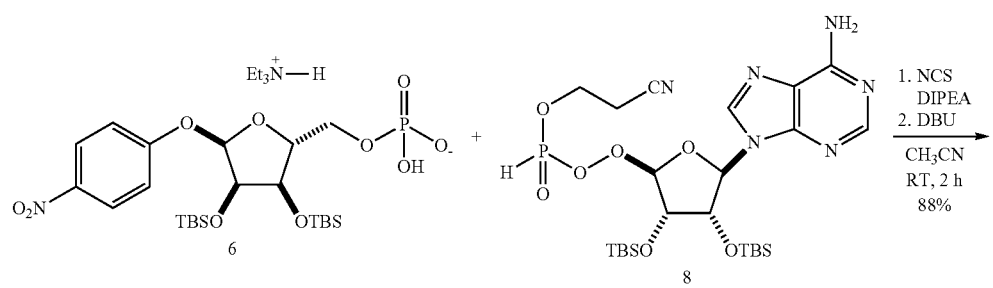

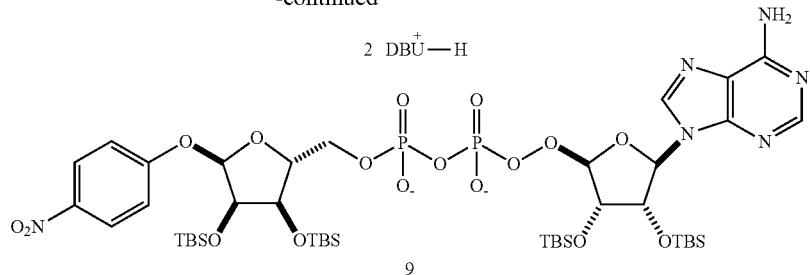

α-1"-O-(4-nitrophenyl)-2',2",3',3"-O-tetrakis-(tert-butyldimethylsilyl)-ADP-ribose (9): To a 20 mL reaction vial was added 6 (158.6 mg, 0.233 mmol, 1.0 eq) and 8 (138.3 mg, 0.226 mmol, 1.0 eq). Mixture was dried by co-azeotroping with dry acetonitrile three times and placing under vacuum over P$_2$O$_5$ for 12 h. The mixture was dissolved in acetonitrile (3.0 mL). Then, (i-Pr$_2$)$_2$NEt (129 mg, 1.00 mmol, 4.4 eq) and N-chlorosuccinimide (90.8 mg, 0.68 mmol, 3 eq) were sequentially added as 1 M solutions in acetonitrile and stirred at room temperature for 1 h. 1,8-diazabicycloundec-7-ene (350 mg, 2.3 mmol, 10 eq) was added as a 1 M solution in acetonitrile. After stirring for 30 min, reaction mixture was evaporated in vacuo and purified by C18 chromatography to yield compound 9 as a white foam (287 mg, 88%).

$^1$H NMR (500 MHz, CD$_3$OD) δ 8.67 (s, 1H), 8.18 (s, 1H), 8.14 (d, J=9.2 Hz, 2H), 7.11 (d, J=9.2 Hz, 2H), 6.15 (d, J=7.5 Hz, 1H), 5.64 (d, J=4.3 Hz, 1H), 4.85 (dd, J=7.5, 4.5 Hz, 1H), 4.46 (d, J=4.4 Hz, 1H), 4.37 (dd, J=5.4, 4.2 Hz, 1H), 4.35-4.27 (m, 3H), 4.21 (ddt, J=16.3, 4.3, 2.3 Hz, 2H), 4.11 (hept, J=5.7, 5.0 Hz, 2H), 3.58-3.53 (m, 4H), 3.50 (t, J=6.5, 1.7 Hz, 4H), 3.36 (t, J=5.6 Hz, 4H), 2.73-2.67 (m, 4H), 1.99 (pd, J=5.4, 1.3 Hz, 4H), 1.79-1.62 (m, 12H), 1.34 (d, J=6.5 Hz, 2H), 0.98 (s, 9H), 0.93 (s, 9H), 0.91 (s, 9H), 0.70 (s, 9H), 0.20 (s, 3H), 0.17 (s, 3H), 0.15 (s, 3H), 0.13 (s, 3H), 0.11 (s, 3H), 0.08 (s, 3H), −0.01 (s, 3H), −0.38 (s, 3H).

$^{13}$C NMR (126 MHz, CD$_3$OD) δ 167.42, 164.19, 157.30, 153.85, 151.17, 143.00, 141.66, 126.58, 120.04, 117.32, 101.23, 87.89, 87.86, 87.82, 87.64, 87.56, 77.60, 74.87, 74.76, 73.28, 66.76, 66.71, 66.66, 55.23, 49.53, 49.00, 39.34, 33.60, 30.01, 27.54, 26.49, 26.44, 26.21, 24.99, 20.43, 19.59, 19.14, 18.97, 18.93, 18.65, −4.07, −4.09, −4.19, −4.26, −4.29, −5.26.

$^{31}$P NMR (202 MHz, CD$_3$OD) δ −11.30 (d, J=21.8 Hz), −11.67 (d, J=21.6 Hz).

HRMS (ESI-TOF) m/z: [M−H]$^-$ Calcd for C$_{45}$H$_{81}$N$_6$O$_{16}$P$_2$Si$_4$ 1135.4267. Found 1135.4273.

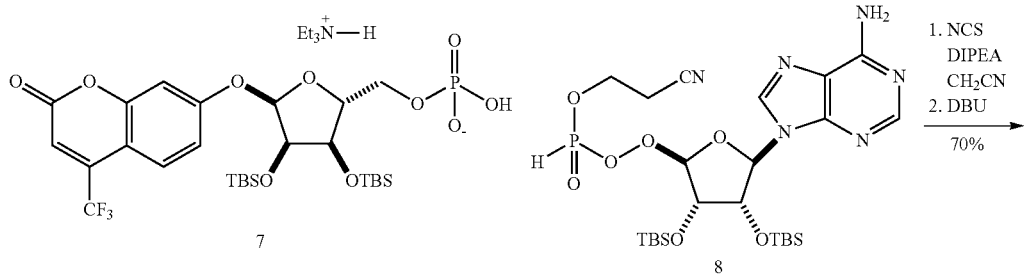

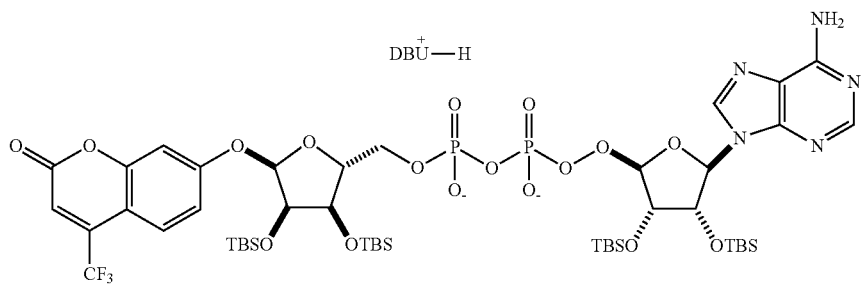

α-1"-O-(4-(trifluoromethyl)umbellifer-7-yl)-2',2",3',3"-O-tetrakis-(tert-butyldimethylsilyl)-ADP-ribose (10): To a stirring solution of 7 (95.8 mg, 0.124 mmol) and 8 (76.3 mg, 0.124 mmol) in dichloromethane (5 mL) was added DIPEA as a 1 M solution in $CH_3CN$ (0.74 mL, 0.74 mmol, 6 eq) and N-chlorosuccinimide as a 1 M solution in $CH_3CN$ (0.62 mL, 0.62 mmol, 5 eq). Mixture was stirred for 30 min at room temperature and then 1,8-diazabicycloundec-7-ene as a 1 M solution in THF (1 mL, 1 mmol, 8 eq) was added. After stirring for an additional 30 min, solvent was removed by rotavap. Residue was purified by C18 chromatography to give 10 (124 mg, 70%) as a white solid.

$^1$H NMR (500 MHz, $CD_3OD$) δ 8.29 (s, 1H), 7.81 (s, 1H), 7.24 (dd, J=8.9, 2.0 Hz, 1H), 6.65 (m, 2H), 6.29 (s, 1H), 5.73 (d, J=7.2 Hz, 1H), 5.27 (d, J=4.3 Hz, 1H), 4.42 (dd, J=7.2, 4.4 Hz, 1H), 4.05 (dd, J=4.4, 1.3 Hz, 1H), 3.99 (dd, J=5.4, 4.3 Hz, 1H), 3.95-3.87 (m, 3H), 3.85-3.80 (m, 2H), 3.75-3.70 (m, 2H), 3.18-3.14 (m, 1H), 3.11 (t, J=6.0 Hz, 2H), 2.96 (dd, J=10.1, 4.4 Hz, 2H), 2.91 (p, J=1.6 Hz, 1H), 2.80 (q, J=7.4 Hz, 3H), 2.33-2.27 (m, 2H), 1.60 (pd, J=5.5, 1.1 Hz, 2H), 1.38-1.24 (m, 4H), 0.97 (ddt, J=14.4, 9.2, 5.2 Hz, 22H), 0.57 (s, 9H), 0.54 (s, 9H), 0.51 (s, 9H), 0.31 (s, 9H), −0.21 (s, 3H), −0.24 (s, 3H), −0.25 (s, 3H), −0.28 (s, 3H), −0.29 (s, 3H), −0.31 (s, 3H), −0.41 (s, 3H), −0.77 (s, 3H).

$^{13}$C NMR (126 MHz, $CD_3OD$) δ 163.03, 160.75, 157.36, 153.02, 151.00, 142.21, 141.85, 127.28, 120.00, 115.77, 113.82, 108.45, 105.03, 101.34, 88.03, 87.46, 87.39, 77.72, 74.77, 73.27, 66.76, 66.63, 55.43, 55.25, 43.49, 39.35, 33.62, 30.00, 27.54, 26.49, 26.48, 26.22, 24.99, 20.43, 19.57, 19.14, 18.98, 18.92, 18.86, 18.65, 17.44, 13.05, 9.12, −4.09, −4.18, −4.20, −4.24, −4.28, −4.31, −5.21.

$^{19}$F NMR (470 MHz, $CD_3OD$) δ −66.37.

$^{31}$P NMR (202 MHz, $CD_3OD$) δ −10.38 (d, J=21.2 Hz), −10.80 (d, J=21.2 Hz).

HRMS (ESI-TOF) m/z: [M−H]$^-$ Calcd for $C_{49}H_{81}F_3N_5O_{16}P_2Si_4$ 1226.4188. Found 1226.4139.

pNP-ADPr (1): To a 25 mL round-bottom flask was added 9 (109.7 mg, 0.0761 mmol, 1 eq) and THF (3.0 mL). Once starting material was fully dissolve, triethylamine trihydrofluoride (0.5 mL) was added neat dropwise. Reaction vessel was sealed and heated to 65° C. Reaction was closely monitored by TLC (80:20 2-propanol:0.2% $NH_4OH_{(aq)}$) Once reaction had gone to completion, reaction mixture was cooled to room temperature and concentrated in vacuo. Remaining acid was quenched by dropwise addition of satd aq $NaHCO_3$. Aqueous solution of crude product was purified by C18 chromatography utilizing ion-pairing reagent in the mobile phase (10 mM $Et_3N$—HOAc, pH 7.0) to yield compound 1 as a triethylammonium salt. The triethylammonium salt was eluted through Dowex 50W-8X (ammonium-form) to give the ammonium salt of compound 1 as a white powder (53.8 mg, 98%).

$^1$H NMR (500 MHz, $D_2O$) δ 8.36 (s, 1H, Ade-2), 8.03 (s, 1H, Ade-8), 7.92 (d, J=9.2 Hz, 2H, pNP-3,5), 6.92 (d, J=9.2 Hz, 2H, pNP-2,6), 6.04 (d, J=5.7 Hz, 1H, Ade-1'), 5.67 (d, J=4.4 Hz, 1H, Rib-1"), 4.62 (t, J=5.7 Hz, 1H, Ade-2'), 4.46 (dd, J=5.1, 3.6 Hz, 1H, Ade-3'), 4.41 (dd, J=6.0, 4.6 Hz, 1H, Rib-2"), 4.36 (m, 2H, Ade-4', Rib-4"), 4.27 (dd, J=6.2, 2.6 Hz, 1H, Rib-3"), 4.23 (m, 2H, Ade-5'), 4.08 (m, 2H, Rib-5")

$^{13}$C NMR (126 MHz, $D_2O$) δ 161.8, 155.2, 152.5, 148.7, 141.5, 139.6, 125.6, 118.3, 116.3, 100.4, 86.8, 84.7, 83.8, 74.5, 71.3, 70.4, 69.7, 65.7, 65.3.

$^{31}$P NMR (202 MHz, $D_2O$) δ −11.2.

HRMS (ESI-TOF) m/z: [M−H]$^-$ Calcd for 679.0808. Found 679.0805.

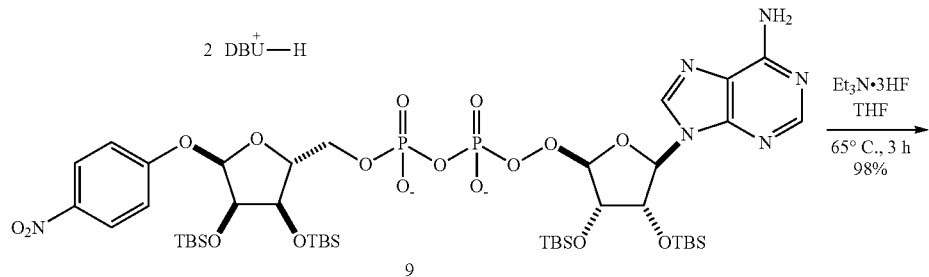

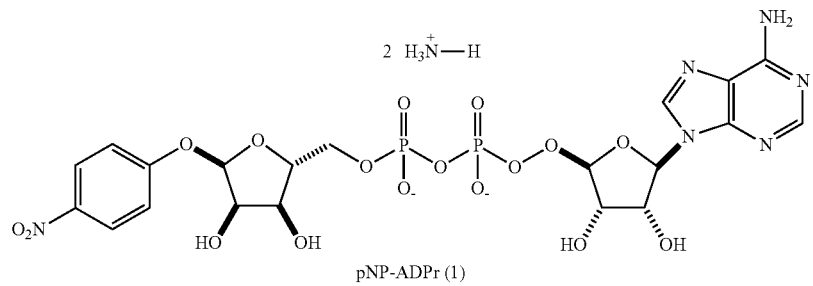

pNP-ADPr (1)

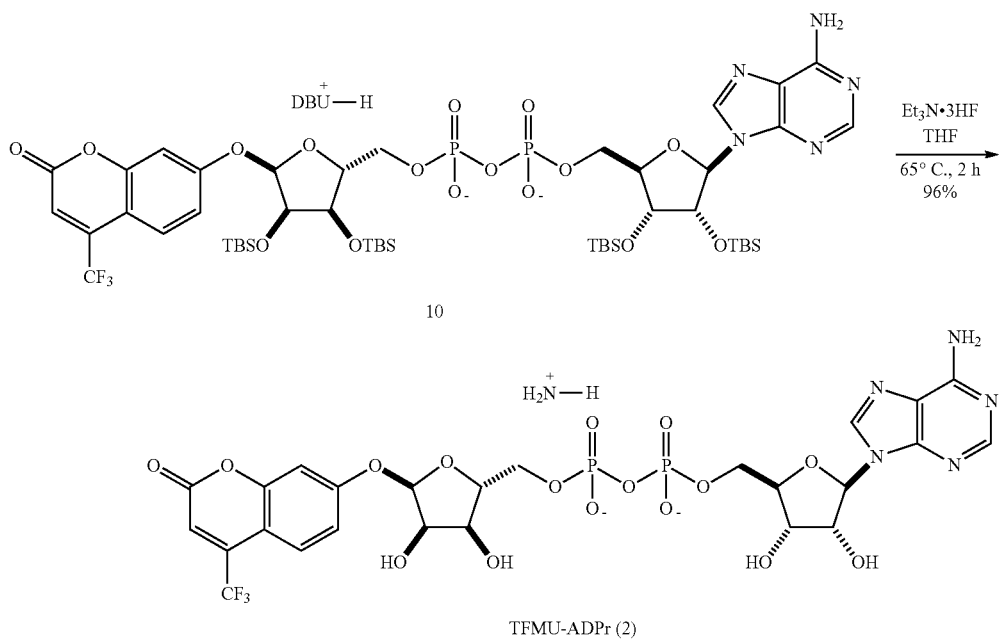

TFMU-ADPr (2)

TFMU-ADPr (2): To a stirring solution of 10 (67.2 mg, 0.044 mmol) in THF (1 mL) was added triethylamine trihydrofluoride (0.3 mL). Mixture was heated to 65° C. and stirred for 2 h. Once cooled to room temperature, reaction was quenched with addition of satd aq NaHCO$_3$. Aqueous mixture was purified by ion-pairing chromatography (10 mM Et$_3$N—HOAc, C$_{18}$) followed by ion exchange (Dowex 50W-8, ammonium form) to provide TFMU-ADPr (2) as a white solid (33.8 mg, 96%).

1H NMR (500 MHz, D$_2$O) δ 8.11 (s, 1H), 7.71 (s, 1H), 7.25 (dd, J=9.1, 1.8 Hz, 1H), 6.70 (dd, J=9.0, 2.5 Hz, 1H), 6.58 (d, J=2.5 Hz, 1H), 6.50 (s, 1H), 5.76 (d, J=5.6 Hz, 1H), 5.56 (d, J=4.5 Hz, 1H), 4.41 (t, J=5.3 Hz, 1H), 4.33-4.28 (m, 2H), 4.28-4.25 (m, 1H), 4.22 (q, J=4.1 Hz, 1H), 4.15 (dd, J=6.2, 2.8 Hz, 1H), 4.15-4.05 (m, 2H), 4.01 (ddd, J=11.5, 5.0, 3.0 Hz, 1H), 3.94 (dt, J=11.4, 4.4 Hz, 1H).

$^{13}$C NMR (126 MHz, D$_2$O) δ 161.71, 159.94, 154.33, 154.18, 151.56, 147.93, 141.37 (q, $^2J_{CF}$=32.8 Hz), 139.31, 125.98, 121.09 (q, $^1J_{CF}$=275.1 Hz), 117.67, 114.65, 112.35 (q, $^3J_{CF}$=4.3 Hz), 107.33, 103.50, 100.16, 86.90, 84.51 (d, $^3J_{CP}$=8.2 Hz), 83.42 (d, $^3J_{CP}$=8.3 Hz), 74.46, 71.13, 70.10, 69.57, 65.66 (d, $^2J_{CP}$=4.0 Hz), 65.11 (d, $^2J_{CP}$=4.2 Hz).

$^{19}$F NMR (471 MHz, D$_2$O) δ -64.43.

$^{31}$P NMR (203 MHz, D$_2$O) δ -11.08 (d, J=21.9 Hz), -11.28 (d, J=21.5 Hz).

HRMS (ESI-TOF) m/z: [M-H]$^-$ Calcd for C$_{25}$H$_{25}$F$_3$N$_5$O$_{16}$P$_2$ 770.0729; found 770.0723.

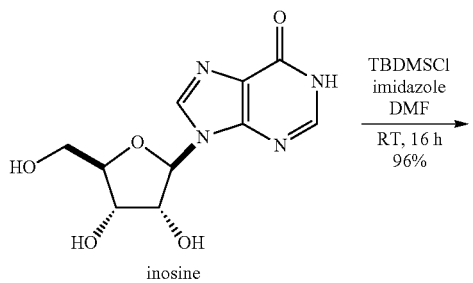

inosine

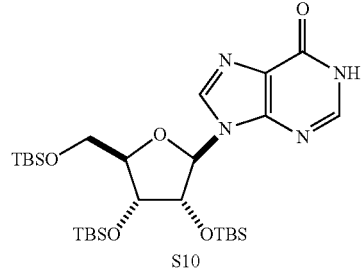

S10

2',3',5'-tris-O-(tert-butyldimethylsilyl)-inosine (S10): Intermediate was prepared according to a modified version of a previous report (Angew. Chem. Int. Ed. Engl. 2005, 44, 7305). Briefly, a 100 mL round-bottom flask was charged with inosine (1.0 g, 3.7 mmol, 1 eq) and imidazole (1.7 g, 25 mmol, 6.7 eq). Material was dissolved in dimethylformamide (4 mL). Tert-butyldimethylsilyl chloride (2.8 g, 18.7 mmol, 5 eq) was added in one portion. The solution was stirred at room temperature for 16 h. Reaction mixture was diluted with CH$_2$Cl$_2$ and quenched with the addition of satd aq NaHCO$_3$. Organic layer was washed two times with satd aq NaHCO$_3$, dried over Na$_2$SO$_4$, filtered through a pad of celite, and evaporated to give S10 as a white solid (2.2 g, 96%) which was used in subsequent reactions without further purification. $^1$H NMR spectrum was consistent with literature.

$^1$H NMR (500 MHz, CDCl$_3$) δ 12.94 (bs, 1H), 8.24 (s, 1H), 8.10 (s, 1H), 6.02 (d, J=4.9 Hz, 1H), 4.50 (t, J=4.6 Hz, 1H), 4.30 (t, J=4.0 Hz, 1H), 4.13 (q, J=3.4 Hz, 1H), 4.00 (dd, J=11.4, 3.7 Hz, 1H), 3.79 (dd, J=11.4, 2.5 Hz, 1H), 0.96 (d, J=0.7 Hz, 9H), 0.93 (d, J=0.7 Hz, 9H), 0.81 (d, J=0.7 Hz, 9H), 0.15 (s, 3H), 0.14 (s, 3H), 0.10 (s, 3H), 0.09 (s, 3H), -0.02 (s, 3H), -0.18 (s, 3H).

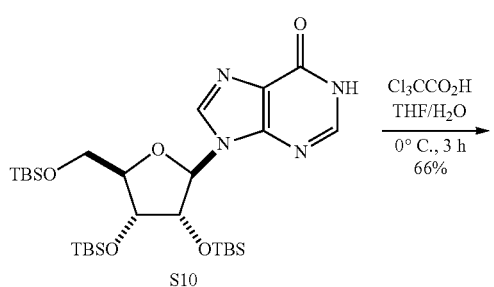

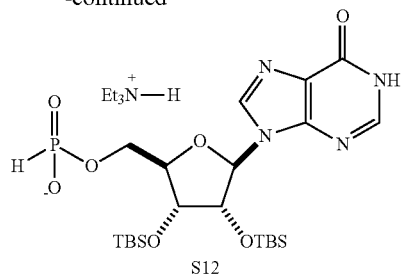

Triethylammonium 2',3'-bis-O-(tert-butyldimethylsilyl)-inosin-5'-yl H-phosphonate (S12): A 100 mL round-bottom flask was charged with S11 (420 mg, 0.85 mmol, 1 eq) and pyridine (8.5 mL). Diphenylphosphite (0.81 mL, 1.223 g/mL, 990 mg, 4.2 mmol, 5 eq) was added dropwise. After stirring reaction mixture at room temperature for 1.5 h, H$_2$O (0.5 mL) and triethylamine (0.5 mL) were added sequentially. Reaction was stirred for 30 min, then concentrated in vacuo. Remaining pyridine was removed by repeated azeotropic evaporation with toluene. Residue was purified by C18 chromatography to provide compound S12 as a white foam (464 mg, 83%).

$^1$H NMR (500 MHz, CD$_3$OD) δ 8.48 (s, 1H), 8.16 (s, 1H), 6.84 (d, J$_{HP}$=620.8 Hz, 1H), 6.07 (d, J=6.6 Hz, 1H), 4.83 (dd, J=6.5, 4.4 Hz, 1H), 4.41 (dd, J=4.4, 2.1 Hz, 1H), 4.24-4.20 (m, 1H), 4.20-4.14 (m, 1H), 4.12-4.05 (m, 1H), 3.23 (q, J=7.3 Hz, 6H), 1.30 (t, J=7.3 Hz, 9H), 0.96 (s, 9H), 0.77 (s, 9H), 0.17 (s, 3H), 0.15 (s, 3H), 0.00 (s, 3H), −0.27 (s, 3H).

$^{13}$C NMR (126 MHz, CD$_3$OD) δ 158.78, 150.22, 146.99, 140.81, 125.52, 89.00, 86.60 (d, J$_{CP}$=8.0 Hz), 77.09, 74.17, 64.05 (d, J=4.4 Hz), 47.49, 26.44, 26.26, 18.88, 18.67, 9.19, −4.18, −4.29, −4.31, −5.10.

$^{31}$P NMR (202 MHz, CD$_3$OD) δ 4.11.

HRMS (ESI-TOF) m/z: [M−H]$^-$ Calc for C$_{22}$H$_{41}$N$_4$O$_7$PSi$_2$ 559.2179. Found 559.2164.

2',3'-bis-O-(tert-butyldimethylsilyl)-inosine (S11): A 100 mL round-bottom flask was charged with S10 (1.2 g, 2.0 mmol, 1 eq). Compound was dissolved in tetrahydrofuran (31 mL). Solution was cooled to 0° C. To vigorously stirring solution, trichloroacetic acid (15 g, 92 mmol, 47 eq) was added as an ice-cold solution in H$_2$O (6.8 mL). Stirred reaction mixture at 0° C. for 3 h. Quenched reaction by slowly cannulating reaction mixture into satd aq NaHCO$_3$. Once evolution of gas ceased, extracted three times with EtOAc. Dried organic layer over Na$_2$SO$_4$, filtered, and evaporated. Residue was purified by silica gel chromatography eluting with 93:7 CH$_2$Cl$_2$:CH$_3$OH to yield compound S11 as a white solid (641 mg, 66%).

$^1$H NMR (500 MHz, CDCl$_3$) δ 13.34 (bs, 1H), 8.46 (s, 1H), 7.95 (s, 1H), 5.80 (d, J=7.7 Hz, 1H), 5.68 (bs, 1H), 4.87 (dd, J=7.8, 4.6 Hz, 1H), 4.31 (d, J=4.5 Hz, 1H), 4.16 (s, 1H), 3.93 (dd, J=12.9, 2.1 Hz, 1H), 3.72 (d, J=13.0 Hz, 1H), 0.94 (d, J=0.9 Hz, 9H), 0.75 (d, J=0.9 Hz, 9H), 0.12 (s, 3H), 0.11 (s, 3H), −0.12 (s, 3H), −0.52 (s, 3H).

$^{13}$C NMR (126 MHz, CDCl$_3$) δ 158.90, 147.87, 145.79, 141.04, 126.72, 91.05, 89.33, 74.79, 73.84, 62.91, 25.93, 25.80, 18.20, 17.92, −4.42, −4.46, −4.49, −5.70.

HRMS (ESI-TOF) m/z: [M+H]$^+$ Calc for C$_{22}$H$_{40}$N$_4$O$_5$Si$_2$ 497.2610. Found 497.2614.

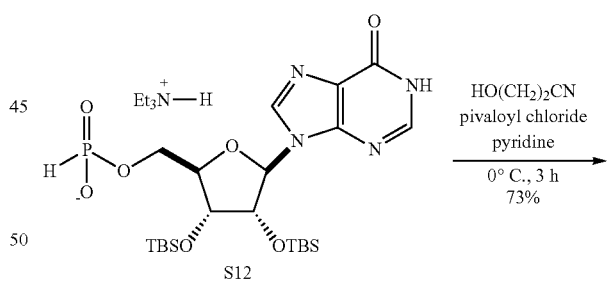

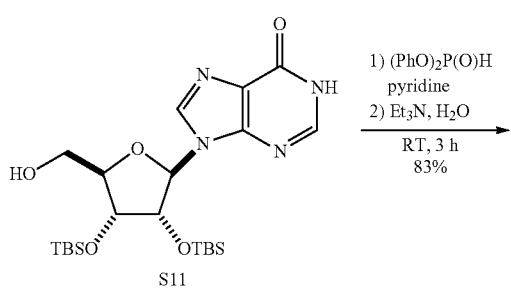

2',3'-bis-O-(tert-butyldimethylsilyl)-inosin-5'-yl 2-cyanoethyl phosphonate (11): To a 20 mL reaction vial was added compound S12 (246 mg, 0.372 mmol, 1 eq) and dry pyridine (4 mL). Solution was cooled to 0° C. 3-hydroxypropionitrile (0.070 mL, 1.04 g/mL, 73 mg, 1.0 mmol, 2.8 eq) was added to stirring solution. Pivaloyl chloride (0.09 mL, 0.98 g/mL, 88 mg, 0.73 mmol, 2 eq) was added dropwise. After stirring at 0° C. for 2.5 h, reaction mixture was concentrated, azeotroping with toluene. Resulting residue was redissolved in acetonitrile and purified by C-18 chromatography to yield compound 11 as a white solid as a mixture of diastereomers (166 mg, 73%).

$^1$H NMR (500 MHz, CDCl$_3$) δ 8.40 (s, 0.5H), 8.36 (s, 0.5H), 8.03 (s, 0.5H), 8.01 (s, 0.5H), 6.98 (d, J=722.4 Hz, 0.5H), 6.94 (d, J=722.1 Hz, 0.5H), 5.90 (dd, J=4.7, 3.2 Hz, 1H), 4.79 (t, J=4.5 Hz, 1H), 4.76 (t, J=4.0 Hz, 1H), 4.52-4.23 (m, 7H), 2.87-2.75 (m, 2H), 0.92 (s, 9H), 0.91 (s, 9H), 0.805 (s, 9H), 0.799 (s, 9H), 0.12 (s, 3H), 0.10 (s, 3H), 0.09 (s, 3H), −0.017 (s, 3H), −0.022 (s, 3H), −0.19 (s, 3H), −0.21 (s, 3H).

$^{13}$C NMR (126 MHz, CDCl$_3$) δ 159.03, 148.66, 148.64, 145.75, 145.68, 139.73, 139.53, 125.75, 125.69, 116.73, 116.60, 89.71, 89.64, 83.15, 83.10, 83.03, 82.97, 77.36, 74.94, 74.74, 71.73, 71.66, 64.55, 60.60, 60.56, 60.53, 25.87, 25.75, 20.17, 20.12, 20.08, 18.10, 17.94, −4.30, −4.56, −4.58, −4.69, −4.70, −4.90, −4.93.

$^{31}$P NMR (202 MHz, CDCl$_3$) δ 8.66, 8.41.

HRMS (ESI-TOF) m/z: [M−H]$^-$ Calc for C$_{25}$H$_{44}$N$_5$O$_7$PSi$_2$ 612.2444. Found 612.2448.

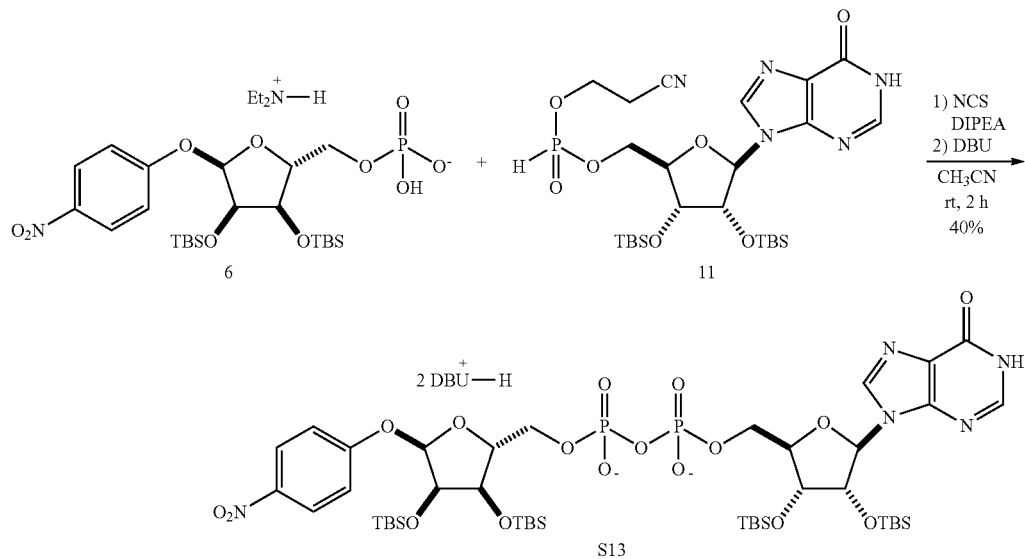

α-1''-O-(4-nitrophenyl)-2',2'',3',3''-O-tetrakis-(tert-butyldimethylsilyl)-IDP-ribose (S13): To a 20 mL reaction vial was added 6 (41.1 mg, 0.0604 mmol, 1.0 eq) and 11 (38.7 mg, 0.0630 mmol, 1.04 eq). Mixture was dried by co-azeotroping with dry acetonitrile three times and placing under vacuum over P$_2$O$_5$ for 12 h. The mixture was dissolved in acetonitrile (1.0 mL). Then, (i-Pr$_2$)$_2$NEt (31 mg, 0.24 mmol, 4.0 eq) and N-chlorosuccinimide (24 mg, 0.18 mmol, 3 eq) were sequentially added as 1 M solutions in acetonitrile and stirred at room temperature for 1 h. 1,8-diazabicycloundec-7-ene (92 mg, 0.6 mmol, 10 eq) was added as a 1 M solution in acetonitrile. After stirring for 30 min, reaction mixture was evaporated in vacuo and purified by C18 chromatography to yield compound S13 as a white foam (34.6 mg, 40%).

$^1$H NMR (500 MHz, CD$_3$OD) δ 8.55 (s, 1H), 8.14 (d, J=9.2 Hz, 2H), 8.08 (s, 1H), 7.12 (d, J=9.3 Hz, 2H), 6.08 (d, J=7.5 Hz, 1H), 5.66 (d, J=4.3 Hz, 1H), 4.46 (d, J=4.3 Hz, 1H), 4.39 (dd, J=5.4, 4.3 Hz, 1H), 4.35-4.28 (m, 3H), 4.23 (t, J=4.8 Hz, 1H), 4.19 (dt, J=4.3, 2.6 Hz, 1H), 4.15-4.07 (m, 2H), 3.64-3.56 (m, 4H), 3.53 (t, J=6.1 Hz, 4H), 3.36 (t, J=5.6 Hz, 4H), 2.74-2.65 (m, 4H), 2.02 (tdd, J=6.9, 5.2, 4.2 Hz, 4H), 1.82-1.66 (m, 14H), 0.97 (s, 9H), 0.93 (s, 9H), 0.91 (s, 9H), 0.73 (s, 9H), 0.20 (s, 3H), 0.17 (s, 3H), 0.15 (s, 3H), 0.13 (s, 3H), 0.11 (s, 3H), 0.08 (s, 3H), −0.00 (s, 3H), −0.36 (s, 3H).

$^{31}$P NMR (202 MHz, CD$_3$OD) δ −11.3 (d, J=21.9 Hz), −11.6 (d, J=21.8 Hz).

$^{13}$C NMR (126 MHz CD$_3$OD) δ 167.50, 164.28, 159.27, 150.61, 147.02, 143.00, 141.44, 126.59, 125.58, 117.36, 101.30, 88.57, 88.02 (d, J=9.2 Hz), 87.70 (d, J=9.3 Hz), 77.11, 74.81, 73.33, 66.71 (d, J=5.5 Hz), 66.52 (d, J=5.4 Hz), 55.33, 49.57, 39.37, 33.70, 30.01, 27.53, 26.50 (3C), 26.48, 26.22, 24.97, 20.44, 19.15, 18.99, 18.93, 18.68, −4.04, −4.11, −4.20, −4.23, −4.26, −4.30, −4.32, −5.32.

HRMS (ESI-TOF) m/z: [M−H]$^-$ Calc for C$_{45}$H$_{80}$N$_5$O$_{17}$P$_2$Si$_4$ 1136.4107. Found 1136.4115.

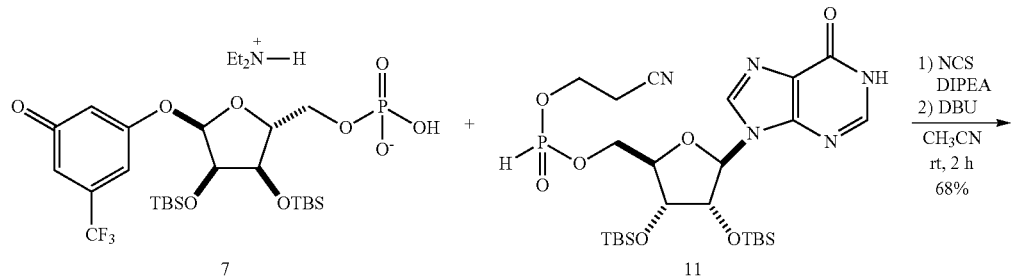

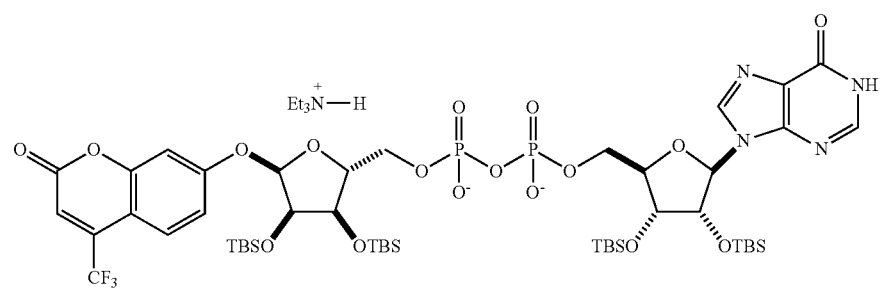

α-1''-O-(4-(trifluoromethyl)umbellifer-7-yl)-2',2'',3',3''-O-tetrakis-(tert-butyldimethylsilyl)-IDP-ribose (S14): To a stirring solution of 7 (93.6 mg, 0.121 mmol) and 11 (75.5 mg, 0.123 mmol) in dichloromethane (1 mL) was added DIPEA as a 1 M solution in CH$_3$CN (0.73 mL, 0.73 mmol, 6 eq) and N-chlorosuccinimide as a 1 M solution in CH$_3$CN (0.61 mL, 0.61 mmol, 5 eq). Mixture was stirred for 30 min at room temperature and then DBU as a 1 M solution in THF (1 mL, 1 mmol, 8 eq) was added. After stirring for an additional 30 min, solvent was removed by rotary evaporator. Residue was purified by C18 chromatography to give S14 (126 mg, 68%)

$^1$H NMR (500 MHz, CD$_3$OD) δ 8.56 (s, 1H), 8.09 (s, 1H), 7.65 (dd, J=9.6, 2.0 Hz, 1H), 7.05 (dd, J=6.8, 2.4 Hz, 3H), 6.70 (s, 1H), 6.07 (d, J=7.4 Hz, 1H), 5.70 (d, J=4.3 Hz, 1H), 4.89 (dd, J=7.4, 4.4 Hz, 1H), 4.44 (d, J=4.5 Hz, 1H), 4.40 (dd, J=5.4, 4.3 Hz, 1H), 4.35-4.25 (m, 6H), 4.22 (q, J=3.9 Hz, 4H), 4.12 (t, J=4.7 Hz, 3H), 3.72 (hept, J=6.7 Hz, 2H), 3.58 (m, 2H), 3.52 (t, J=5.9 Hz, 2H), 3.37 (t, J=5.7 Hz, 2H), 3.20 (q, J=7.4 Hz, 2H), 2.76-2.68 (m, 2H), 2.01 (pd, J=5.6, 1.3 Hz, 2H), 1.80-1.64 (m, 6H), 1.38 (t, J=7.2 Hz, 14H), 0.96 (s, 9H), 0.94 (s, 9H), 0.91 (s, 9H), 0.73 (s, 9H), 0.19 (s, 3H), 0.16 (s, 3H), 0.15 (s, 3H), 0.13 (s, 3H), 0.12 (s, 3H), 0.09 (s, 3H), −0.00 (s, 3H), −0.36 (s, 3H).

$^{13}$C NMR (126 MHz, CD$_3$OD) δ 167.45, 163.08, 160.79, 158.93, 157.38, 150.54, 146.83, 142.33 (q, $^2J_{CF}$=32.6 Hz), 141.41, 129.48, 127.29, 125.52, 123.23 (q, $^1J_{CF}$=274.9 Hz), 115.77, 113.81 (q, $^3J_{CF}$=6.4 Hz), 108.44, 105.04, 101.36, 88.59, 88.12 (d, $^3J_{CP}$=9.2 Hz), 87.55 (d, $^3J_{CP}$=9.4 Hz), 77.15, 74.79, 74.74, 73.31, 66.79 (d, $^2J_{CP}$=5.5 Hz), 66.54 (d, $^2J_{CP}$=5.4 Hz), 55.40, 55.27, 43.49, 39.36, 33.64, 30.04, 27.56, 26.49, 26.49, 26.47, 26.22, 25.00, 20.44, 19.57 (d, J=1.7 Hz), 19.15, 19.00, 18.92, 18.67, 13.11, −4.06, −4.10, −4.20, −4.22, −4.24, −4.30, −4.32, −5.29.

$^{31}$P NMR (203 MHz, CD$_3$OD) δ −11.41 (d, J=21.3 Hz), −11.81 (d, J=21.9 Hz).

HRMS (ESI-TOF) m/z: [M−H]$^−$ Cald for C$_{49}$H$_{80}$F$_3$N$_4$O$_{17}$P$_2$Si$_4$ 1227.4028. Found 1227.4056.

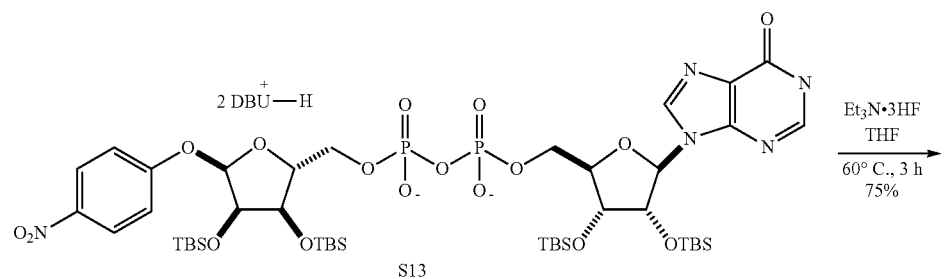

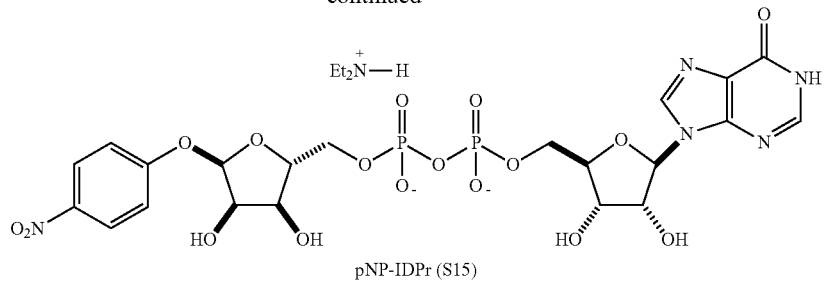

pNP-IDPr (S15)

pNP-IDPr (S15): To a 7 mL reaction vial was added S13 (17.4 mg, 0.0121 mmol, 1 eq) and THF (1.0 mL). Once starting material was fully dissolve, triethylamine trihydrofluoride (0.2 mL) was added neat dropwise. Reaction vessel was sealed and heated to 60° C. Reaction was closely monitored by TLC (80:20 2-propanol:0.2% $NH_4OH_{(aq)}$). Once reaction had gone to completion, reaction mixture was cooled to room temperature and concentrated in vacuo. Remaining acid was quenched by dropwise addition of satd aq $NaHCO_3$. Aqueous solution of crude product was purified by C-18 chromatography utilizing ion-pairing reagent in the mobile phase (10 mM $Et_3N$—HOAc) to yield compound pNP-IDPr (S15) as a triethylammonium salt. The triethylammonium salt was eluted through Dowex 50W-8X (ammonium-form) to give the ammonium salt of compound pNP-IDPr (S15) as a white powder (6.2 mg, 75%).

$^1$H NMR (500 MHz, $D_2O$) δ 8.37 (s, 1H), 8.09 (s, 1H), 8.06 (d, J=9.1 Hz, 2H), 7.06 (d, J=9.0 Hz, 2H), 6.06 (d, J=5.9 Hz, 1H), 5.79 (d, J=4.5 Hz, 1H), 4.70 (t, J=5.5 Hz, 1H), 4.50 (dd, J=5.2, 3.5 Hz, 1H), 4.45 (dd, J=6.2, 4.5 Hz, 1H), 4.42-4.37 (m, 2H), 4.31 (dd, J=6.0, 2.5 Hz, 1H), 4.29-4.22 (m, 2H), 4.16-4.05 (m, 2H).

$^{31}$P NMR (202 MHz, $D_2O$) δ −11.14 (d, J=21.8 Hz, 1P), −11.36 (d, J=21.6 Hz, 1P).

$^{13}$C NMR (from $^1$H, $^{13}$C-HMBC, 500 MHz, $D_2O$) 162.04, 158.43, 148.37, 146.14, 141.63, 139.60, 125.85, 123.59, 116.73, 100.32, 87.36, 84.78, 83.97, 74.53, 71.21, 70.38, 69.64, 65.57, 64.86.

HRMS (ESI-TOF) m/z: [M−H]$^-$ Calc for $C_{21}H_{24}N_5O_{17}P_2$ 680.0648. Found 680.0650.

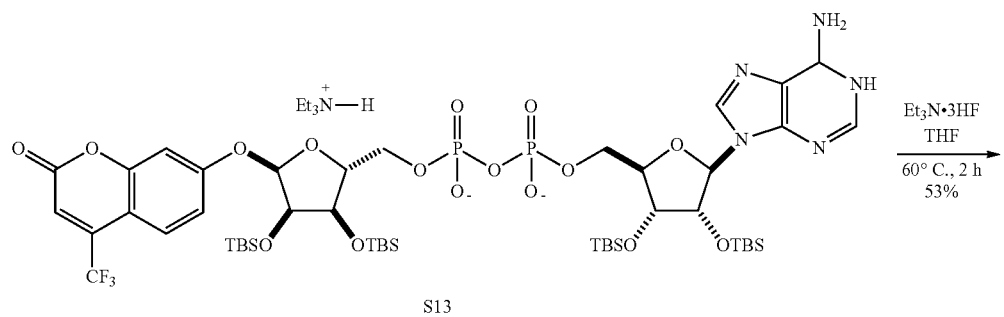

S13

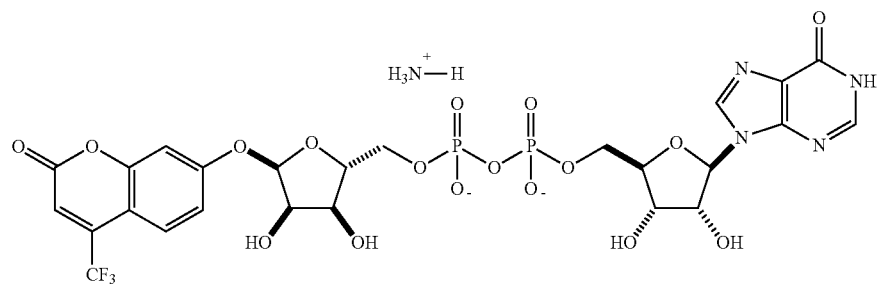

TFMU-IDPr (12)

TFMU-IDPr (12): To a stirring solution of S13 (119.9 mg, 0.78 mmol) in THF (1.0 mL) was added triethylamine trihydrofluoride (0.5 mL, 3.1 mmol, 40 eq). Reaction mixture was sealed with Teflon cap and heated to 60° C. After stirring at 60° C. for 2 h, solvent was removed by rotavap. Residue was neutralized with satd aq NaHCO$_3$ and aqueous mixture was purified by ion-pairing chromatography (10 mM Et$_3$N—HOAc, C18) followed by ion exchange (Dowex 50W-8, ammonium form) to provide TFMU-IDPr (12) (33.6 mg, 53%) as a white solid.

$^1$H NMR (500 MHz, D$_2$O) δ 8.27 (s, 1H), 7.96 (s, 1H), 7.48 (dd, J=9.1, 1.9 Hz, 1H), 6.93 (dd, J=9.0, 2.4 Hz, 1H), 6.85 (d, J=2.4 Hz, 1H), 6.70 (s, 1H), 5.95 (d, J=5.6 Hz, 1H), 5.77 (d, J=4.4 Hz, 1H), 4.61 (t, J=5.4 Hz, 1H), 4.49-4.42 (m, 2H), 4.44-4.39 (m, 1H), 4.37 (q, J=3.8 Hz, 1H), 4.30 (dd, J=6.3, 2.8 Hz, 1H), 4.28-4.21 (m, 2H), 4.16 (ddd, J=11.5, 5.1, 3.2 Hz, 1H), 4.09 (dt, J=11.3, 4.6 Hz, 1H).

$^{13}$C NMR (126 MHz, D$_2$O) δ 161.91, 160.21, 157.82, 154.77, 148.22, 145.93, 141.55 (q, $^2J_{CF}$=32.9 Hz), 139.48, 126.22, 123.33, 121.31 (q, $^1J_{CF}$=276.4, 275.8 Hz), 115.03, 112.72 (q, $^3J_{CF}$=8.2 Hz), 107.67, 103.87, 100.30, 87.54, 84.77 (d, $^3J_{CP}$=8.2 Hz), 83.86 (d, $^3J_{CP}$=8.5 Hz), 74.62, 71.32, 70.36, 69.71, 65.81 (d, $^2J_{CP}$=5.1 Hz), 65.29 (d, $^2J_{CP}$=5.3 Hz).

$^{31}$P NMR (202 MHz, D$_2$O) δ -11.09 (d, J=21.5 Hz), -11.31 (d, J=21.3 Hz).

$^{19}$F NMR (470 MHz, D$_2$O) δ -64.55.

HRMS (ESI-TOF) m/z: [M-H]$^-$ Calcd for C$_{25}$H$_{24}$F$_3$N$_4$O$_{17}$P$_2$ 771.0569. Found 771.0566.

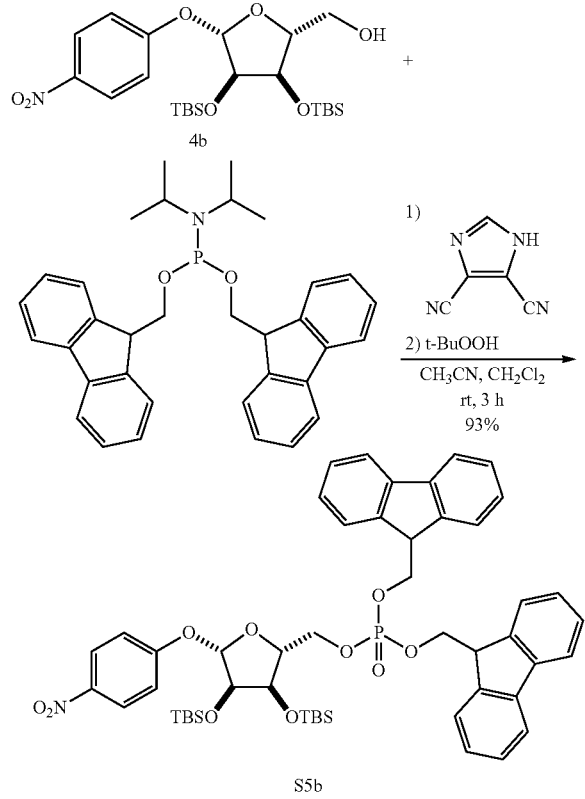

4-nitrophenyl 2,3-bis-O-tert-butyldimethylsilyl-D-D-ribose-5-(difluorenylmethyl phosphate) (S5b): To a 20 mL reaction vial, 4b (360.4 mg, 0.721 mmol, 1 eq) and bis-(9H-fluoren-9-ylmethyl)-N,N-diisopropylamidophosphite (488 mg, 0.936 mmol, 1.3 eq) were added. Dissolved material by addition of CH$_2$Cl$_2$ (11 mL). Cooled solution to 0° C. 4,5-dicyanoimidazole (129 mg, 1.1 mmol, 1.5 eq) was added as a solution in acetonitrile (2 mL). After stirring at 0° C. for 15 min, mixture was allowed to warm to room temperature and was stirred for an additional 2 h. Once starting material was consumed as indicated by TLC (75:25 hexane:EtOAc), mixture was cooled to 0° C. and subjected to dropwise addition of tert-butyl hydroperoxide (0.5 mL, 2.5 mmol, 3.5 eq) as a 5 M solution in decane. Mixture was stirred for an additional 1 h and quenched with H$_2$O. Mixture was extracted with CH$_2$Cl$_2$ three times. Combined organic layers were dried over Na$_2$SO$_4$, concentrated, and purified by silica gel chromatography eluting with 80:20 hexane:EtOAc to yield compound S5b as a white foam (628 mg, 93%).

$^1$H NMR (500 MHz, CDCl$_3$) δ 7.80 (d, J=9.2 Hz, 2H), 7.72 (dd, J=11.9, 7.5 Hz, 3H), 7.50-7.33 (m, 9H), 7.30-7.20 (m, 4H), 6.76 (d, J=9.2 Hz, 2H), 5.31 (m, 1H), 4.28 (dd, J=7.0, 4.0 Hz, 1H), 4.21-3.98 (m, 9H), 3.92 (dt, J=11.3, 4.0 Hz, 1H), 0.91 (s, 9H), 0.90 (s, 9H), 0.11 (s, 3H), 0.10 (s, 3H), 0.08 (s, 3H), 0.06 (s, 3H).

$^{13}$C NMR (126 MHz, CDCl$_3$) δ 161.50, 143.09, 143.07, 143.04, 142.22, 141.43, 141.40, 141.37, 128.07, 128.04, 127.22, 127.20, 127.18, 125.64, 125.20, 125.14, 125.12, 120.19, 120.16, 120.12, 116.01, 105.07, 81.77, 81.70, 76.53, 70.84, 69.47, 69.45, 69.42, 69.41, 65.74, 65.70, 48.02, 47.98, 47.96, 47.92, 25.95, 25.86, 18.21, 18.14, -4.10, -4.43, -4.44, -4.86.

$^{31}$P NMR (202 MHz, CDCl$_3$) δ -1.68.

HRMS (ESI-TOF) m/z: [M+Na]$^+$ Calcd for C$_{51}$H$_{62}$NO$_{10}$NaSi$_2$P 958.3548. Found 958.3540.

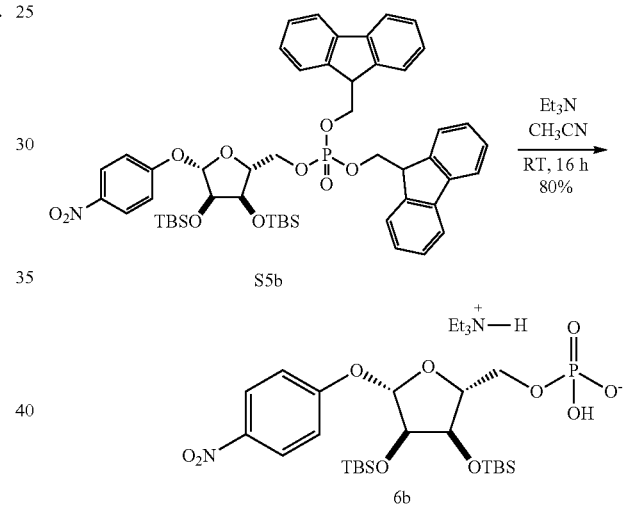

Triethylammonium 4-nitrophenyl 2,3-bis-O-tert-butyldimethylsilyl-β-D-ribose-5-phosphate (6b): 20 mL reaction vial was charged with compound S5b (551 mg, 0.59 mmol, 1 eq). Added acetonitrile (6 mL) and triethylamine (1.5 mL) successively. Stirred at room temperature for 16 h. Added 1 mL toluene to stirring solution and concentrated in vacuo. Residue was redissolved in methanol (0.5 mL) and purified by C-18 chromatography to yield the triethylammonium salt of compound 6b as a tan foam (322 mg, 80%).

$^1$H NMR (500 MHz, CD$_3$OD) δ 8.22 (d, J=9.2 Hz, 2H), 7.19 (d, J=9.3 Hz, 2H), 5.55 (d, J=3.0 Hz, 1H), 4.40 (dd, J=4.3, 3.0 Hz, 1H), 4.36 (t, J=4.3 Hz, 1H), 4.23 (dt, J=5.7, 4.4 Hz, 1H), 4.00 (dt, J=10.0, 4.7 Hz, 1H), 3.87-3.80 (m, 1H), 3.15 (q, J=7.3 Hz, 6H), 1.28 (t, J=7.3 Hz, 9H), 0.95 (s, 9H), 0.93 (s, 9H), 0.19 (s, 3H), 0.17 (s, 3H), 0.16 (s, 3H), 0.16 (s, 3H).

$^{13}$C NMR (126 MHz, CD$_3$OD) δ 163.55, 143.73, 126.70, 117.67, 106.77, 85.92 (d, J=9.2 Hz), 78.04, 73.84, 66.50 (d, J=4.8 Hz), 47.53, 26.46, 26.38, 19.05, 18.97, 9.11, -4.09, -4.17, -4.33, -4.52.

$^{31}$P NMR (202 MHz, CD$_3$OD) δ 0.66.

HRMS (ESI-TOF) m/z: [M-H]$^-$ Calcd for C$_{23}$H$_{41}$NO$_{10}$Si$_2$P 578.2007. Found 578.2009.

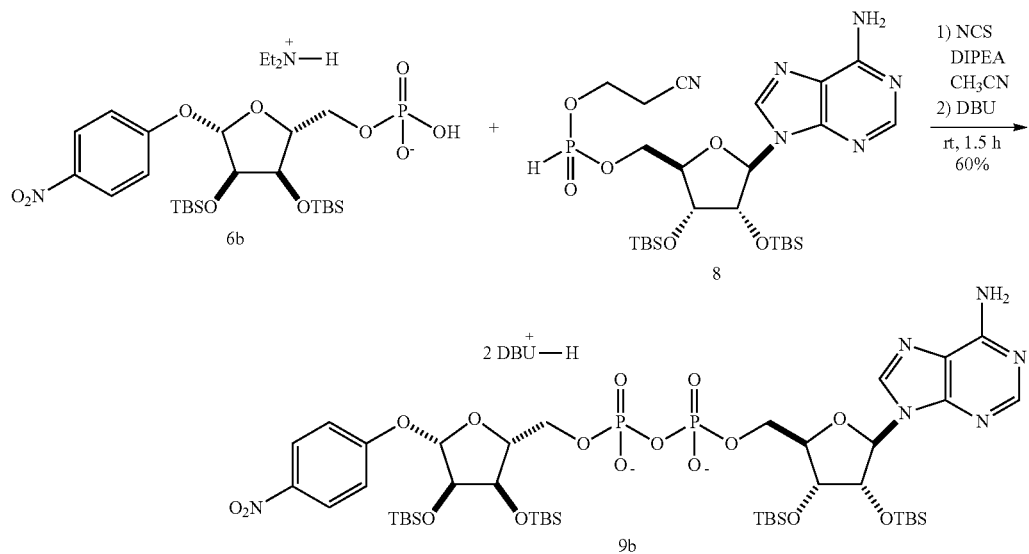

β-1''-O-(4-nitrophenyl)-2',2'',3',3''-O-tetrakis-(tert-butyldimethylsilyl)-ADP-ribose (9b): To a 20 mL reaction vial was added 6b (113.7 mg, 0.167 mmol, 1.0 eq) and 8 (110.0 mg, 0.179 mmol, 1.1 eq). Mixture was dried by co-azeotroping with dry acetonitrile three times and placing under vacuum over $P_2O_5$ for 12 h. The mixture was dissolved in acetonitrile (2.0 mL). Then, (i-$Pr_2$)$_2$NEt (64.6 mg, 0.5 mmol, 3 eq) and N-chlorosuccinimide (53.4 mg, 0.4 mmol, 2.4 eq) were sequentially added as 1 M solutions in acetonitrile and stirred at room temperature for 1 h. 1,8-diazabicycloundec-7-ene (350 mg, 2.3 mmol, 10 eq) was added as a 1 M solution in THF. After stirring for 30 min, reaction mixture was evaporated in vacuo and purified by C18 chromatography to yield compound 9b as a white foam (149.6 mg, 60%).

$^1$H NMR (500 MHz, CD$_3$OD) δ 8.64 (s, 1H), 8.173 (s, 1H), 8.172 (d, J=9.2 Hz, 2H), 7.15 (d, J=9.2 Hz, 2H), 6.10 (d, J=7.5 Hz, 1H), 5.51 (d, J=4.1 Hz, 1H), 4.80 (dd, J=7.5, 4.4 Hz, 1H), 4.45 (t, J=4.2 Hz, 1H), 4.42 (d, J=4.5, 1H), 4.38 (dd, J=4.4, 2.7 Hz, 1H), 4.26 (td, J=5.9, 2.8 Hz, 1H), 4.23 (m, 2H), 4.16 (m, 1H), 4.08 (qt, J=10.9, 5.5 Hz, 2H), 3.55 (m, 4H), 3.49 (t, J=5.9 Hz, 4H), 3.35 (m, 9H), 2.68 (m, 4H), 1.99 (m, 4H), 1.70 (m, 12H), 0.97 (s, 9H), 0.94 (s, 9H), 0.90 (s, 9H), 0.69 (s, 9H), 0.18 (s, 3H), 0.17 (s, 3H), 0.16 (s, 3H), 0.15 (s, 6H), 0.14 (s, 3H), −0.03 (s, 3H), −0.40 (s, 3H).

$^{13}$C NMR (126 MHz, CD$_3$OD) δ 167.45, 163.85, 157.31, 153.80, 151.17, 143.64, 141.65, 126.69, 120.02, 117.69, 107.14, 87.75, 87.63 (d, J=8.6 Hz), 86.75 (d, J=9.0 Hz), 78.21, 77.67, 74.85, 74.26, 66.86 (d, J=5.2 Hz), 66.68 (d, J=5.1 Hz), 55.25, 49.85, 49.54, 39.34, 33.62, 30.02, 27.55, 26.51, 26.48, 26.44, 26.21, 24.98, 20.43, 19.08, 18.99, 18.92, 18.64, −4.08, −4.13, −4.19, −4.21, −4.26, −4.29, −5.29.

$^{31}$P NMR (202 MHz, CD$_3$OD) δ −11.44 (d, J=21.5 Hz), −11.65 (d, J=21.5 Hz).

HRMS (ESI-TOF) m/z: [M−H]$^-$ Calcd for $C_{45}H_{82}N_6O_{16}P_2Si_4$ 1135.4267. Found 1135.4272.

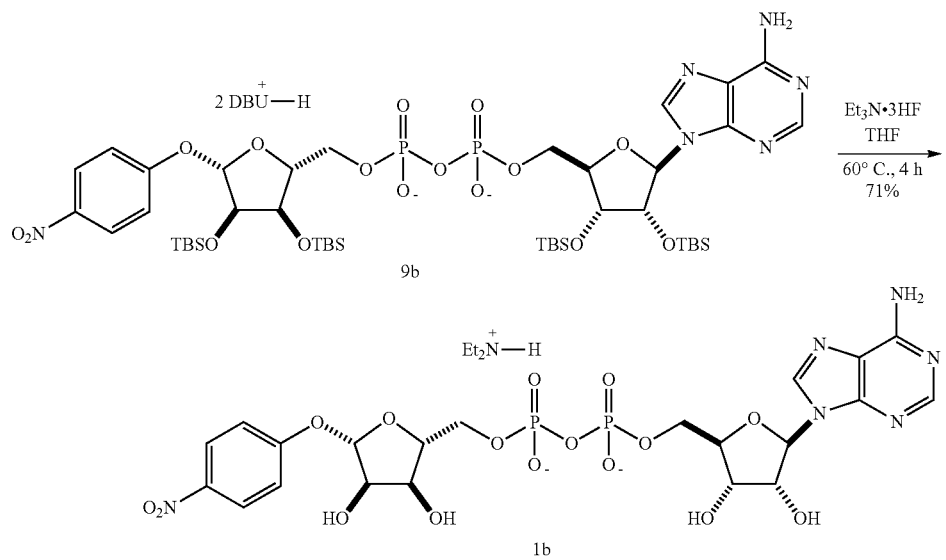

β-pNP-ADPr (1b): To a 20 mL reaction vial was added 9b (24.1 mg, 0.0167 mmol, 1 eq) and THF (1 mL). Triethylamine trihydrofluoride (0.1 mL, 0.989 g/mL) was added dropwise to stirring solution. Reaction vessel was sealed and heated to 60 C for 4 h. Reaction was closely monitored by TLC (80:20 2-propanol:0.2% NH$_4$OH(aq)) Once reaction had gone to completion, reaction mixture was cooled to room temperature and concentrated in vacuo. Remaining acid was quenched by dropwise addition of satd aq NaHCO$_3$. Aqueous solution of crude product was purified by C18 chromatography utilizing ion-pairing reagent in the mobile phase (10 mM Et$_3$N—HOAc, pH 7.0) to yield compound 1b as a triethylammonium salt. The triethylammonium salt was eluted through Dowex 50W-8X (ammonium-form) to give the ammonium salt of compound 1b as a white powder (8.5 mg, 71%).

$^1$H NMR (500 MHz, D$_2$O) δ 8.33 (s, 1H), 8.11 (s, 1H), 7.94 (d, J=9.3 Hz, 2H), 6.93 (d, J=9.4 Hz, 2H), 5.99 (d, J=5.4, 1H), 5.64 (d, J=1.0 Hz, 1H), 4.62 (t, J=5.2 Hz, 1H), 4.46 (m, 2H), 4.34 (m, 2H), 4.29 (td, J=5.9, 4.1 Hz, 1H), 4.19 (m, 2H), 4.16 (q, J=3.9 Hz, 1H), 4.08 (m, 1H).

$^{13}$C NMR (126 MHz, D$_2$O) δ 181.63, 161.38, 155.43, 152.74, 148.68, 141.68, 139.53, 125.67, 118.51, 116.45, 105.24, 87.17, 83.80, 82.78, 74.68, 70.70, 70.32, 66.69, 65.14.

$^{31}$P NMR (202 MHz, D$_2$O) δ -10.19.

HRMS (ESI-TOF) m/z: [M–H]$^-$ Calcd for C$_{21}$H$_{26}$N$_6$O$_{16}$P$_2$ 679.0808. Found 679.0809.

Example 3. PARG or ARH3 Substrates Comprising Linkers

Substrates with a Quinone Methide Linker

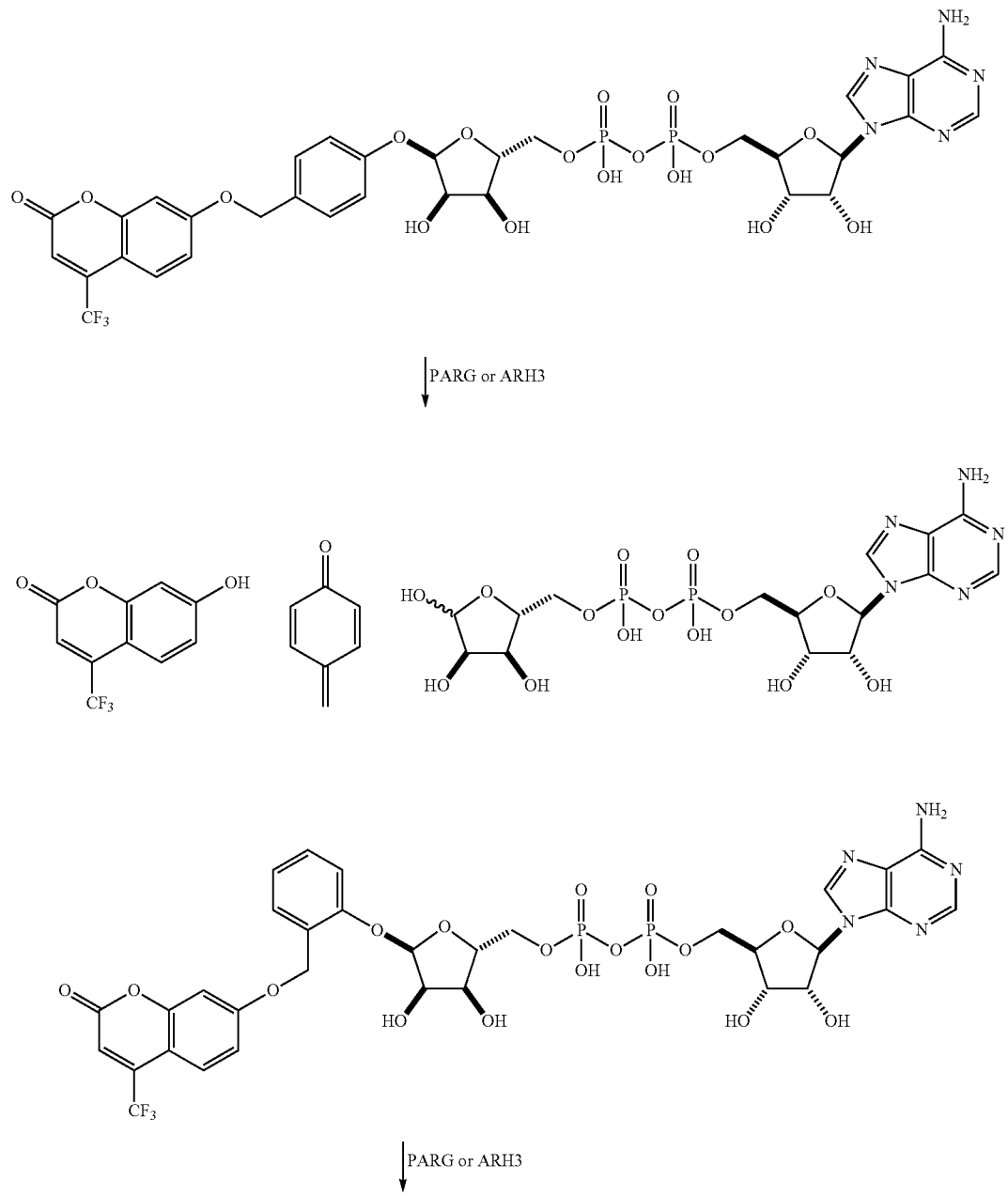

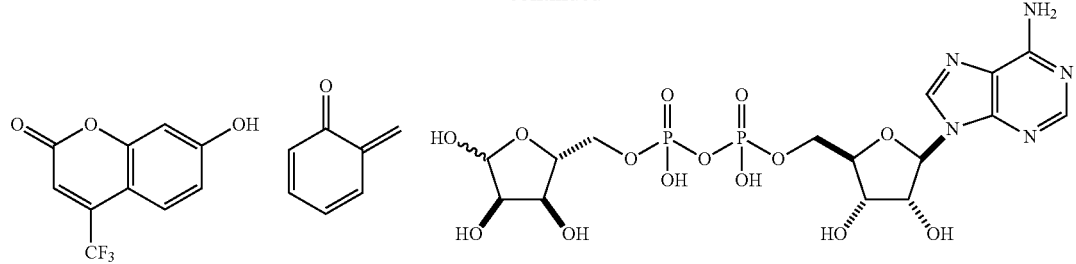

Application to Bulky Fluorophores

Fluorophores that are too bulky (e.g. the NIR probe QCy7) to be recognized as substrates by PARG or ARH3 can be used with the shown linker.

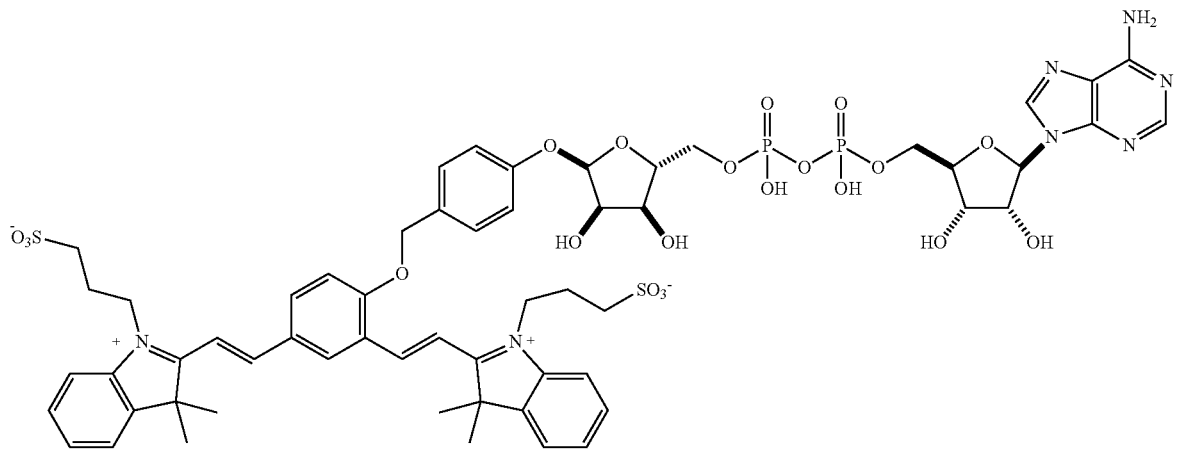

Application to Aniline Dyes

N-glycosides are not cleaved by PARG or ARH3, precluding the use of aniline-containing probes. These probes shown below can be used by incorporating a quinone methide linker with carbamate. The principle advantage of these probes is improved pH stability.

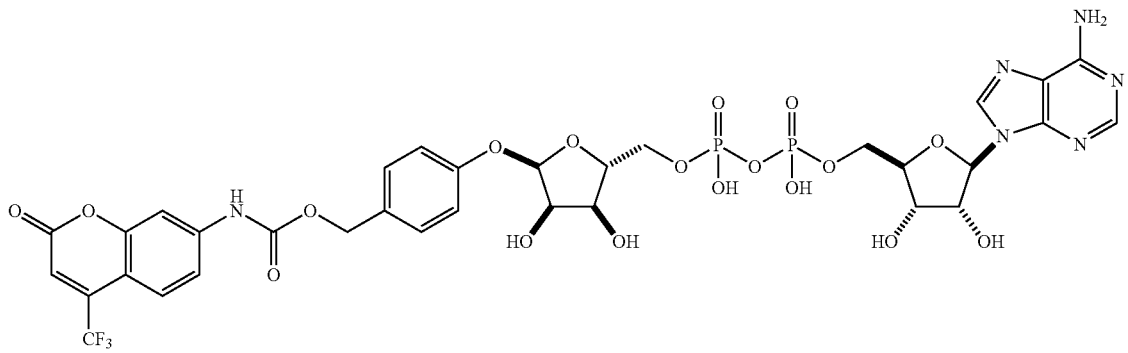

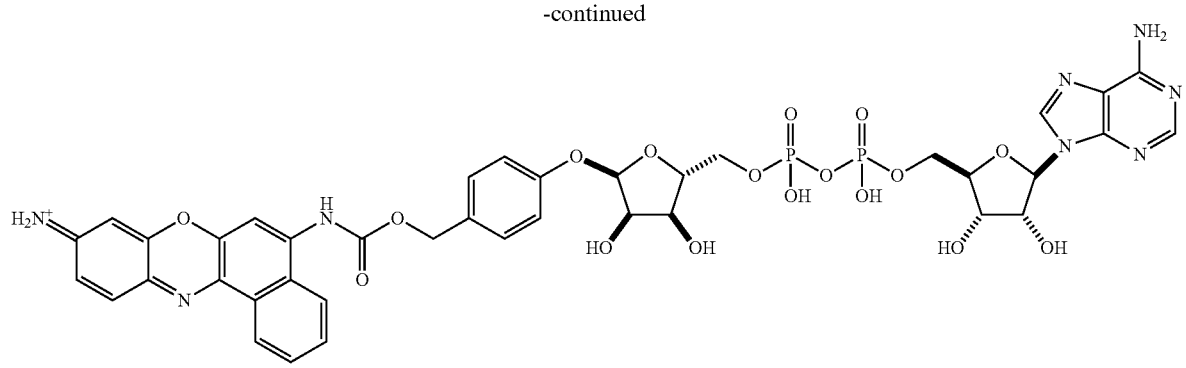
Trimethyl Lock Linker
The trimethyl lock linker shown below rapidly cyclizes and allows access to a range of phenol- or aniline-containing probes.
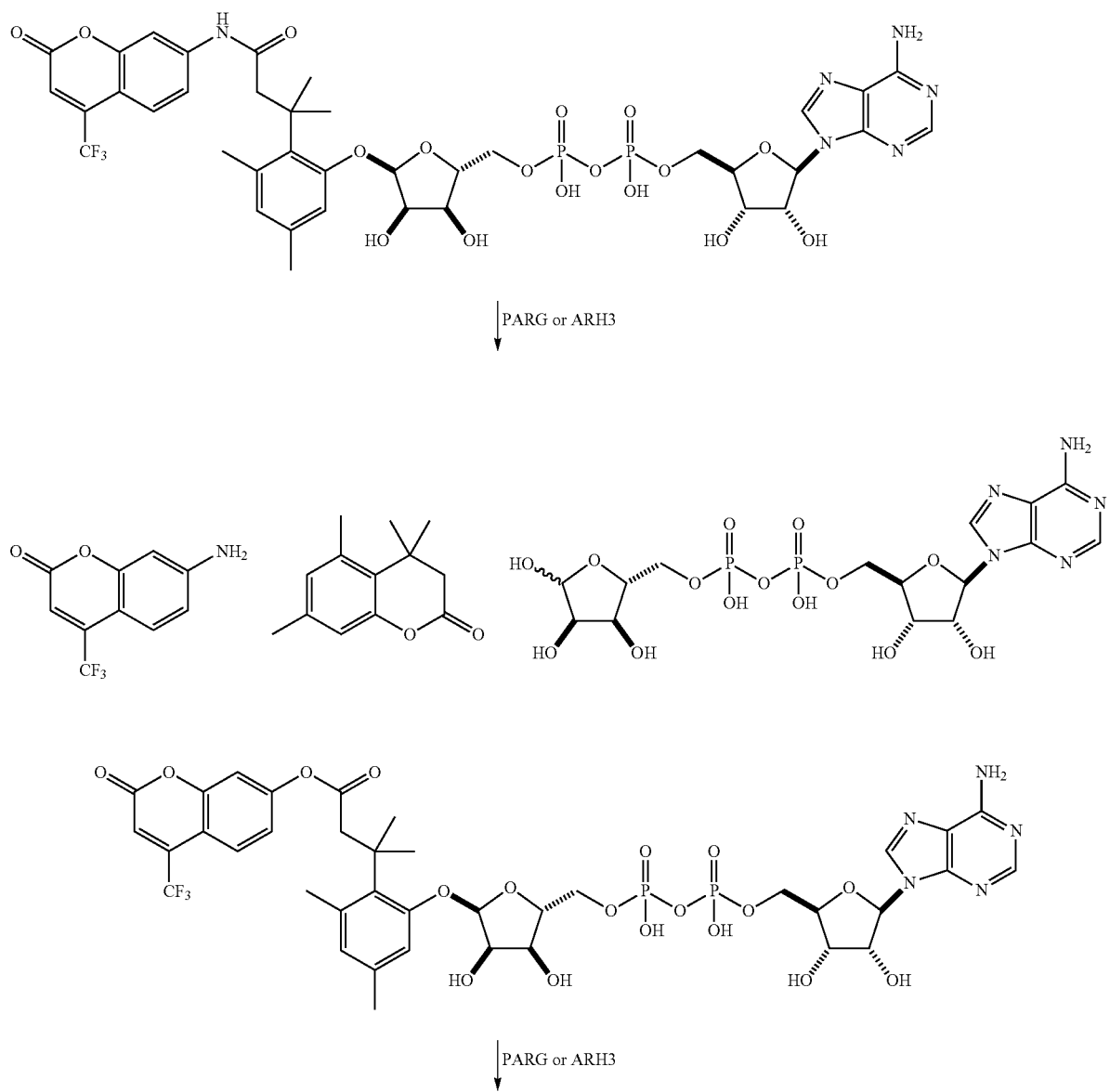

-continued

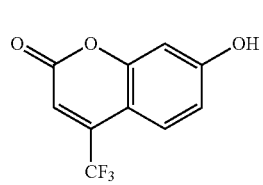 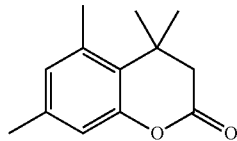 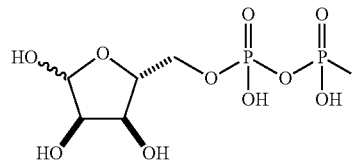 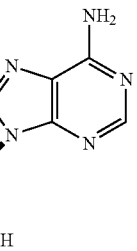

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

AM-L-FS1-PP-FS2-NB    (I), or a salt thereof;
wherein
AM is an aromatic chromophore (A1):

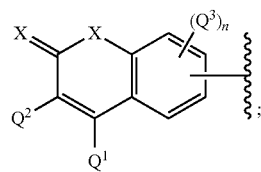

(A1)

wherein
$Q^1$ and $Q^2$ are each independently H, halo, carboxyl, sulfonyl, nitro, aryl, branched or unbranched ($C_1$-$C_6$)alkyl;
$Q^3$ is H or halo;
each X is independently $NR^A$, O, or S; and
$R^A$ is H, or branched or unbranched ($C_1$-$C_6$)alkyl; and
n is 1-3;
wherein aryl and each ($C_1$-$C_6$)alkyl are optionally substituted; or
AM is A2:

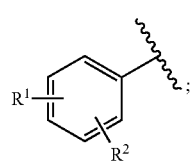

(A2)

wherein
$R^1$ and $R^2$ are each independently halo, carboxyl, sulfonyl, nitro, aryl, branched or unbranched ($C_1$-$C_6$) alkyl;
wherein aryl and ($C_1$-$C_6$)alkyl are optionally substituted; or
AM is an acridine, fluorescein, or quinazoline;
L is a linker: O;

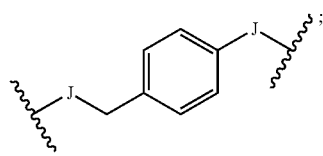

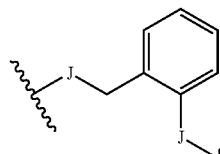

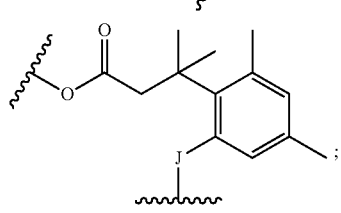

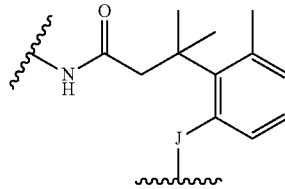

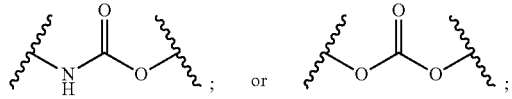

wherein each J is independently O, —N(C=O)O—, or —O(C=O)O—;
FS1 and FS2 are furanose moieties;
PP is a monophosphate, diphosphate, or triphosphate; and NB is a nucleobase (N2):

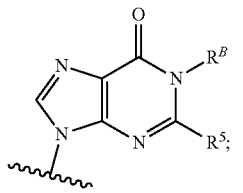

(N2)

wherein
R$^5$ is H or N(R$^B$)$_2$; and
each R$^B$ is independently H, or branched or unbranched (C$_1$-C$_6$)alkyl;
wherein the C5-carbons of FS1 and FS2 are covalently bonded to PP via a C—O bond, the C1-carbon of FS2 is covalently bonded to NB via a C—N bond, and the C1-carbon of FS1 is covalently bonded to AM via L.

2. The compound of claim 1 wherein the aromatic chromophore is an acridine, fluorescein, coumarin, or quinazoline moiety.

3. The compound of claim 1 wherein L is: O.

4. The compound of claim 1 wherein AM is Formula A1: wherein
Q$^1$ is halo, carboxyl, sulfonyl, nitro, aryl, branched or unbranched (C$_1$-C$_6$)alkyl;
Q$^3$ is H;
X is O; and
n is 3;
wherein aryl and (C$_1$-C$_6$)alkyl are optionally substituted.

5. The compound of claim 4 wherein Formula A1 is A:

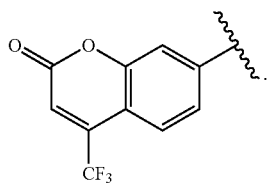

(A)

6. The compound of claim 1 wherein AM is para-nitrophenyl.

7. The compound of claim 1 wherein FS1 and FS2 are Formula FX:

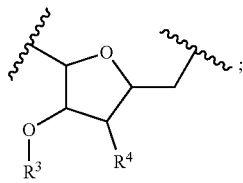

(FX)

wherein
R$^3$ is H or branched or unbranched (C$_1$-C$_6$)alkyl;
R$^4$ is H or OR$^x$; and
R$^x$ is H or branched or unbranched (C$_1$-C$_6$)alkyl.

8. The compound of claim 7 wherein R$^3$ is H and R$^4$ is OH.

9. A compound of Formula I:

AM-L-FS1-PP-FS2-NB    (I), or a salt thereof;
wherein
AM is an aromatic chromophore (A1):

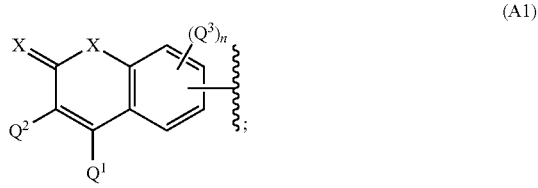

(A1)

wherein
Q$^1$ and Q$^2$ are each independently H, halo, carboxyl, sulfonyl, nitro, aryl, branched or unbranched (C$_1$-C$_6$)alkyl;
Q$^3$ is H or halo;
each X is independently NR$^A$, O, or S; and
R$^A$ is H, or branched or unbranched (C$_1$-C$_6$)alkyl; and
n is 1-3;
wherein aryl and each (C$_1$-C$_6$)alkyl are optionally substituted; or
AM is A2:

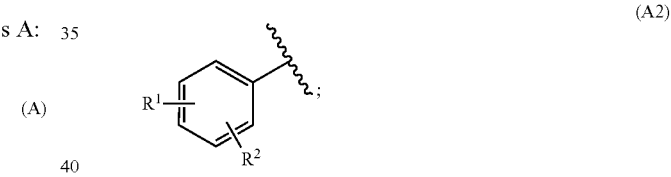

(A2)

wherein
R$^1$ and R$^2$ are each independently halo, carboxyl, sulfonyl, aryl, branched or unbranched (C$_1$-C$_6$)alkyl;
wherein aryl and (C$_1$-C$_6$)alkyl are optionally substituted; or
AM is an acridine, fluorescein, or quinazoline;
L is a linker: O;

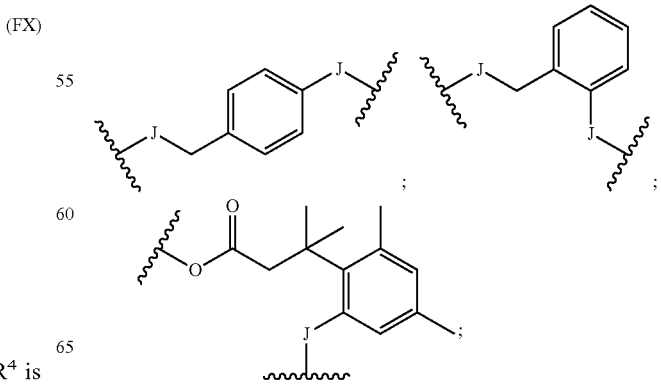

-continued

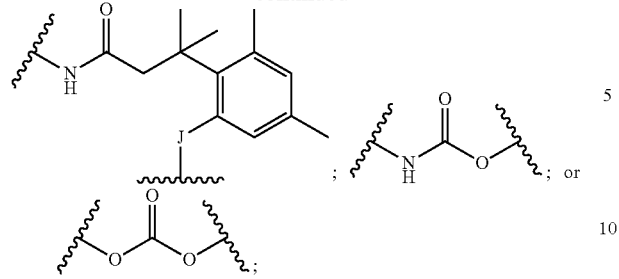

wherein each J is independently O, —N(C=O)O—, or —O(C=O)O—;
FS1 and FS2 are furanose moieties;
PP is a monophosphate, diphosphate, or triphosphate; and
NB is a nucleobase (N1):

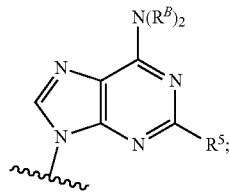

(N1)

wherein
R$^5$ is H or N(R$^B$)$_2$; and
each R$^B$ is independently H, or branched or unbranched (C$_1$-C$_6$)alkyl.

10. The compound of claim 9 wherein R$^5$ is H and each R$^B$ on nitrogen is H.

11. The compound of claim 9 wherein the compound is:

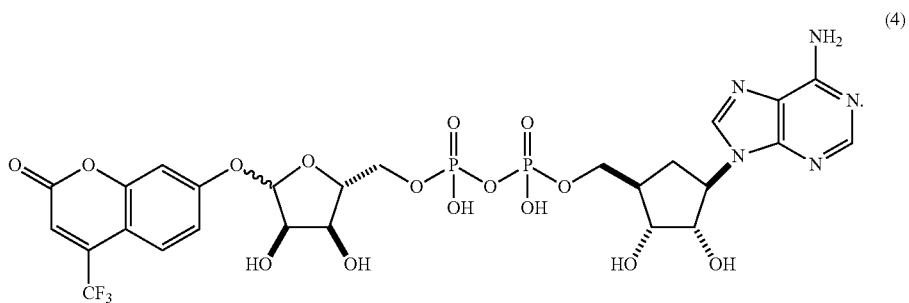

(4)

12. The compound of claim 1 wherein R$^5$ is H and R$^B$ on nitrogen is H.

13. The compound of claim 1 wherein PP is P1:

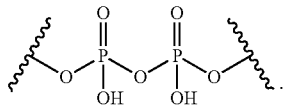

(P1)

14. The compound of claim 1 wherein the compound of Formula I is a compound of Formula II:

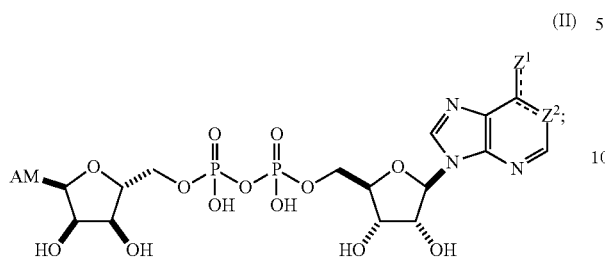

wherein
  ===== is a single or double bond; and
  $Z^1$ is O and $Z^2$ is NH, wherein ===== on $Z^1$ is a double bond and ===== on $Z^2$ is a single bond.

15. The compound of claim 1 wherein the compound is:

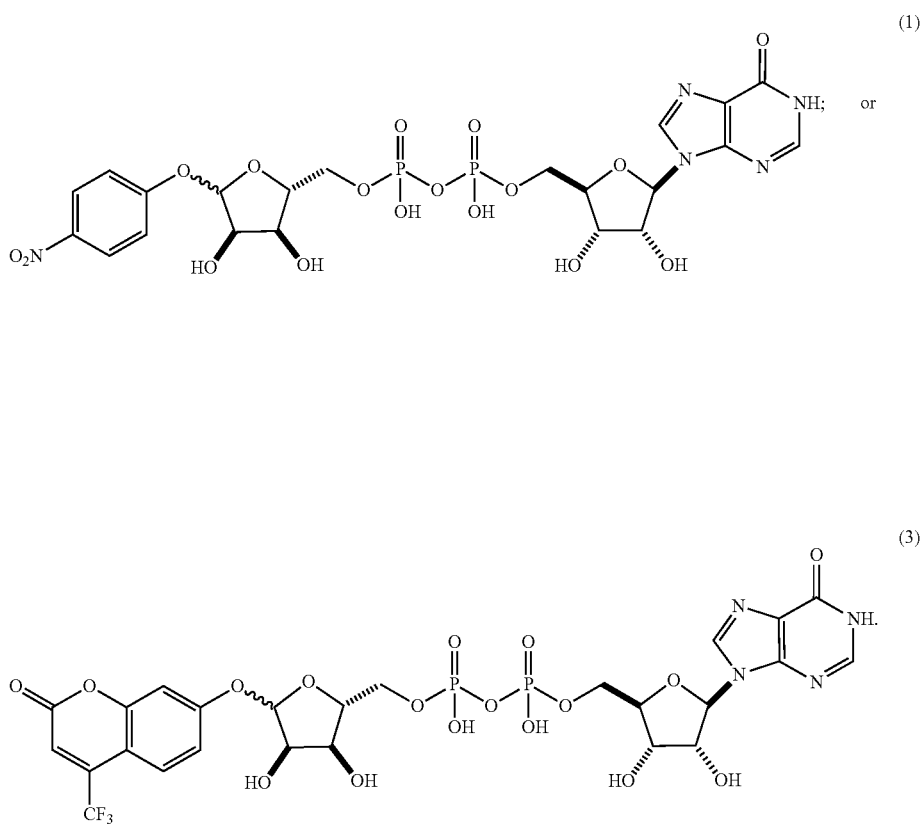

16. A method of detecting poly(ADP-ribose) (PAR) cellular activity comprising:

a) contacting a compound of claim 1 and constituents of a cell or a whole cell lysate to form a mixture; and
b) detecting changes in fluorescence in the mixture;

wherein
  the compound is a substrate of poly(ADP-ribose) glycohydrolase (PARG), and PARG selectively hydrolyses the compound to release the AM moiety as AM-OH;
  the compound is a substrate of ADP-ribosylhydrolase 3 (ARH3), and ARH3 selectively hydrolyses the compound to release the AM moiety as AM-OH;
  or a combination thereof;
wherein AM-OH is fluorescent and an increase in fluorescence indicates PAR cellular activity.

17. The method of claim 16 wherein the constituents of a cell are from a whole-cell lysate; or
  wherein the constituents of a cell are from a whole-cell lysate, and the whole-cell lysate is a whole-cell lysate of cancer cells.

18. The method of claim 16 wherein PAR cellular activity is continuously interrogated by monitoring changes in fluorescence; or
  wherein the kinetics of PAR cellular activity are measured by changes in fluorescence; or
  wherein an increase in fluorescence further indicates PAR degrading activity.

* * * * *